US012704505B2

(12) United States Patent
Lee

(10) Patent No.: US 12,704,505 B2
(45) Date of Patent: Aug. 11, 2026

(54) METHODS AND KITS FOR DETECTING TARGET SUBSTANCES

(71) Applicant: JL MEDILABS, INC., Cheongju-si (KR)

(72) Inventor: Jong Jin Lee, Cheongju-si (KR)

(73) Assignee: JL MEDILABS, INC., Cheongju-si (KR)

( * ) Notice: Subject to any disclaimer, the term of this patent is extended or adjusted under 35 U.S.C. 154(b) by 1559 days.

(21) Appl. No.: 17/040,821

(22) PCT Filed: Aug. 28, 2019

(86) PCT No.: PCT/KR2019/011003
§ 371 (c)(1),
(2) Date: Sep. 23, 2020

(87) PCT Pub. No.: WO2020/045984
PCT Pub. Date: Mar. 5, 2020

(65) Prior Publication Data

US 2023/0176064 A1 Jun. 8, 2023

(30) Foreign Application Priority Data

Aug. 28, 2018 (KR) ........................ 10-2018-0101453
Oct. 16, 2018 (KR) ........................ 10-2018-0123312
Oct. 16, 2018 (KR) ........................ 10-2018-0123313

(51) Int. Cl.
*G01N 33/542* (2006.01)
*C12Q 1/6804* (2018.01)
(Continued)

(52) U.S. Cl.
CPC ......... *G01N 33/542* (2013.01); *C12Q 1/6804* (2013.01); *G01N 33/54373* (2013.01); *G01N 33/582* (2013.01); *G01N 2458/10* (2013.01)

(58) Field of Classification Search
None
See application file for complete search history.

(56) References Cited

U.S. PATENT DOCUMENTS

2008/0044834 A1 2/2008 Heyduk
2009/0162861 A1 6/2009 Mathis et al.
(Continued)

FOREIGN PATENT DOCUMENTS

JP H10332594 A * 12/1998
JP 2005528121 A 9/2005
(Continued)

OTHER PUBLICATIONS

Rothwell et al. Multiparameter single-molecule fluorescence spectroscopy reveals heterogeneity of HIV-1 reverse transcriptase: primer/template complexes. PNAS 100(4): 1655-1660 (2003). (Year: 2003).*
(Continued)

*Primary Examiner* — Samuel C Woolwine
(74) *Attorney, Agent, or Firm* — STIP Law Group, LLC

(57) ABSTRACT

Provided is a method for detecting target substances. The method includes a) introducing a sample containing target substances onto a substrate, b) allowing detection probes conjugated with docking strands to specifically bind to the target substances, c) introducing one or more separate strands capable of complementary binding to the docking strands into the docking strands, either the docking strands or the separate strands, or both, are labeled with at least one donor fluorescent substance and at least one acceptor fluorescent substance, and d) measuring fluorescence signals generated by the FRET between the donor fluorescent substance and the acceptor fluorescent substance to identify the target substances.

20 Claims, 29 Drawing Sheets

Specification includes a Sequence Listing.

Fret strand 1
(FRET efficiency 1)
Donor strand (common)
Detection antibody 1
Docking strand 1
Donor 1
Donor 2
Acceptor

(51) Int. Cl.
*G01N 33/543* (2006.01)
*G01N 33/58* (2006.01)

(56) References Cited

U.S. PATENT DOCUMENTS

| | | | | |
|---|---|---|---|---|
| 2010/0184614 | A1* | 7/2010 | Ye | C12Q 1/6813 506/9 |
| 2011/0250598 | A1* | 10/2011 | Fischer | C12Q 1/686 435/6.12 |
| 2014/0242600 | A1* | 8/2014 | Xing | G01N 21/6458 435/14 |
| 2016/0138096 | A1* | 5/2016 | Min | C12Q 1/6823 506/18 |
| 2016/0298107 | A1* | 10/2016 | O'Farrell | C12N 15/1013 |

FOREIGN PATENT DOCUMENTS

| | | | |
|---|---|---|---|
| JP | 2006500588 | A | 1/2006 |
| KR | 2020110005025 | U | 5/2011 |
| KR | 20130102688 | A | 9/2013 |
| KR | 20140011760 | A | 1/2014 |
| KR | 20140121221 | A | 10/2014 |
| KR | 1020160039229 | A | 4/2016 |
| KR | 20170096619 | A | 8/2017 |
| KR | 20180130654 | A | 12/2018 |

OTHER PUBLICATIONS

Thermofisher. Amine-Reactive Crosslinker Chemistry. [online] [retrieved on Feb. 20, 2025] retrieved from https://www.thermofisher.com/us/en/home/life-science/protein-biology/protein-biology-learning-center/protein-biology-resource-library/pierce-protein-methods/amine-reactive-crosslinker-chemistry.htm (Year: 2025).*

Pathways to Chemistry. [online] [retrieved on Feb. 20, 2025] retrieved from https://pathwaystochemistry.com/study-guide-general-chemistry-1/covalent-bonds-and-lewis-dot-structures/covalent-bonds/bond-length-and-bond-strength/ (Year: 2025).*

Lee Supplemental Information [online] Dec. 28, 2017 [retrieved on Feb. 20, 2025] retrieved from https://molecularbrain.biomedcentral.com/articles/10.1186/s13041-017-0344-5#Sec14 (Year: 2017).*

Ambia-Garrido et al. A model for structure and thermodynamics of ssDNA and dsDNA near a surface: A coarse grained approach. Computer Physics Communications 181:2001-2007 (2010). (Year: 2010).*

Auer Supporting Information [online] Sep. 5, 2017 [retrieved on Feb. 20, 2025] retrieved from https://pubs.acs.org/doi/10.1021/acs.nanolett.7b03425 (Year: 2017).*

ATTO-TEC [online] [retrieved on Feb. 20, 2025] retrieved from https://www.atto-tec.com/fileadmin/user_upload/Katalog_Flyer_Support/R_0_-Tabelle_2018_web.pdf (Year: 2025).*

Jungmann et al. Quantitative super-resolution imaging with qPAINT. Nature Methods 13(5):439-442 (2016). (Year: 2016).*

International Search Report of PCT/KR2019/011003, Dec. 6, 2019, English translation.

Jongjin Lee et al, Accelerated super-resolution imaging with FRET-PAINT, Molecular Brain, 2017, vol. 10, article No. 63, pp. 1-9, BioMedCentral, London, United Kingdom.

Nina S. Deubner-Helfmann et al, Correlative Single-Molecule FRET and DNA-PAINT Imaging, Nano Letters, Jun. 26, 2018, vol. 18, pp. 4626-4630, ACS Publications, Washington D.C., USA.

Alexander Gust et al, A Starting Point for Fluorescence-Based Single-Molecule Measurements in Biomolecular Research, Molecules, 2014, vol. 19, pp. 15824-15865, MDPI, Basel, Switzerland.

Alexander Auer et al, Fast, background-free DNA-PAINT imaging using FRET-based probes, Nano Letters, Sep. 5, 2017. vol. 17, pp. 6428-6434, ACS Publications, Washington D.C., USA.

Ralf Jungmann et al, Multiplexed 3D cellular super-resolution imaging with DNA-PAINT and Exchange-PAINT, Nature Methods, Mar. 2014, vol. 11, No. 3, pp. 313-321, Nature America, Inc., New York, USA.

Ankur Jain et al, Probing cellular protein complexes using single-molecule pull-down, Nature, May 26, 2011, vol. 473, pp. 484-489, Macmilan Publishers Limited, New York, USA.

Zhengyang Zhang et al, Ultrahigh-throughput single-molecule spectroscopy and spectrally resolved super-resolution microscopy, Nature Methods, Aug. 17, 2015, vol. 2, pp. 1-6, Nature America, Inc., New York, USA.

Extended European Search Report of EP 19 856 6101, Aug. 5, 2022.

Jongjin Lee et al, Accelerated super-resolution imaging with FRET-PAINT, Molecular Brain, Dec. 1, 2017, vol. 10, No. 64, pp. 1-9 , BioMed Central, Berlin, Germany.

Nina S. Deubner-Helfmann et al, Correlative Single-Molecule FRET and DNA-PAINT Imaging, Nano Letters, 2018, vol. 18, pp. 4626-4630, ACS Publications, Washington DC, USA.

Alexander Auer et al, Fast, Background-Free DNA-PAINT Imaging Using FRET-Based Probes, Nano Letters, 2017, vol. 17, pp. 6428-6434, ACS Publications, Washington DC, USA.

Zhengyang Zhang et al, Ultrahigh-throughput single-molecule spectroscopy and spectrally resolved super-resolution microscopy, Brief Communications, Aug. 17, 2015, vol. 12, No. 10, pp. 935-940, Nature America, Inc. New York, USA.

Joerg Schnitzbauer et al, Super-resolution microscopy with DNA-PAINT, Protocol, 2017, vol. 12, No. 6, pp. 1198-1228, Nature Protocols, London, United Kingdom.

Gertrude Bunt & Fred S. Wouters, FRET from single to multiplexed signaling events, CrossMark, 2017, Mar. 23, 2017, vol. 9, pp. 119-129, Springer, Berlin, Germany.

* cited by examiner

[Fig. 1a]
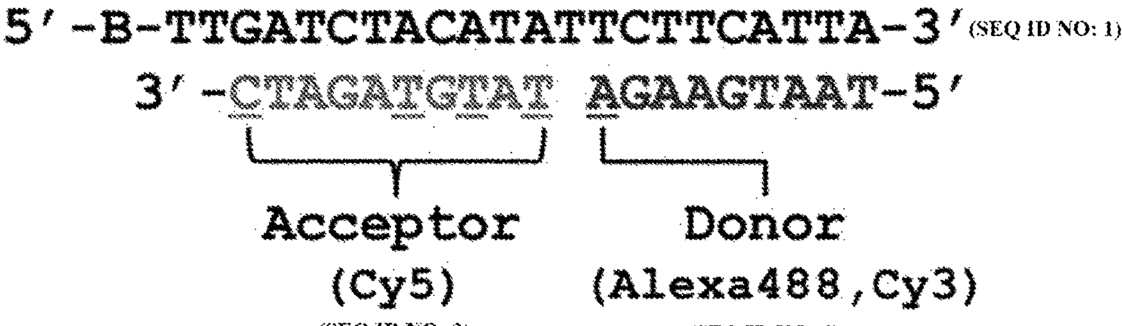
[Fig. 1b]
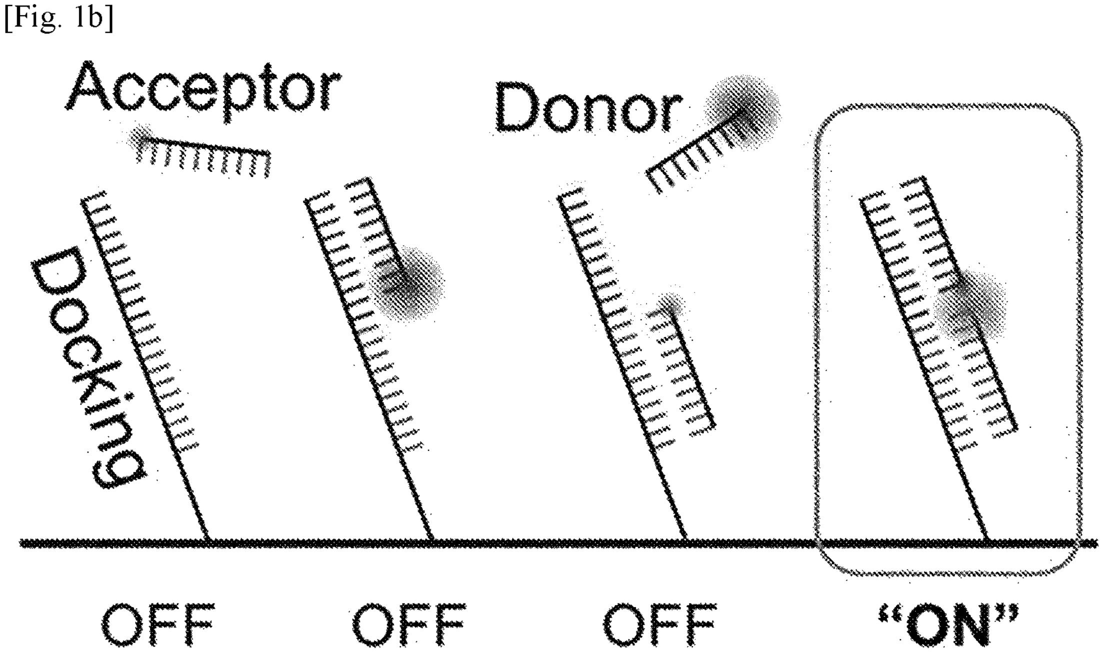

[Fig. 1c]
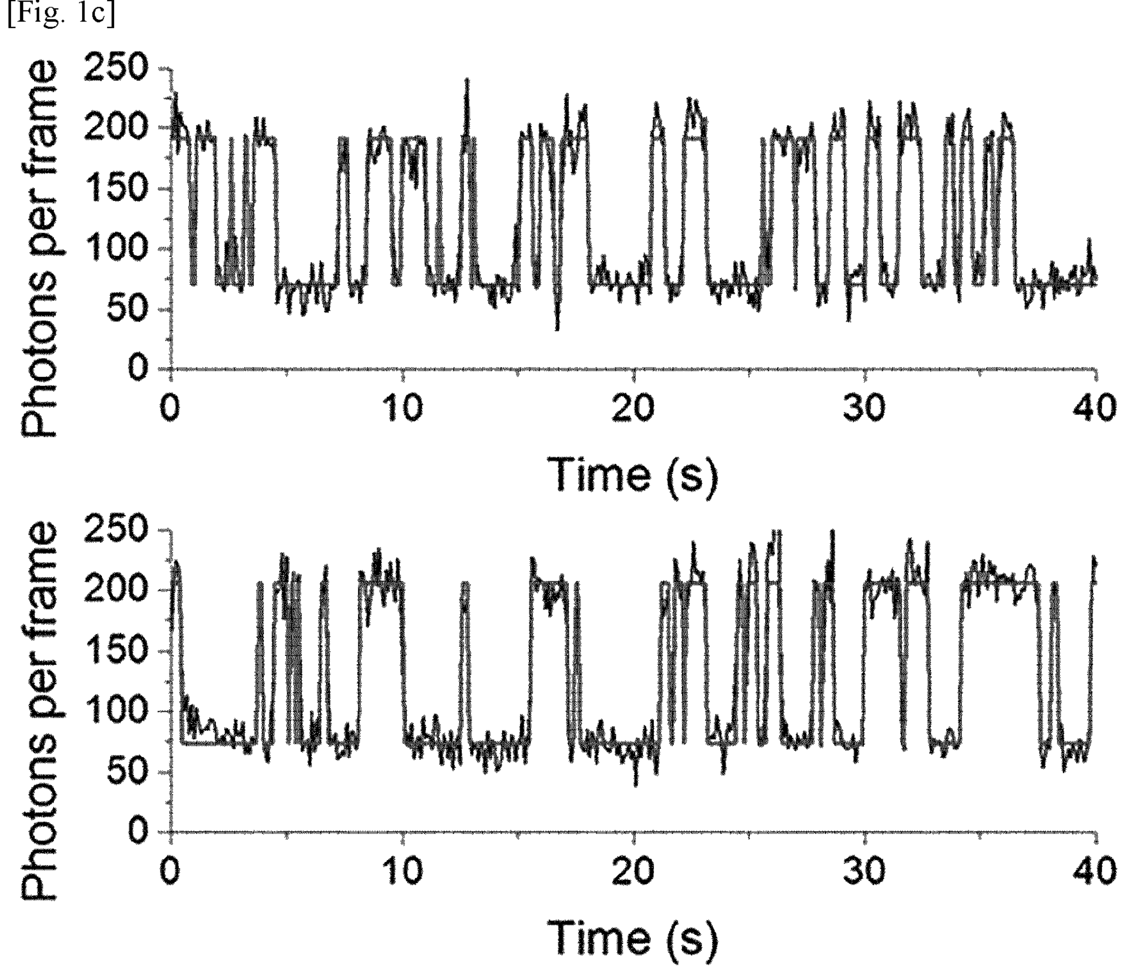

[Fig. 1d]
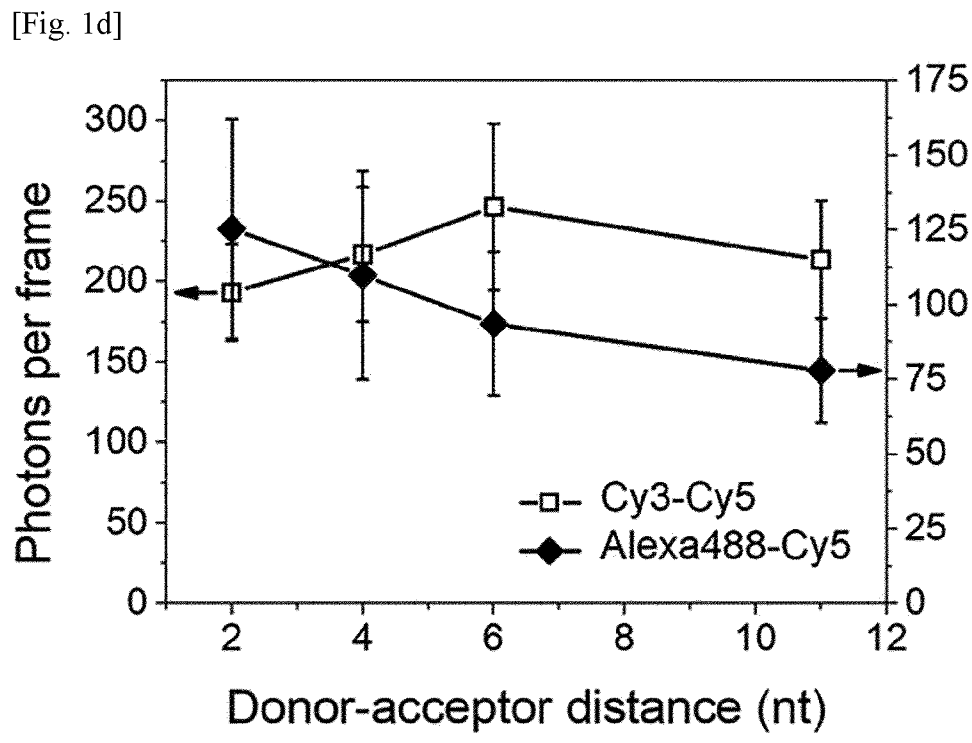
[Fig. 1e]
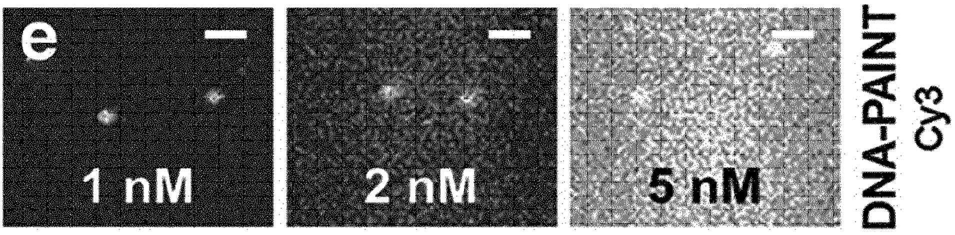
[Fig. 1f]
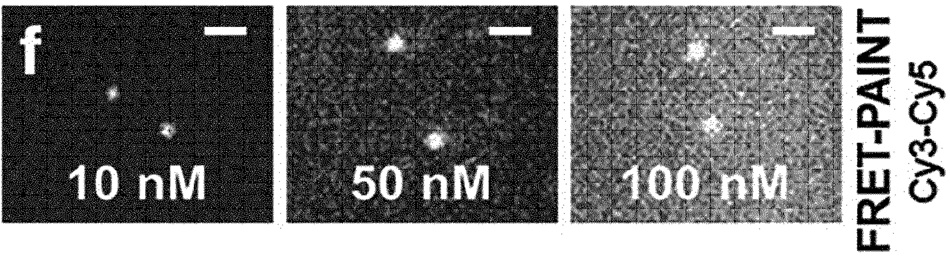

[Fig. 1g]
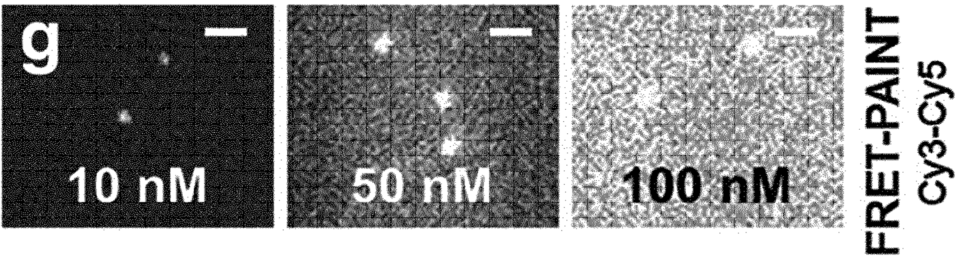
[Fig. 1h]
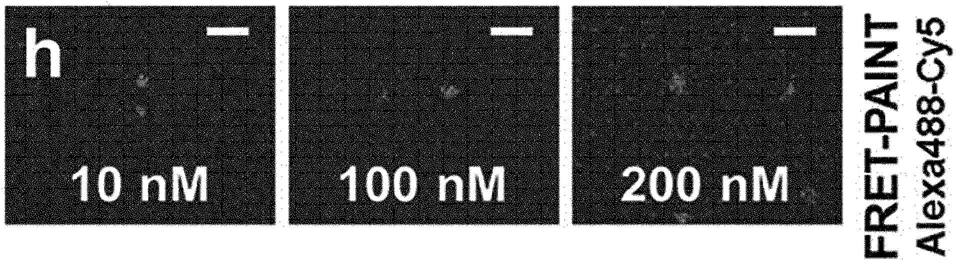
[Fig. 1i]
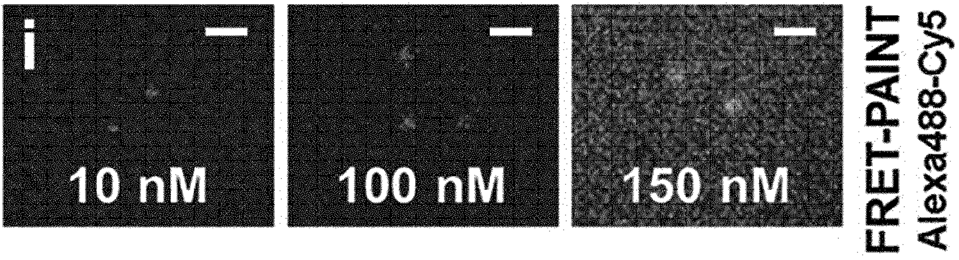

[Fig. 1j]
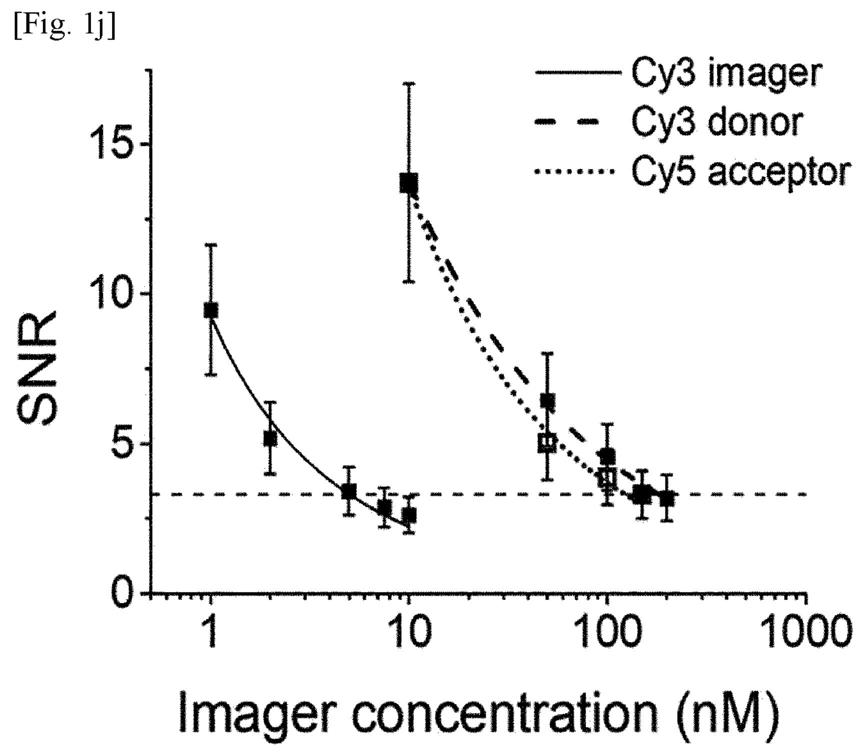
[Fig. 1k]
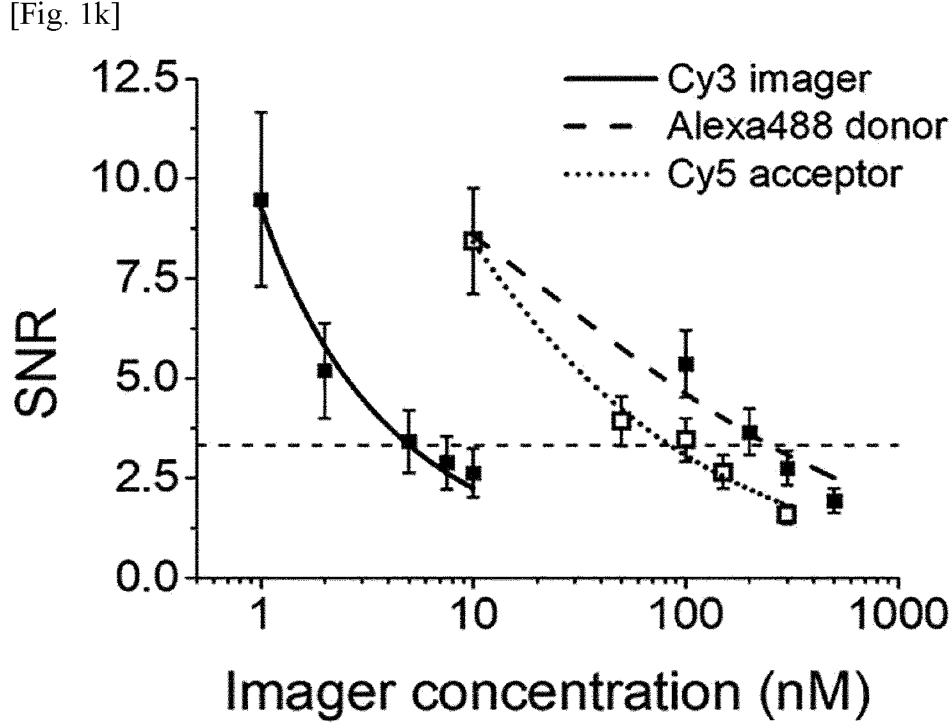

[Fig. 2a]
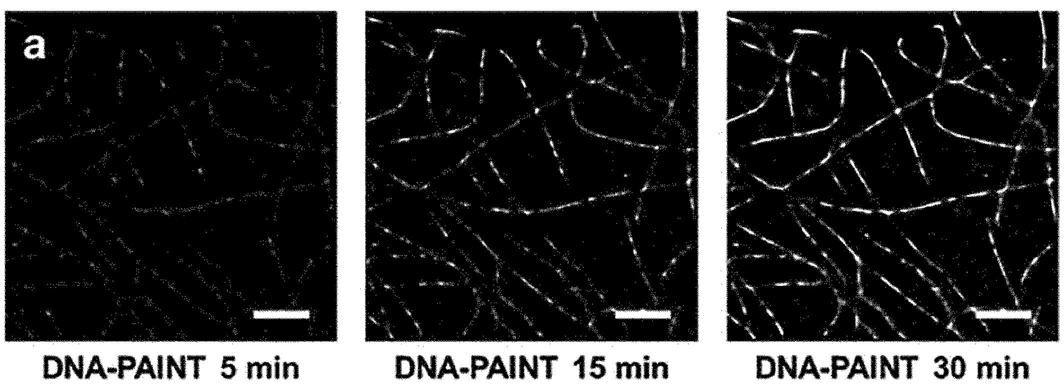
[Fig. 2b]
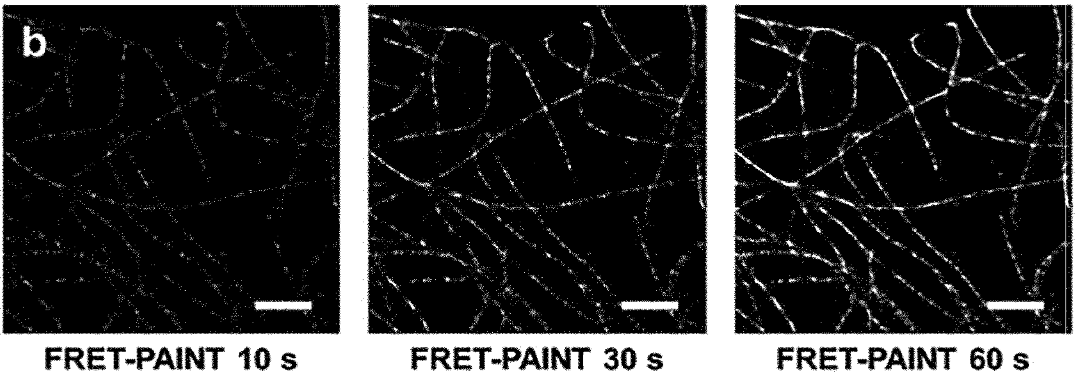
[Fig. 2c]
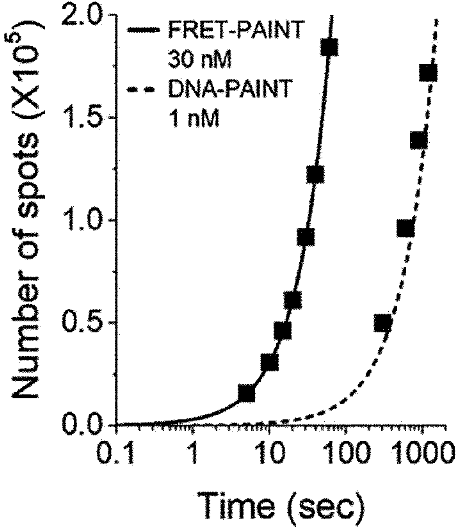

[Fig. 2d]
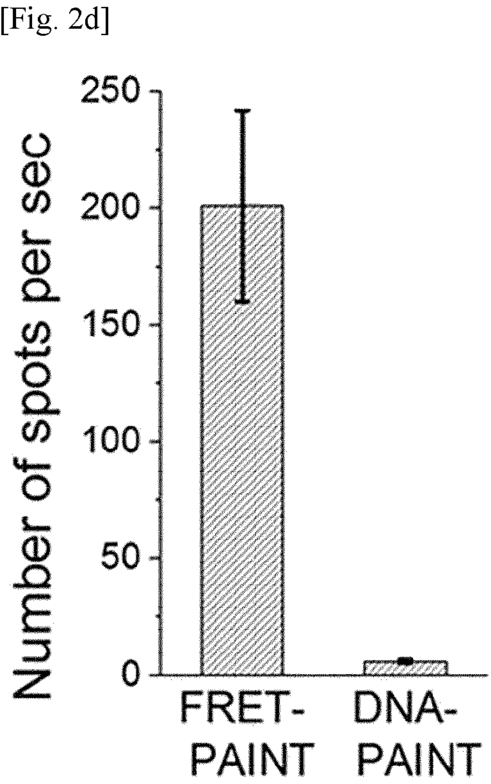
[Fig. 2e]
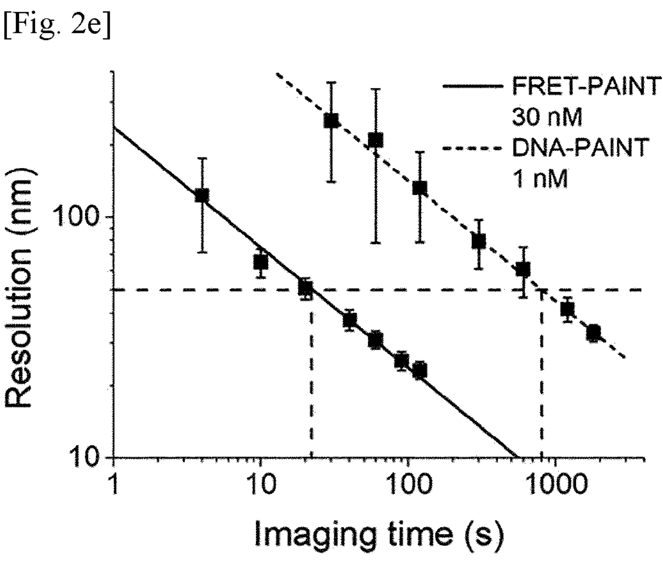

[Fig. 3a]
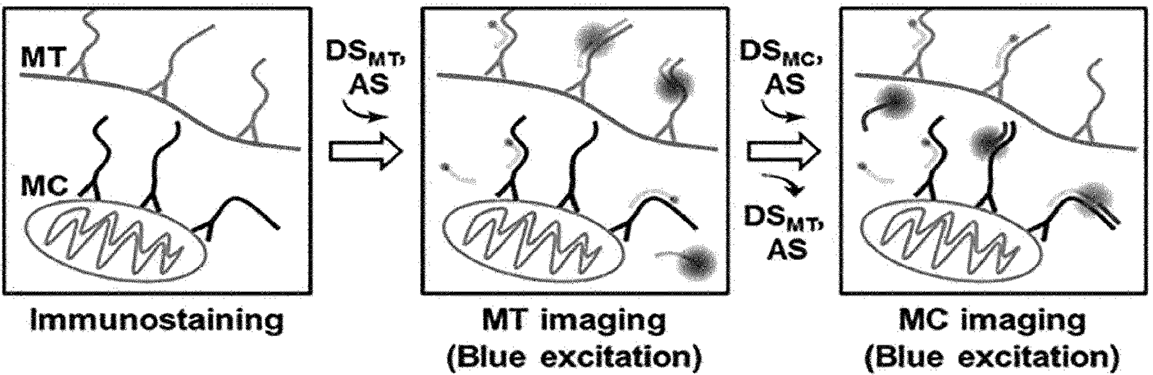
[Fig. 3b]
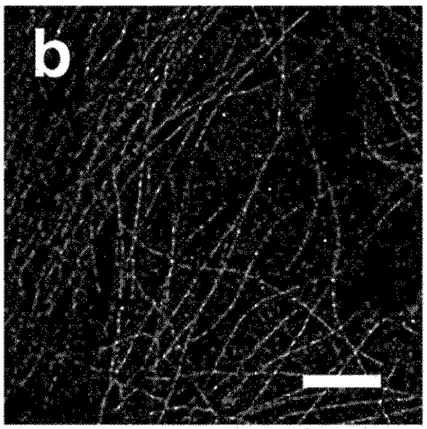
[Fig. 3c]
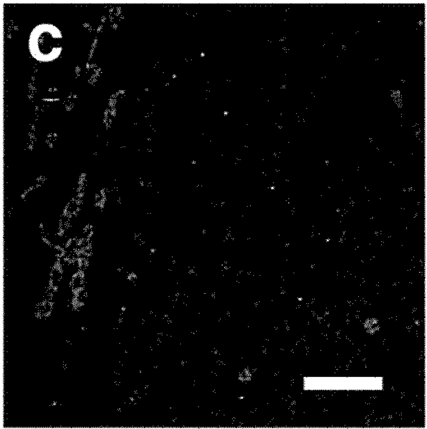

[Fig. 3d]
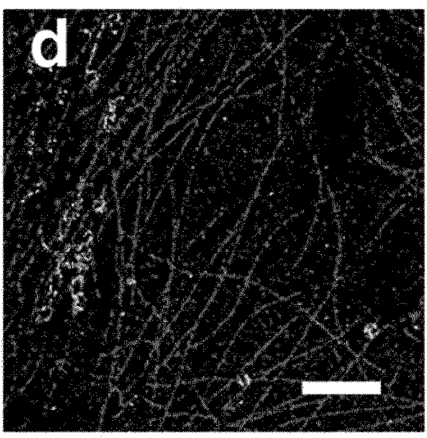
[Fig. 3e]
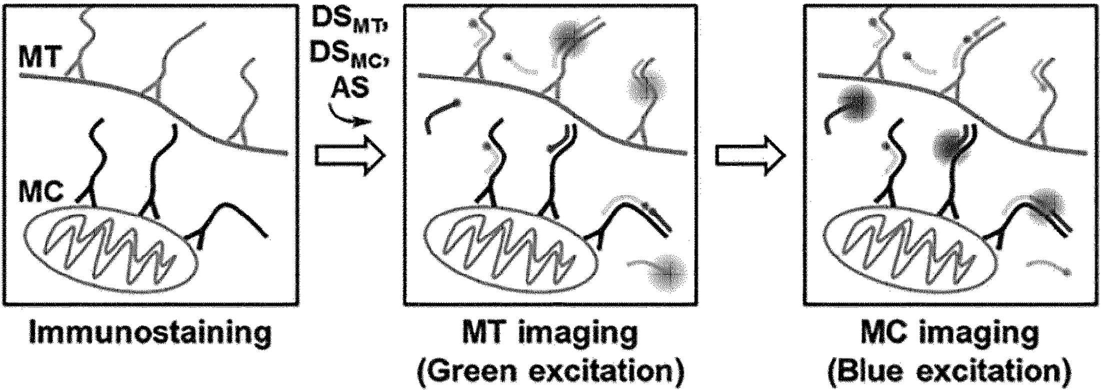
[Fig. 3f]
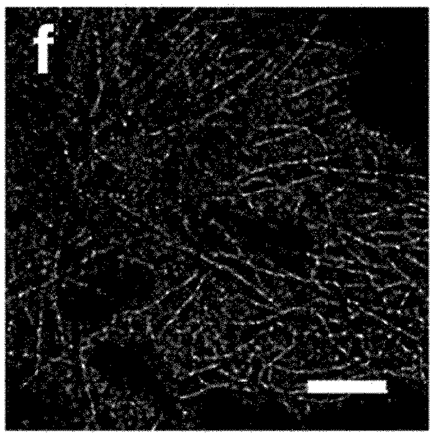

[Fig. 3g]
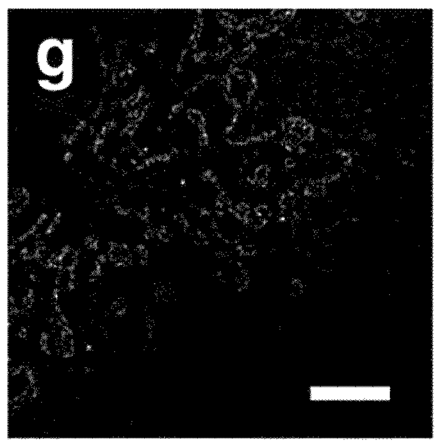
[Fig. 3h]
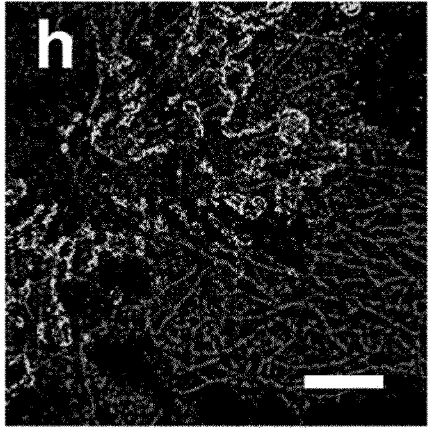

[Fig. 4a]
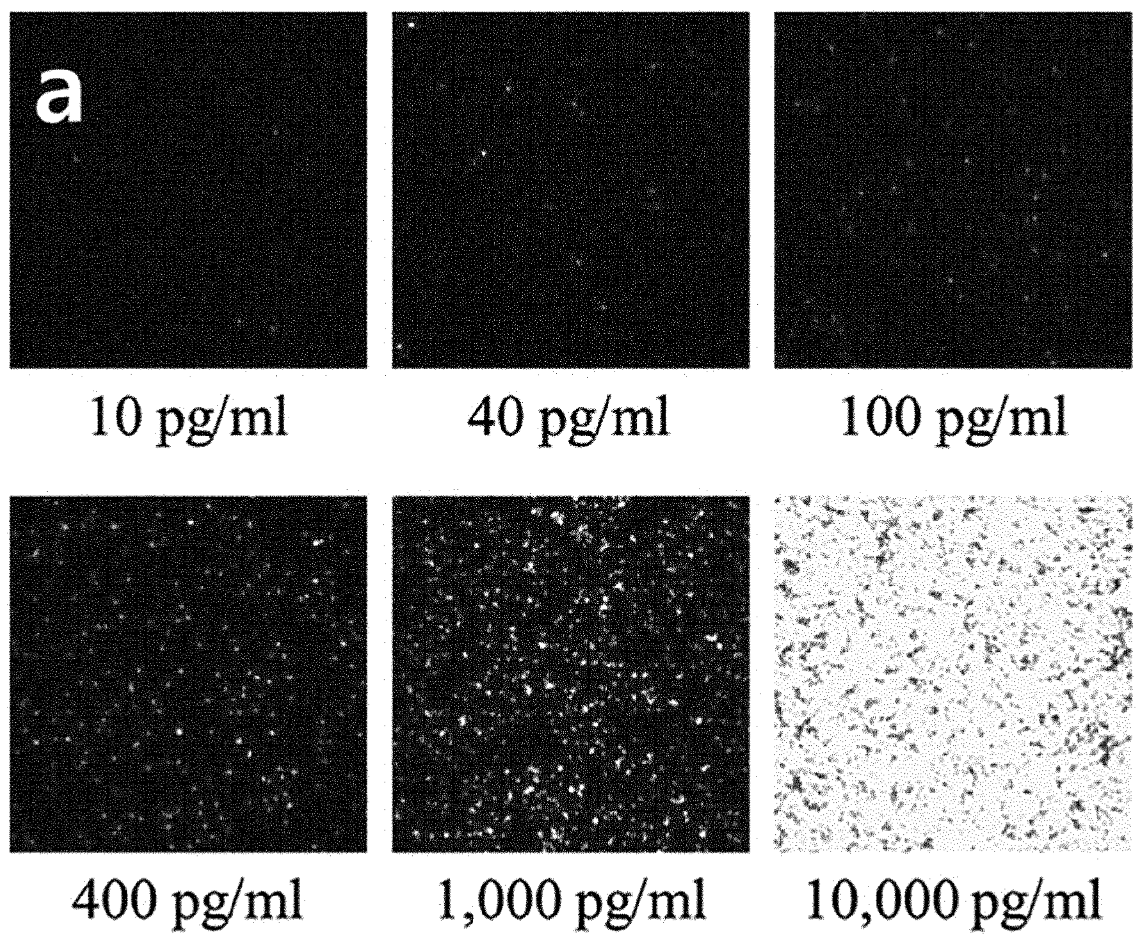
[Fig. 4b]
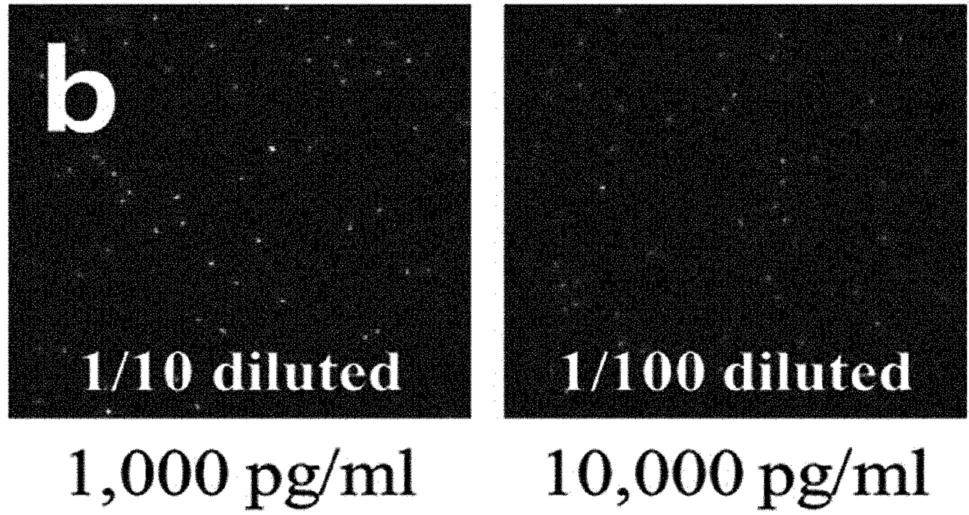

[Fig. 4c]
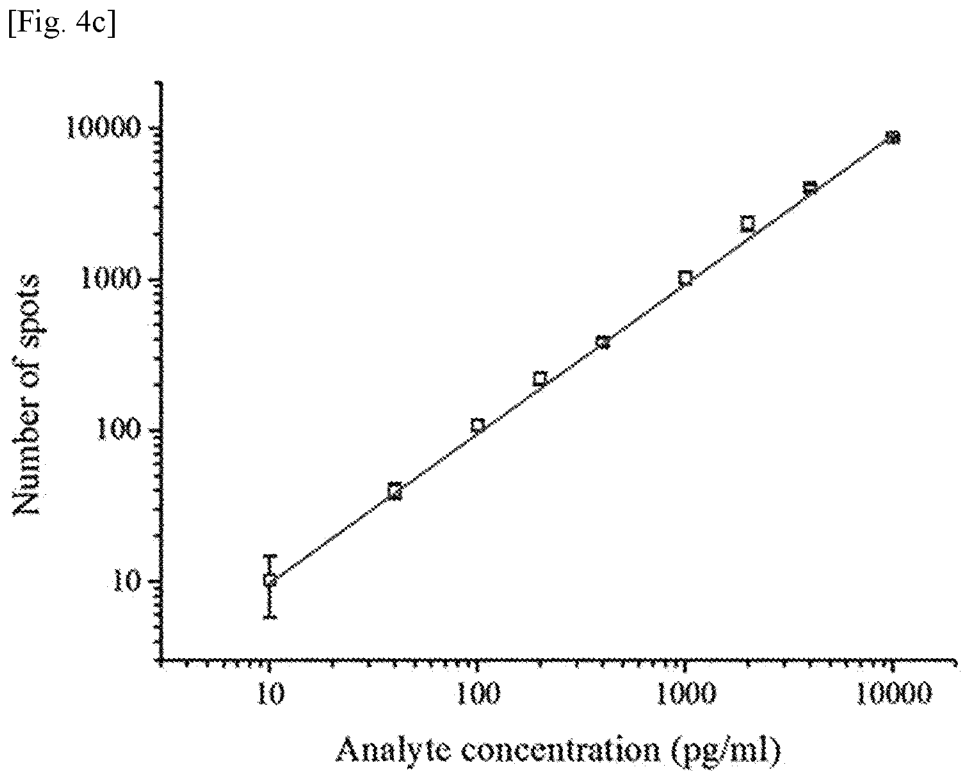
[Fig. 5]
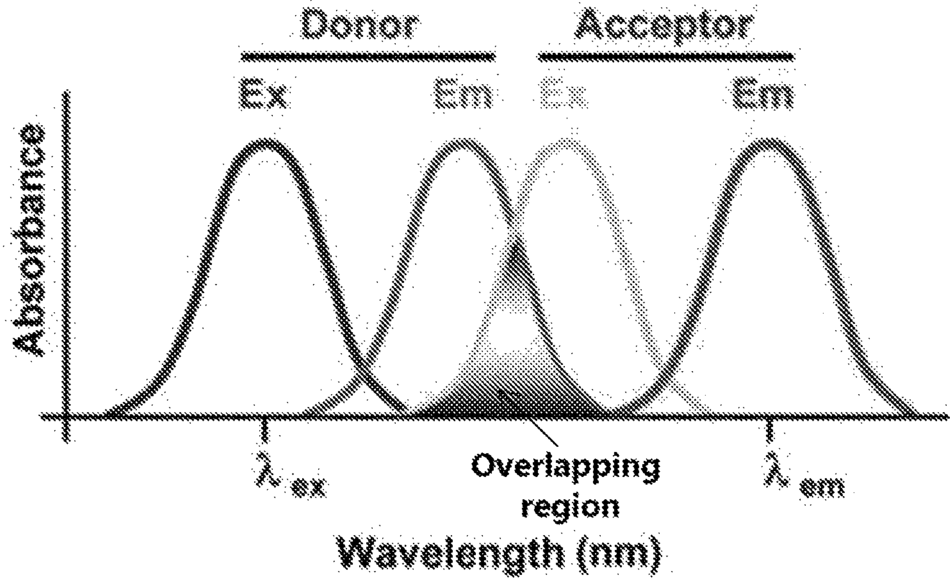

[Fig. 6]
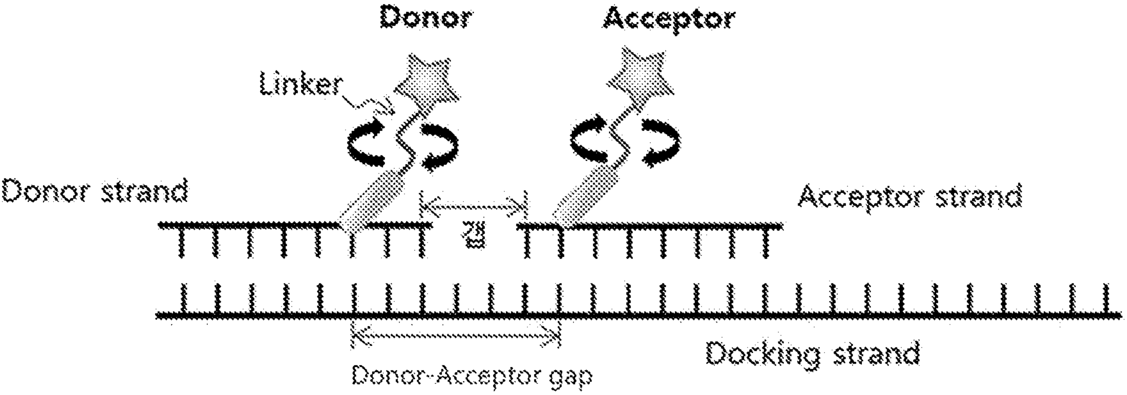
[Fig. 7]
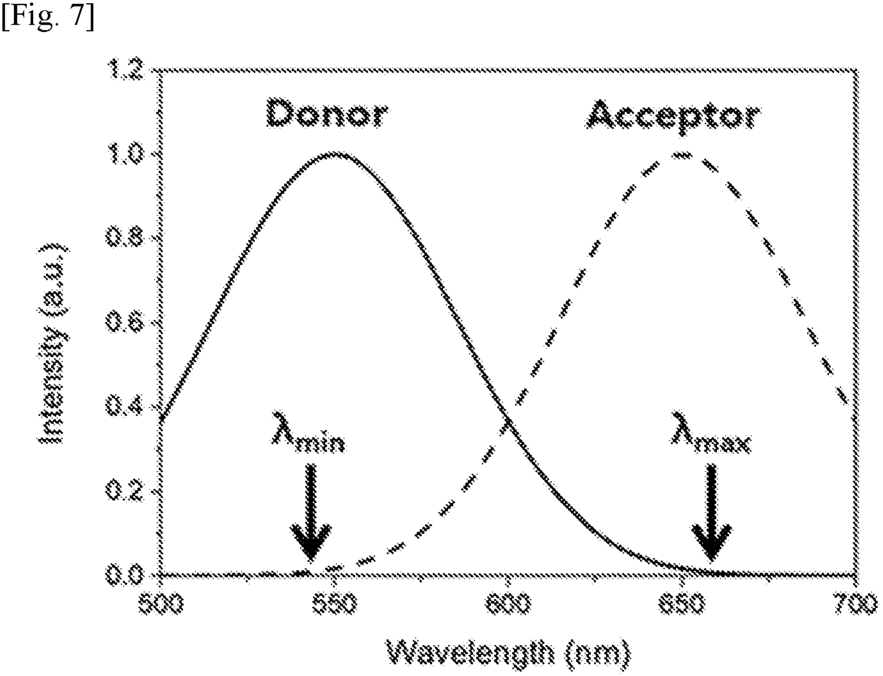

[Fig. 8a]
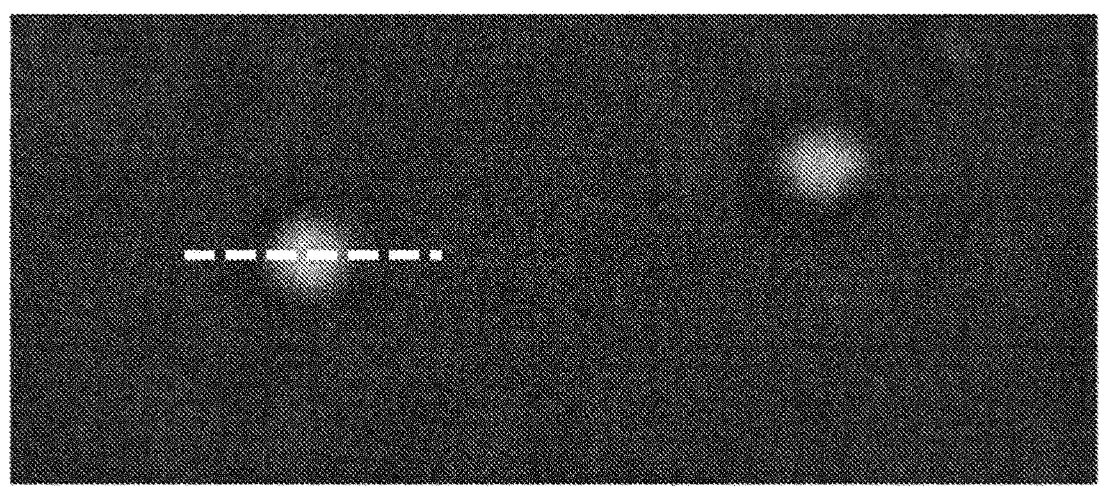
[Fig. 8b]
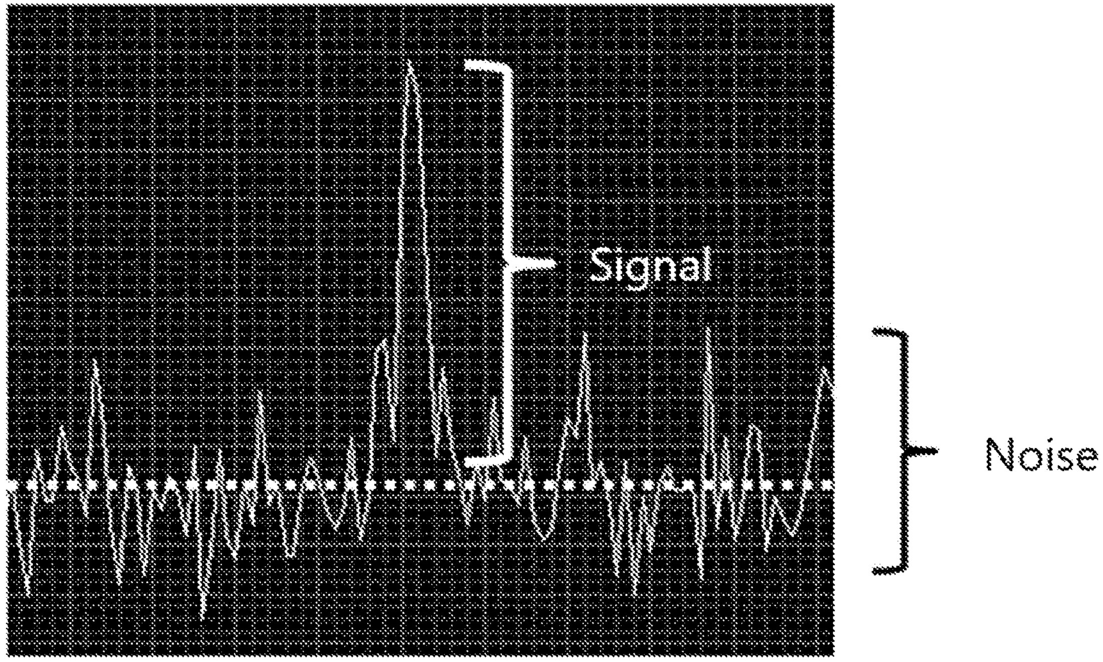

[Fig. 9]
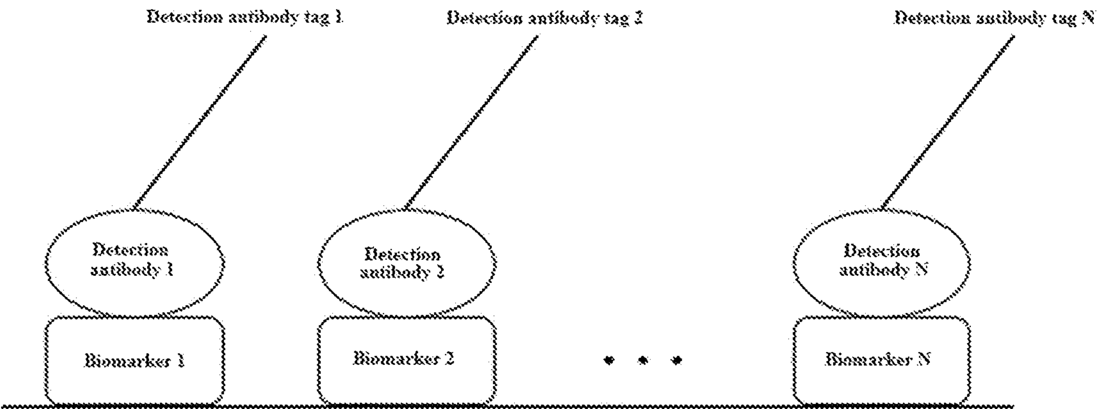
[Fig. 10]
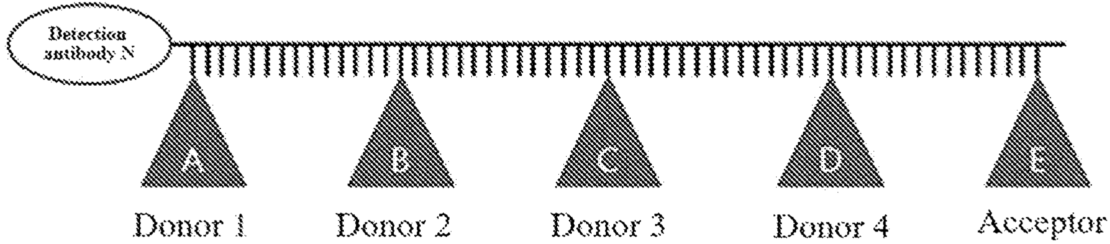
[Fig. 11]
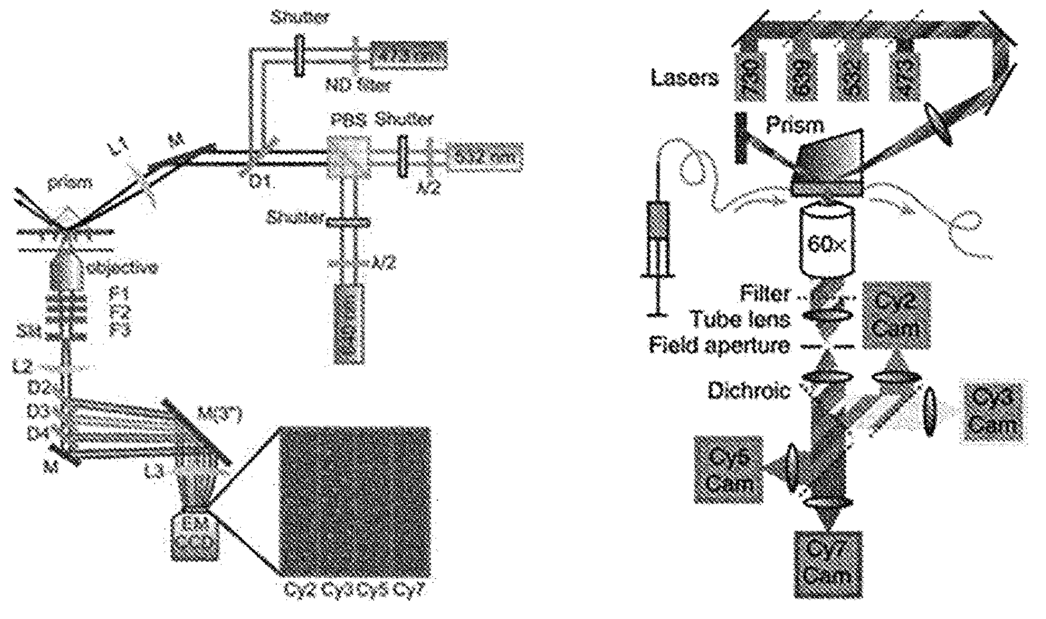

[Fig. 12]
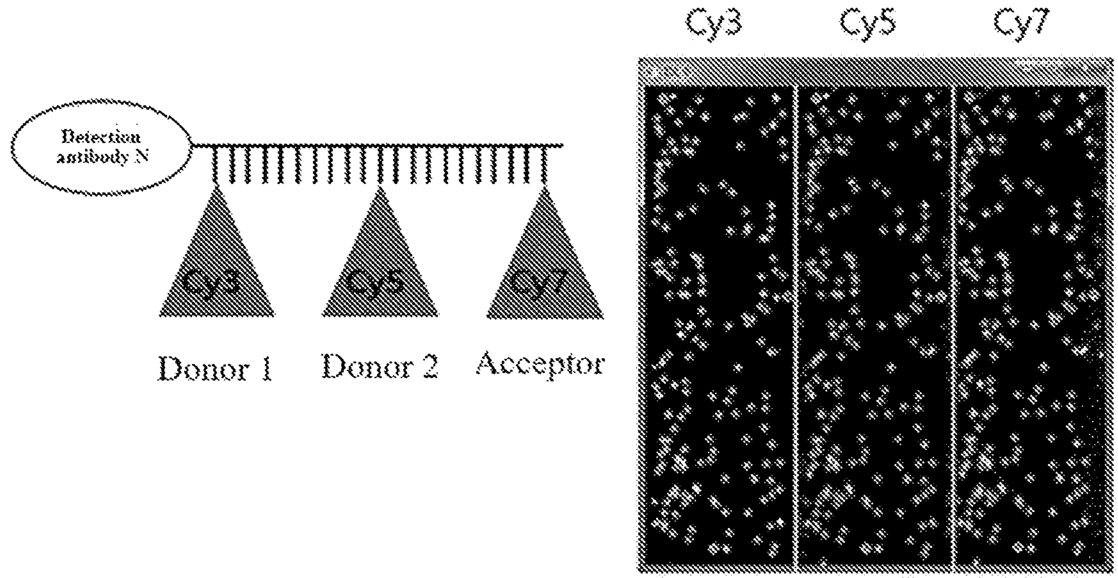
[Fig. 13]
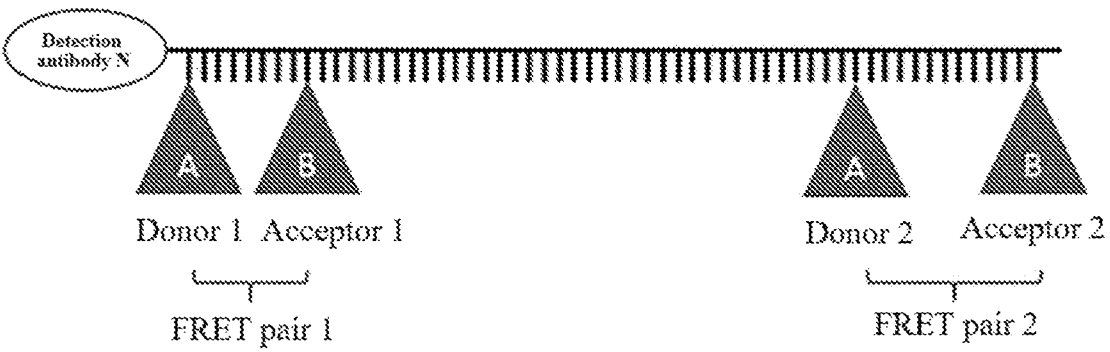
[Fig. 14a]
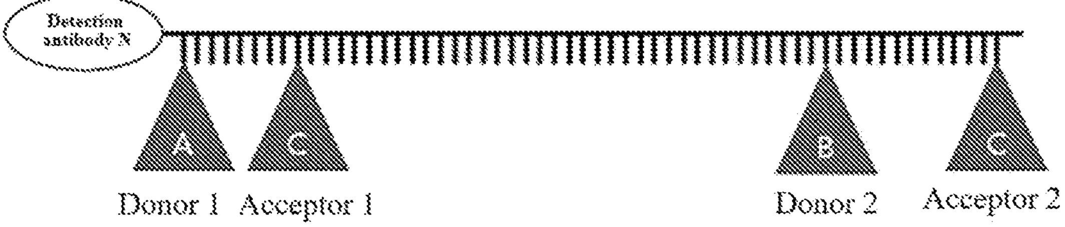

[Fig. 14b]
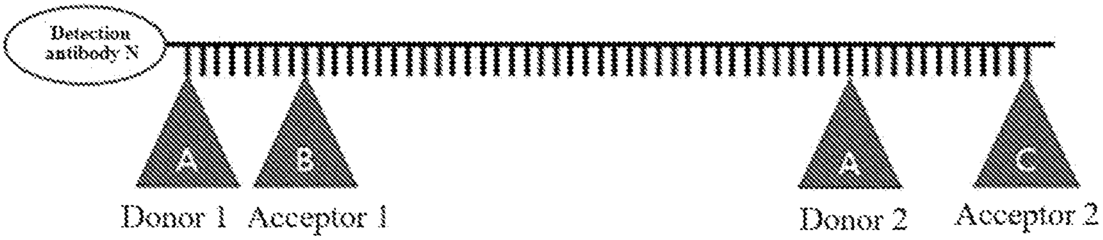
[Fig. 14c]
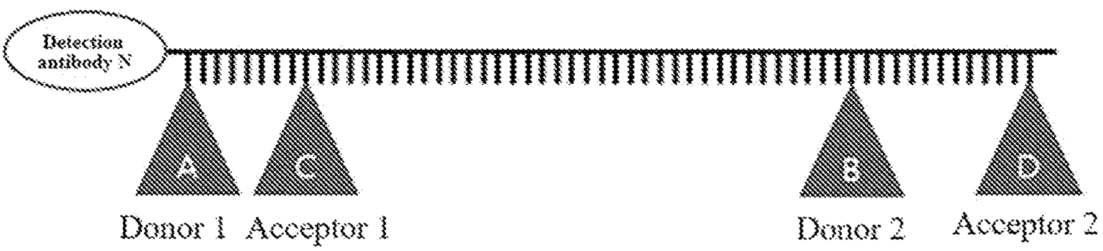
[Fig. 15]
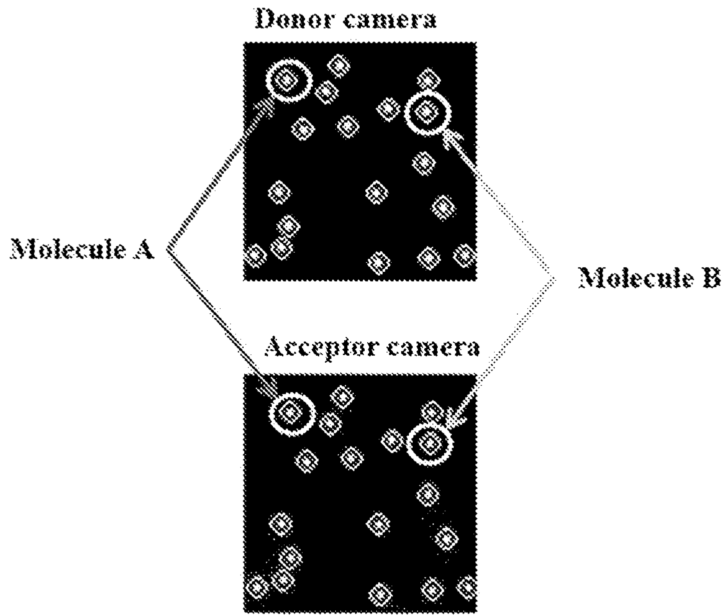

[Fig. 16]
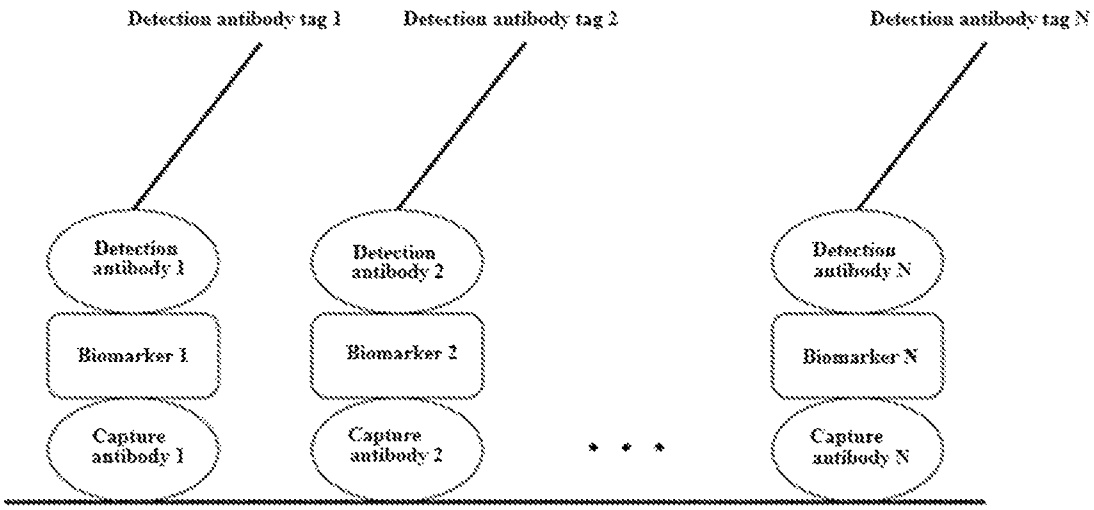
[Fig. 17]
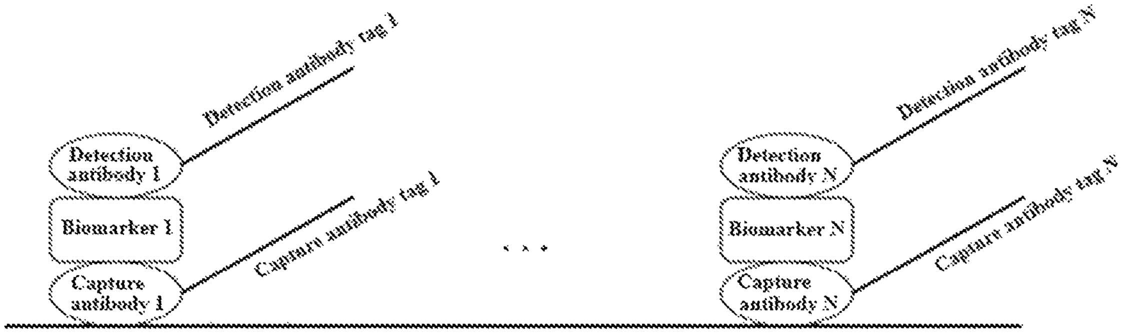
[Fig. 18]
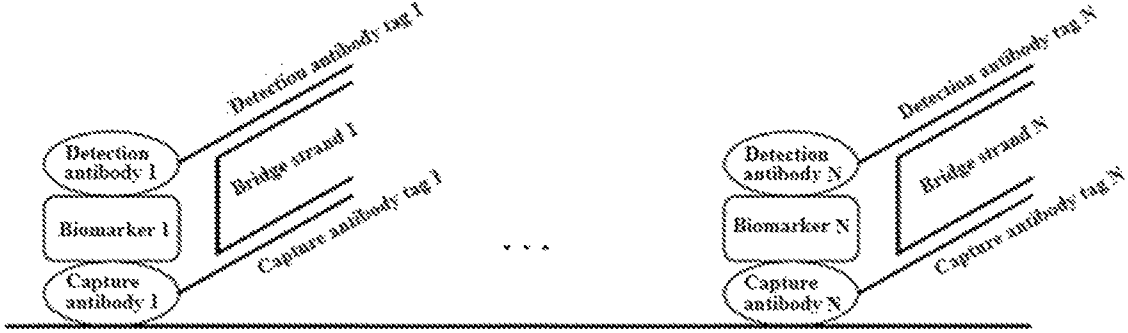

[Fig. 19]
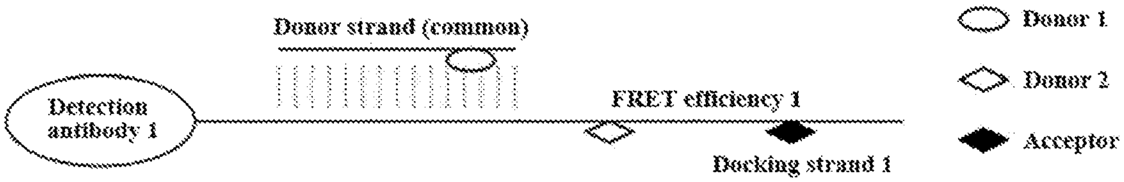
[Fig. 20]
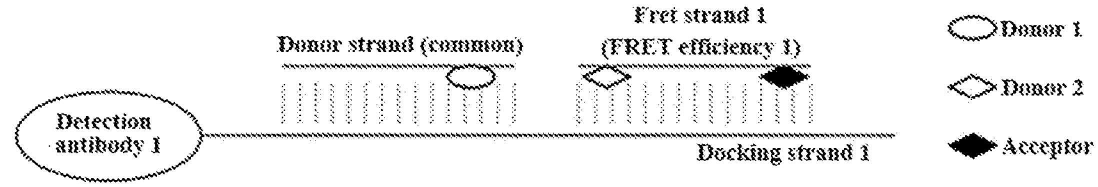
[Fig. 21]
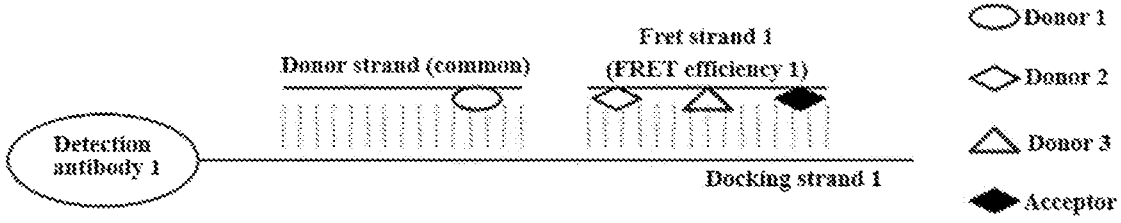
[Fig. 22]
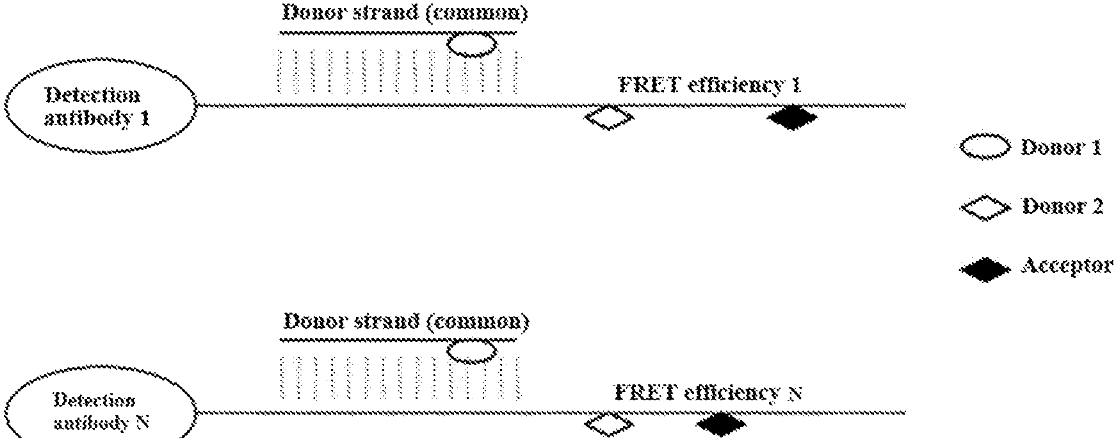

[Fig. 23]
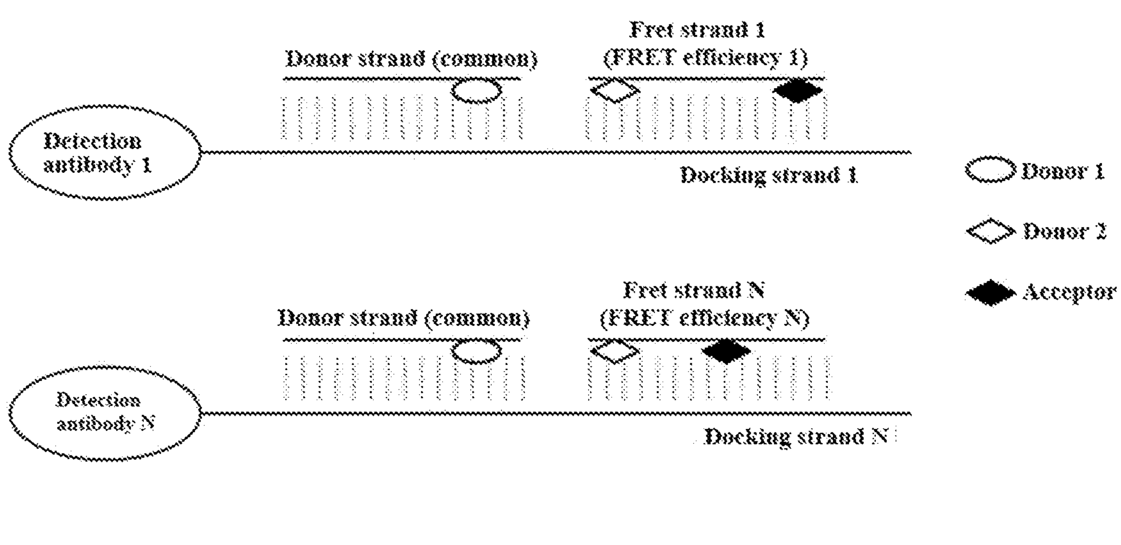
[Fig. 24]
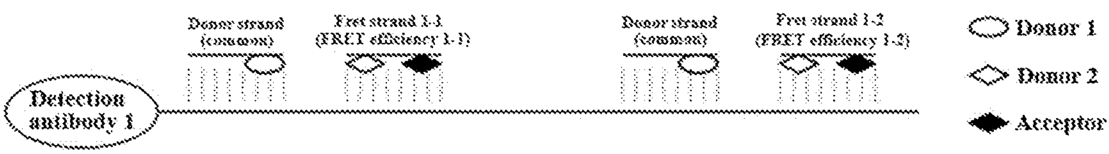
[Fig. 25]
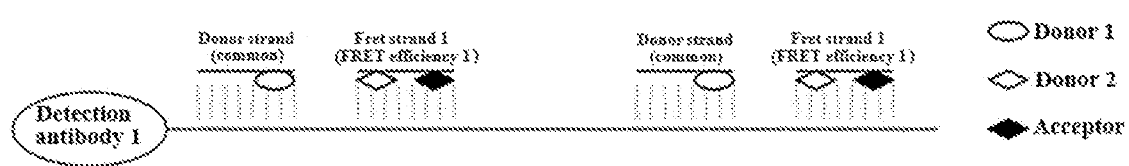

[Fig. 26]
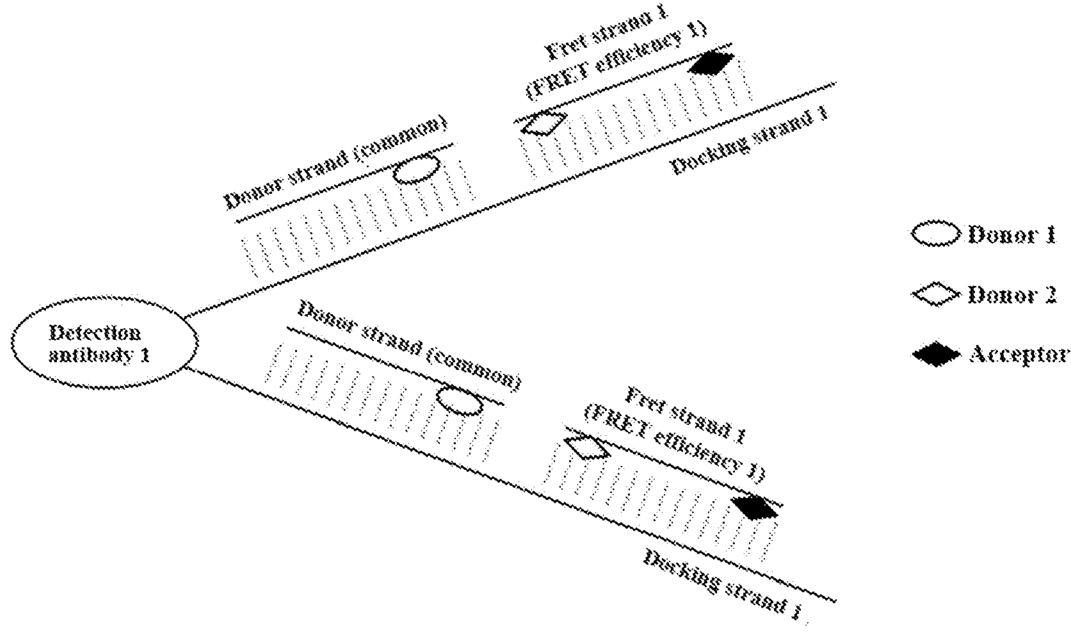
[Fig. 27]
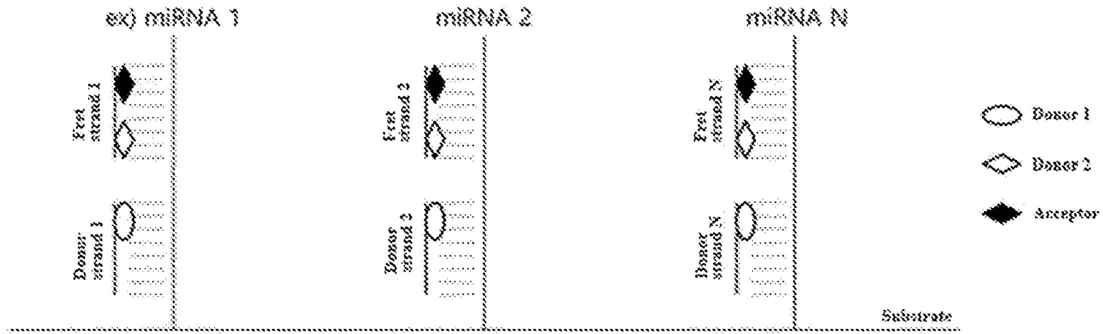

[Fig. 28]
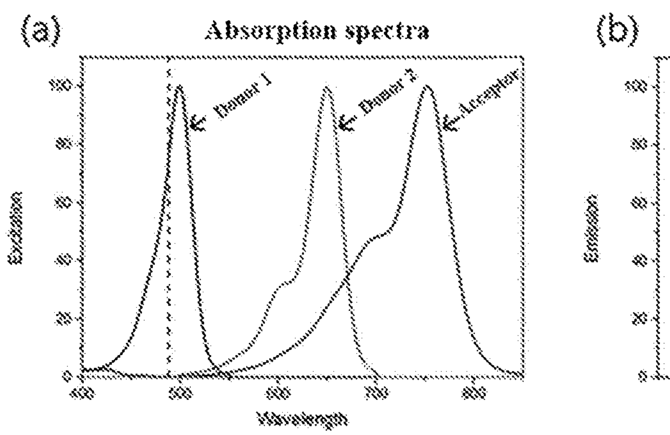
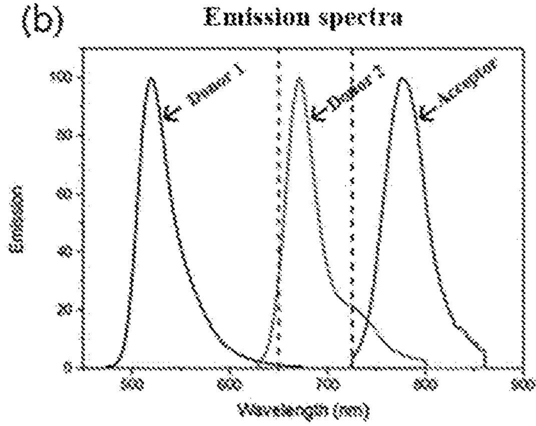
[Fig. 29]
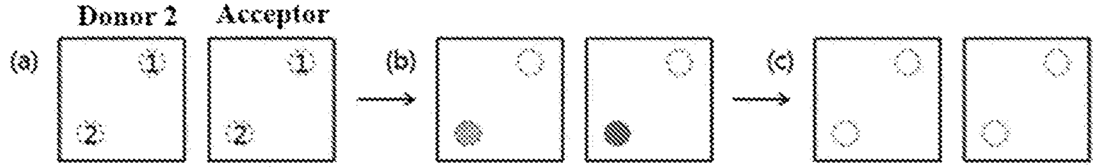
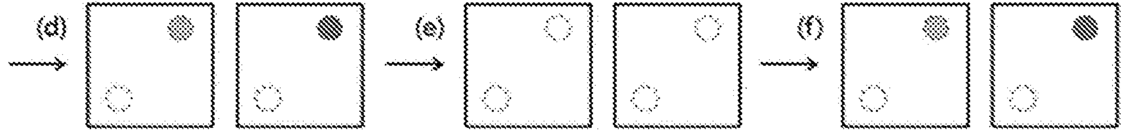

[Fig. 30a]
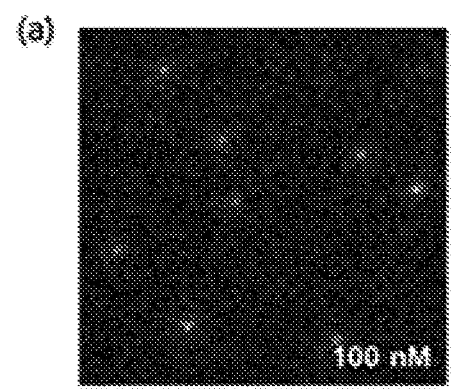
[Fig. 30b]
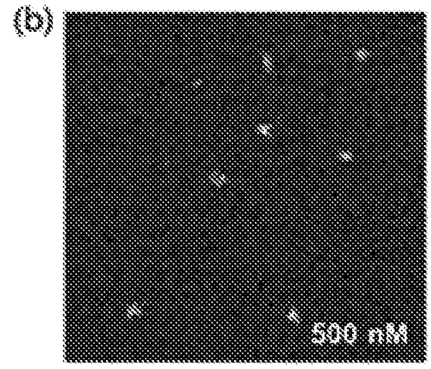
[Fig. 30c]
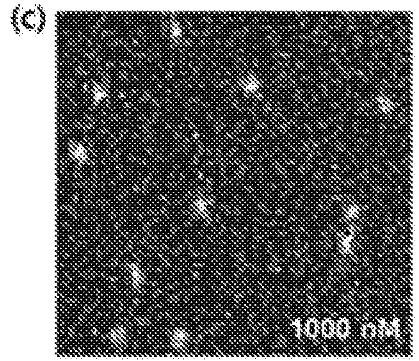

[Fig. 31]
Detection antibody 1
Donor
A1
Detection antibody 2
Donor
A2
Detection antibody N
Donor
AN
[Fig. 32]
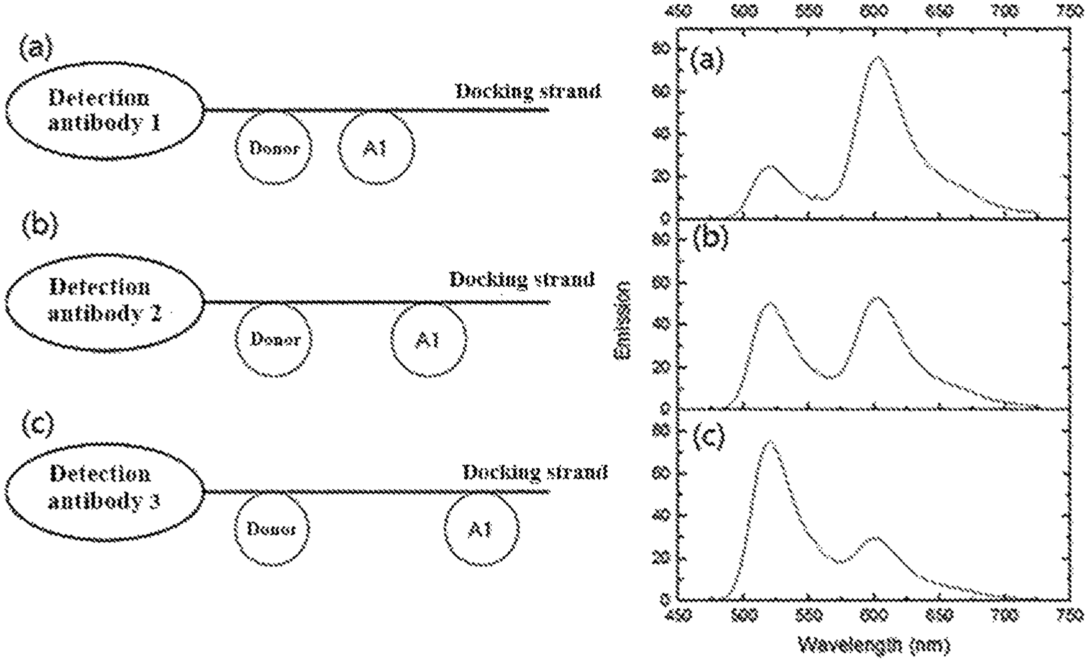

[Fig. 33]
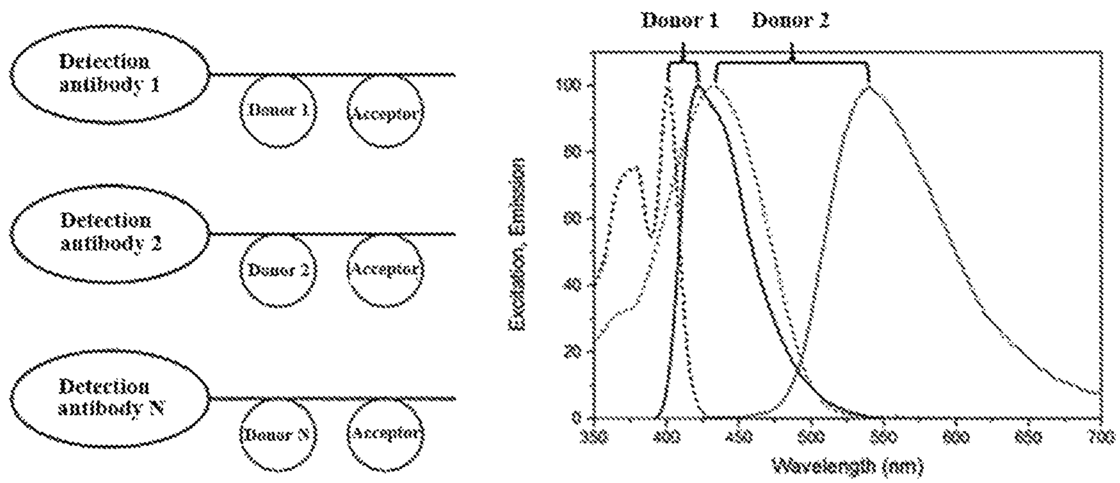
[Fig. 34a]
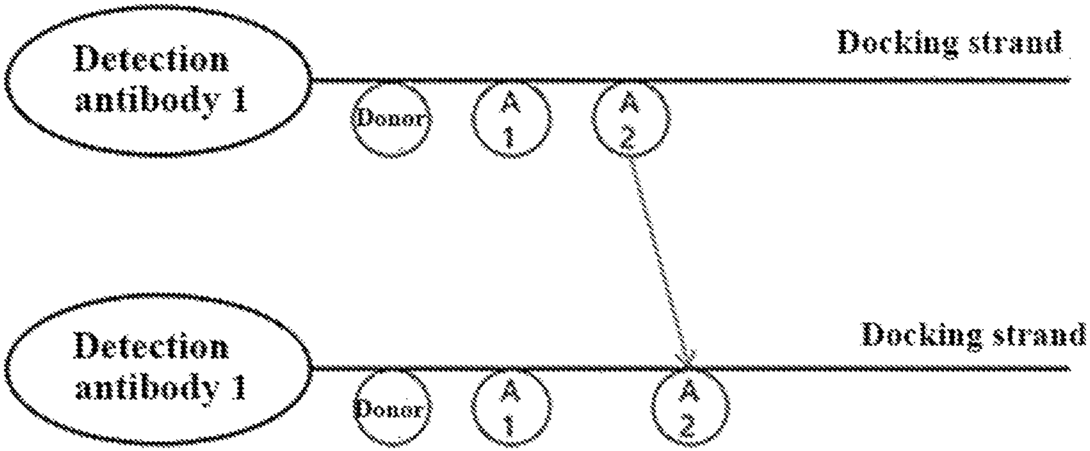
[Fig. 34b]
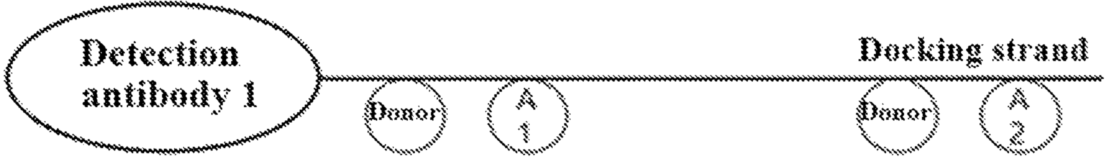

[Fig. 34c]
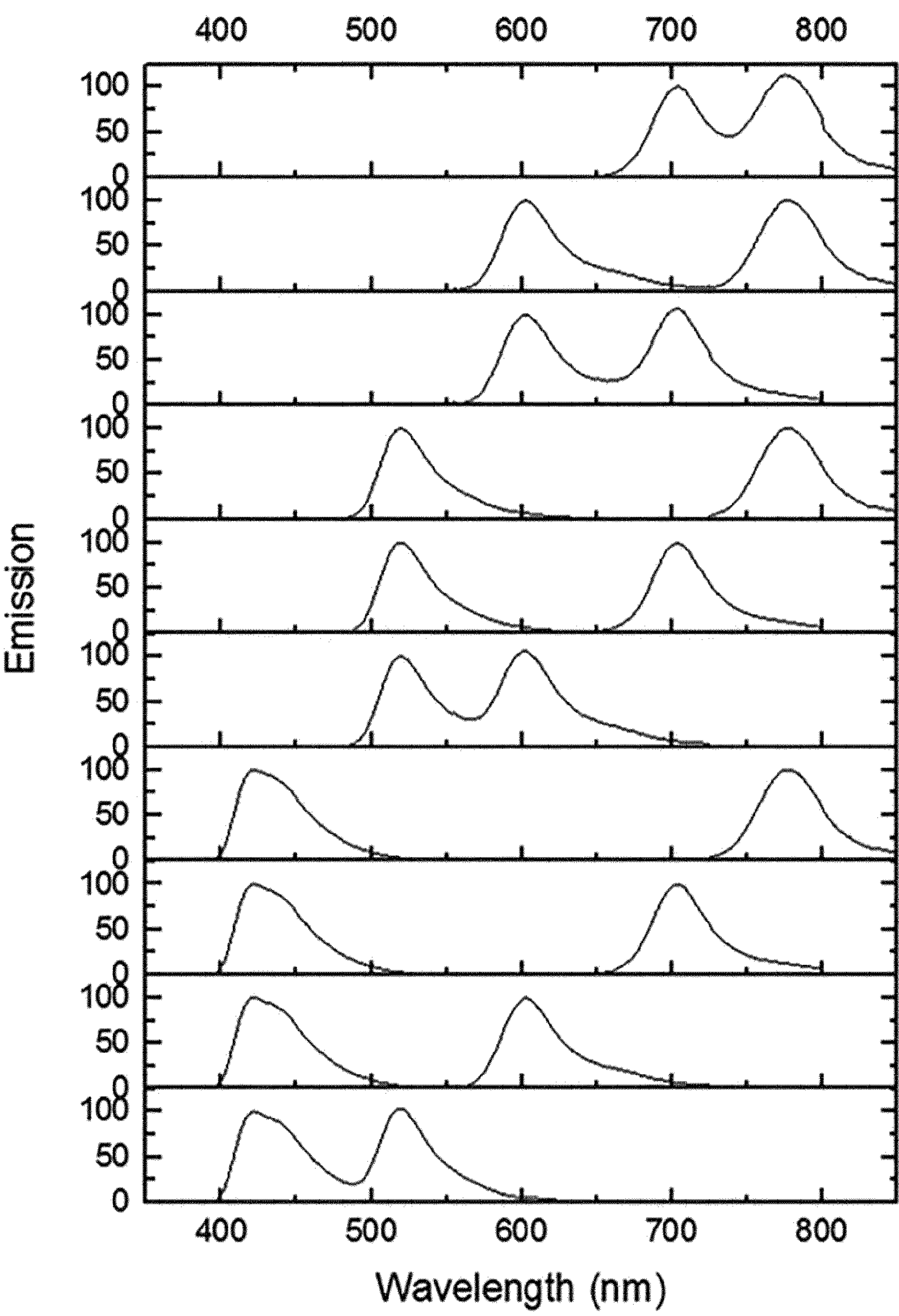

[Fig. 35a]
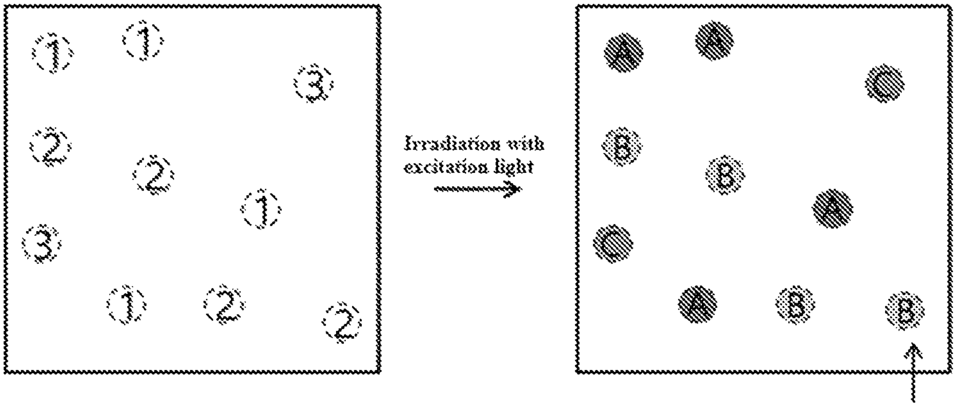
[Fig. 35b]
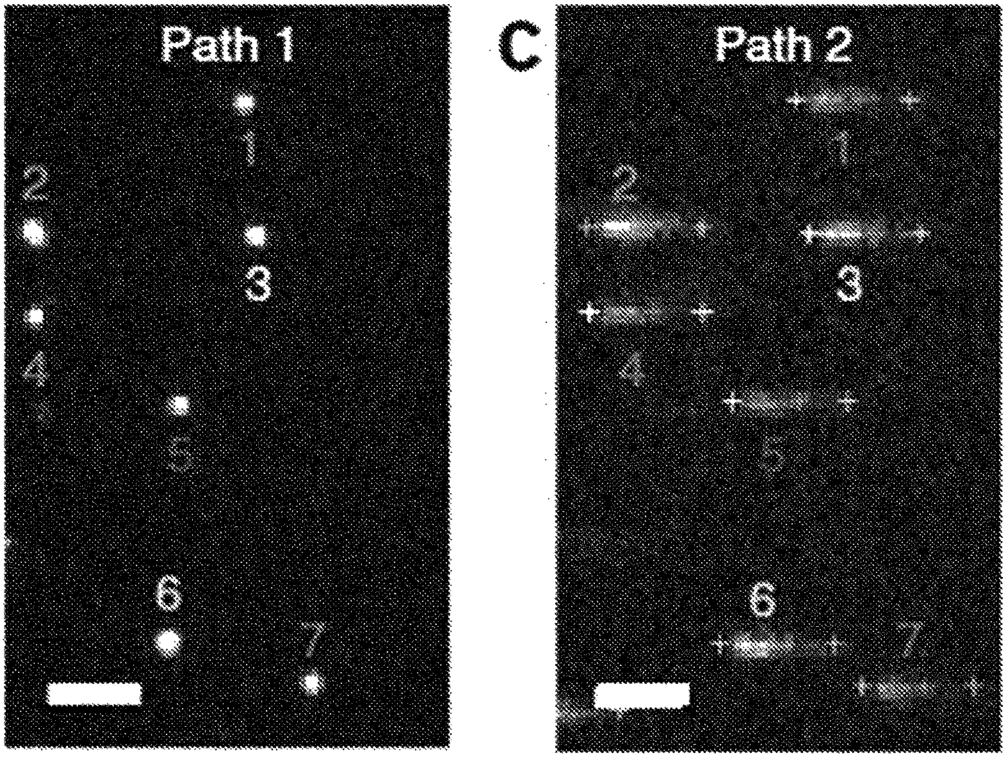

[Fig. 36a]
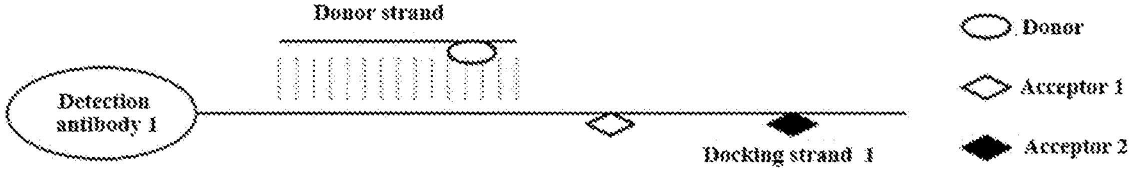
[Fig. 36b]
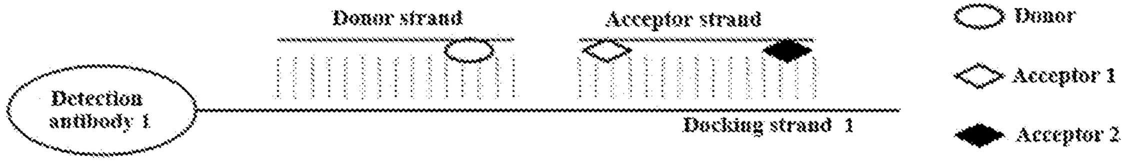
[Fig. 37]
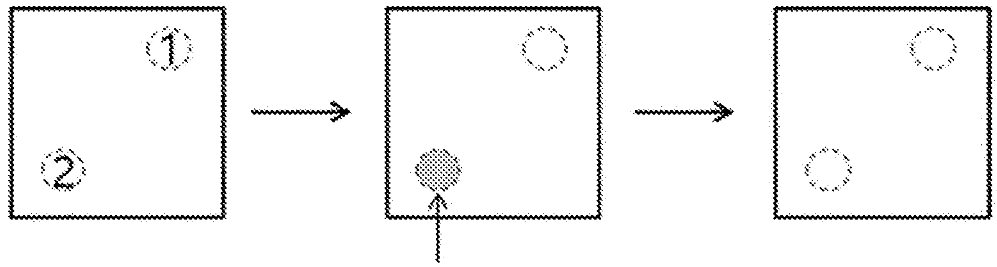
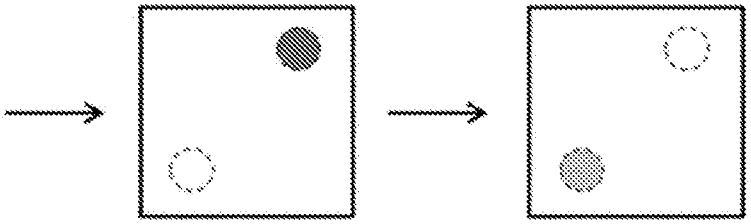

[Fig. 38a]
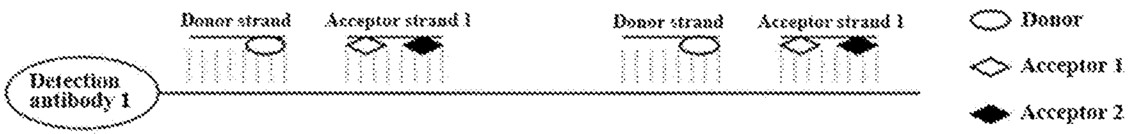
[Fig. 38b]
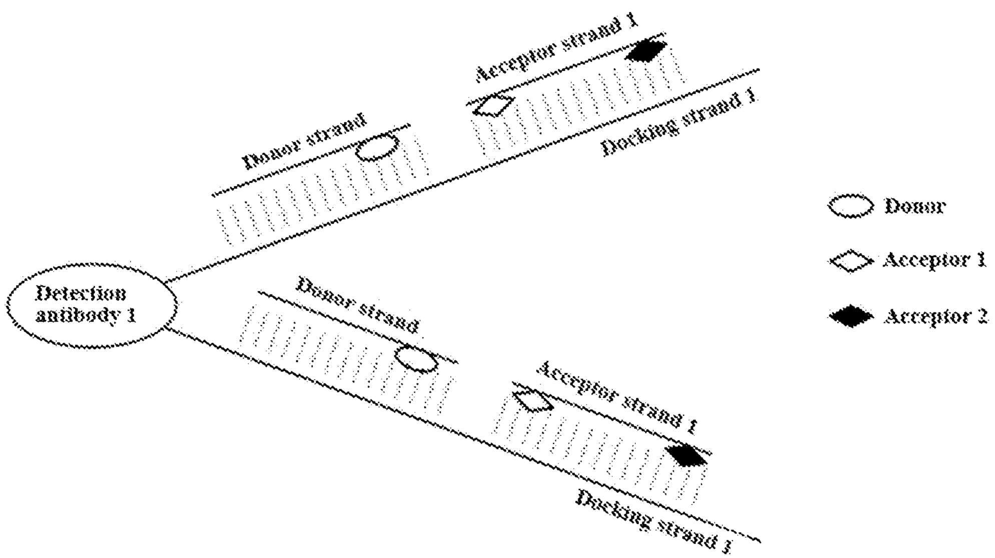
[Fig. 39]
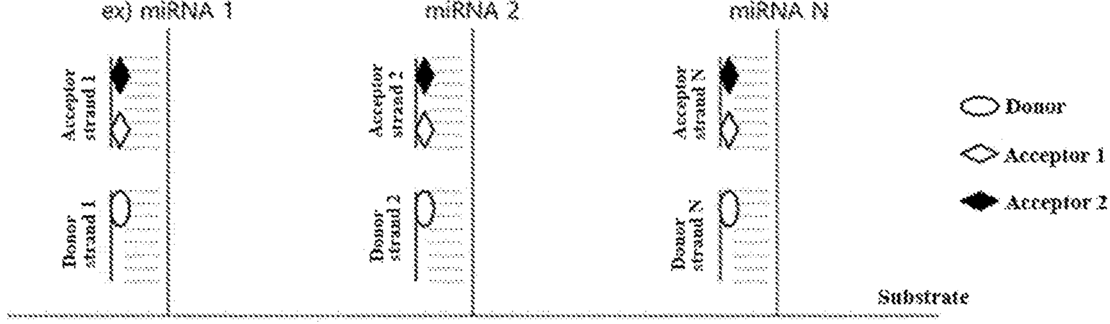

METHODS AND KITS FOR DETECTING TARGET SUBSTANCES

CROSS-REFERENCE TO RELATED APPLICATIONS

This application is the U.S. National Phase under 35 U.S.C. § 371 of International Application No. PCT/KR2019/011003 filed on Aug. 28, 2019, which in turn claims the benefit of Korean Applications No. 10-2018-0101453 filed on Aug. 28, 2018, No. 10-2018-0123312 filed on Oct. 16, 2018, and No. 10-2018-0123313 filed on Oct. 16, 2018, the disclosures of which are incorporated by reference into the present application.

SEQUENCE LISTING

A SEQUENCE LISTING is submitted in a file named PUS200065_ST25.TXT via EFS Web and is hereby incorporated by reference in its entirety. Said file was created on Nov. 3, 2020 and is 974 bytes in size.

TECHNICAL FIELD

The present disclosure relates generally to methods and kits for detecting target substances, and more specifically to methods and kits for multiplexed detection of target substances with very high sensitivity.

BACKGROUND ART

Biomarkers refer to biological markers that can indicate biological state or condition, such as proteins, DNA, RNA, metabolites, etc. Normal or pathological states of organisms can be determined and responses to drugs can be objectively measured based on the detection of biomarkers present in specific samples from living organisms. Biomarker detection has recently received attention as an effective approach to diagnose cancer and other incurable diseases such as cardiac disease, stroke, and dementia in the medical community.

Conventional techniques for biomarker detection are mainly based on ELISA and require biological samples in an amount above a predetermined level in proportion to their sensitivity in the range of at most several to several tens of pg/ml.

According to most of the ELISA-based techniques, when biomarkers are used to determine whether tumors grow or not, each of the biomarkers is identified by each examination. Thus, the examination is repeated several times. However, when tumors grow, not only one level of one biomarker varies, but the levels of two or more biomarkers vary. Accordingly, simultaneous detection of several types of biomarkers is required to determine whether tumors grow or not, thus increasing the accuracy in determining whether or not a disease is present.

In the current state of the art, the detection of a number of biomarkers requires a sufficient amount of blood and a sufficient number of detection kits in proportion to the number of the biomarkers. The sampling of a large amount of blood imposes mental and physical burdens on subjects and the use of a large number of detection kits not only creates an economic burden but also brings about difficulty in early diagnosis of diseases. Thus, it is necessary to simultaneously diagnose one or more types of biomarkers.

Therefore, there is a need to develop highly sensitive and multiplexed diagnostic techniques for simultaneous detection of two or more types of biomarkers in very small amounts of biological samples.

PRIOR ART DOCUMENTS (Patent Document 0001) Korean Patent No. 1431062 entitled "Multiple biomarker set for breast cancer diagnosis, method of detecting the same, and diagnosis kit for breast cancer using antibody against the same" (published on Sep. 23, 2013)

(Patent Document 0002) Korean Patent Publication No. 20170096619 entitled "A method and kit for simultaneously detecting multiple diseases based on 3D protein nanoparticle probes" (published on Aug. 24, 2017)

DETAILED DESCRIPTION OF THE INVENTION

Problems to be Solved by the Invention

According to one aspect of the present disclosure, there is provided a method for detecting target substances including a) introducing a sample containing target substances onto a substrate, b) allowing detection probes conjugated with docking strands to specifically bind to the target substances, c) introducing one or more separate strands capable of complementary binding to the docking strands, either the docking strands or the separate strands, or both, are labeled with at least one donor fluorescent substance and at least one acceptor fluorescent substance, and d) measuring fluorescence signals generated by the FRET between the donor fluorescent substance and the acceptor fluorescent substance to identify the target substances.

According to a further aspect of the present disclosure, there is provided a method for detecting target substances including a) introducing a sample containing nucleic acids or nucleic acid analogues as target substances onto a substrate, b) introducing one or more separate strands capable of complementary binding to the strands of the target substances, either the strands of the target substances or the separate strands, or both, are labeled with at least one donor fluorescent substance and at least one acceptor fluorescent substance, and c) measuring fluorescence signals generated by the FRET between the donor fluorescent substance and the acceptor fluorescent substance to identify the target substances.

According to another aspect of the present disclosure, there is provided a method for detecting target substances including a) introducing a sample containing target substances onto a substrate, b) allowing detection probes conjugated with tagged strands to specifically bind to the target substances, c) labeling the tagged strands with one or more types of donor fluorescent substances and one or more types of acceptor fluorescent substances, and d) measuring fluorescence signals generated by the FRET between the donor fluorescent substances and the acceptor fluorescent substances to identify the target substances.

In one embodiment, the peak absorption wavelength of the donor fluorescent substance may be shorter than that of the acceptor fluorescent substance and the peak emission wavelength of the donor fluorescent substance may be shorter than that of the acceptor fluorescent substance.

In one embodiment, the extinction coefficient of the donor fluorescent substance at a wavelength of light exciting the donor fluorescent substance may be at least 3 times higher than that of the acceptor fluorescent substance.

In one embodiment, the Förster radius between the donor fluorescent substance and the acceptor fluorescent substance is at least 0.208 nm.

In one embodiment, the donor fluorescent substance and the acceptor fluorescent substance may be labeled on the docking strands or the separate strands via linkers.

In one embodiment, the linkers may be 10 nm or less in length.

In one embodiment, the method may further include controlling the wavelength of an optical filter such that the signal-to-noise ratio of the fluorescence signals is at least 2.

In one embodiment, the separate strands may include one or more types of donor strands labeled with one or more types of donor fluorescent substances and one or more types of acceptor strands labeled with one or more types of acceptor fluorescent substances.

In one embodiment, the target substances may be of two or more types and one or more of the donor strands or the acceptor strands may have different sequences depending on the types of the target substances or may be labeled with fluorescent substances of different types or at different sites.

In one embodiment, the method may further include removing the donor strands and/or the acceptor strands after identification of the target substances and repeating step d) using donor strands and/or acceptor strands different from the removed donor strands and/or acceptor strands to identify the other target substances.

In one embodiment, when the donor strands and the acceptor strands bind simultaneously or sequentially to the docking strands, the gap between the donor strands and the acceptor strands may be smaller than the persistence length of the docking strands.

In one embodiment, the method may further include controlling the concentration of the donor strands or the acceptor strands such that the time it takes for the donor strands or the acceptor strands to bind to the docking strands is 10 minutes or less while maintaining the signal-to-noise ratio of the fluorescence signals at 2 or more. In this embodiment, the concentration of the donor strands or the acceptor strands may be from 10 nM to 10 μM.

In one embodiment, when the docking strands or the acceptor strands are nucleic acids, the number of the bases of the acceptor strands complementary to the docking strands may be at least 8. In this embodiment, the number of the bases of the donor strands complementary to the docking strands may be from 6 to 12.

In one embodiment, when the docking strands or the acceptor strands are nucleic acid analogues, the number of the bases of the acceptor strands complementary to the docking strands may be at least 5. In this embodiment, the number of the bases of the donor strands complementary to the docking strands may be from 3 to 9.

In one embodiment, the acceptor strands or the docking strands may be labeled with two or more types of fluorescent substances that form FRET pairs.

In one embodiment, the separate strands may include one or more types of donor strands labeled with one or more types of donor fluorescent substances and the docking strands may include one or more types of acceptor fluorescent substances.

In one embodiment, the separate strands comprise one or more types of acceptor strands labeled with one or more types of acceptor fluorescent substances and the docking strands comprise one or more types of donor fluorescent substances.

In one embodiment, the tagged strands may include two or more FRET pairs.

In one embodiment, the fluorescence signal generated by the FRET may be measured by the FRET efficiency defined by the following equation:

FRET efficiency=(Intensity of light from acceptor)/(Sum of intensity of light from donor and intensity of light from acceptor)

In one embodiment, the measurement of the FRET efficiency may include measuring the brightness values of light from the donors or the acceptors before and after photobleaching.

In one embodiment, the gaps between the FRET pairs may be controlled so as not to affect the FRET efficiency of each FRET pair. The gaps between the FRET pairs may be at least 5 nm.

In one embodiment, two or more types of target substances may be simultaneously identified by determining the difference between the FRET efficiencies distinguished depending on the distances between the fluorescent substances.

In one embodiment, two or more types of target substances may be simultaneously identified by determining the difference between the emission spectra by the FRET between the different types of fluorescent substances.

In one embodiment, the method may further include determining the concentrations of the target substances in the sample from the numbers of the target substances per unit area of a region where the fluorescence signals are imaged.

According to another aspect of the present disclosure, there is provided a kit for detecting target substances including one or more types of detection probes specifically binding to target substances and conjugated with docking strands wherein the docking strands include one or more types of donor fluorescent substances and one or more types of acceptor fluorescent substances and light is emitted by the FRET between the donor fluorescent substances and the acceptor fluorescent substances when the donor fluorescent substances are excited.

In one embodiment, the tagged strands may include two or more FRET pairs.

According to another aspect of the present disclosure, there is provided a kit for detecting target substances including a) one or more types of detection probes specifically binding to target substances and conjugated with docking strands and b) one or more separate strands complementarily binding to the docking strands wherein either the docking strands or the separate strands, or both, are labeled with at least one donor fluorescent substance and at least one acceptor fluorescent substance and light is emitted by the FRET between the donor fluorescent substance and the acceptor fluorescent substance when the donor fluorescent substance is excited.

According to another aspect of the present disclosure, there is provided a kit for detecting target substances including one or more separate strands complementarily binding to the strands of nucleic acids or nucleic acid analogues as target substances wherein the separate strands include donor strands labeled with at least one donor fluorescent substance and acceptor strands labeled with at least one acceptor fluorescent substance and light is emitted by the FRET between the donor fluorescent substance and the acceptor fluorescent substance when the donor fluorescent substance is excited.

According to yet another aspect of the present disclosure, there is provided a kit for detecting target substances including one or more types of detection probes specifically binding to target substances and conjugated with tagged strands wherein the tagged strands include one or more types of donor fluorescent substances and one or more types of acceptor fluorescent substances and light is emitted by the FRET between the donor fluorescent substances and the acceptor fluorescent substances when the donor fluorescent substances are excited.

In one embodiment, the kit may further include a substrate that can capture the target substances. One or more types of capture probes may be immobilized onto the substrate to capture the target substances. The capture probes may be conjugated with the tagged strands.

In one embodiment, the kit may further include bridge strands complementarily binding to the tagged strands of the detection probes and the tagged strands of the capture probes to form FRET pairs.

BRIEF DESCRIPTION OF THE DRAWINGS

FIG. 1*a*, FIG. 1*b*, FIG. 1*c*, FIG. 1*d*, FIG. 1*e*, FIG. 1*f*, FIG. 1*g*, FIG. 1*h*, FIG. 1*i*, FIG. 1*j* and FIG. 1*k* show the principle and characterization of FRET-PAINT.

FIG. 2*a*, FIG. 2*b*, FIG. 2*c*, FIG. 2*d* and FIG. 2*e* compare the imaging speeds of DNA-PAINT and FRET-PAINT.

FIG. 3*a*, FIG. 3*b*, FIG. 3*c*, FIG. 3*d*, FIG. 3*e*, FIG. 3*f*, FIG. 3*g* and FIG. 3*h* show multiplexed capability of FRET-PAINT.

FIG. 4*a*, FIG. 4*b* and FIG. 4*c* show the quantification of biomarkers at various concentrations.

FIG. 5 shows overlapping spectra of a donor and an acceptor.

FIG. 6 shows a donor strand and an acceptor strand bound to a docking strand.

FIG. 7 shows the emission spectra of a donor fluorescent substance (solid line) and an acceptor fluorescent substance (dashed line).

FIG. 8*a* shows an acceptor fluorescence signal taken with a camera.

FIG. 8*b* compares the intensity of a signal with the intensity of noise.

FIG. 9 schematically shows a kit for simultaneous detection of multiple biomarkers according to one embodiment of the present disclosure.

FIG. 10 schematically shows donors and an acceptor labeled on a tagged strand in accordance with one embodiment of the present disclosure.

FIG. 11 shows an imaging process using a single-molecule microscope in accordance with one embodiment of the present disclosure.

FIG. 12 shows the measurement of FRET efficiencies of donors and an acceptor in accordance with one embodiment of the present disclosure.

FIG. 13 shows a tagged strand labeled with two or more donor-acceptor FRET pairs in accordance with one embodiment of the present disclosure.

FIG. 14*a*, FIG. 14*b* and FIG. 14*c* show combinations of donors and acceptors in two or more donor-acceptor FRET pairs in accordance with one embodiment of the present disclosure.

FIG. 15 schematically shows the detection of different types of biomarkers in accordance with one embodiment of the present disclosure.

FIG. 16 schematically shows a kit for simultaneous detection of multiple biomarkers according to one embodiment of the present disclosure.

FIG. 17 schematically shows a kit for simultaneous detection of multiple biomarkers according to one embodiment of the present disclosure.

FIG. 18 schematically shows a kit for simultaneous detection of multiple biomarkers according to one embodiment of the present disclosure.

FIG. 19, FIG. 20 and FIG. 21 schematically show kits for simultaneous detection of multiple biomarkers according to various embodiment of the present disclosure.

FIG. 22 schematically shows a kit for simultaneous detection of N types of biomarkers according to one embodiment of the present disclosure.

FIG. 23 schematically shows a kit for simultaneous detection of N types of biomarkers according to one embodiment of the present disclosure.

FIG. 24 schematically shows a kit for simultaneous detection of multiple biomarkers according to one embodiment of the present disclosure.

FIG. 25 schematically shows a kit for simultaneous detection of multiple biomarkers according to one embodiment of the present disclosure.

FIG. 26 schematically shows a kit for simultaneous detection of biomarkers according to one embodiment of the present disclosure.

FIG. 27 schematically shows a kit for detection of microRNAs according to one embodiment of the present disclosure.

FIG. 28 shows absorption and emission spectra in accordance with one embodiment of the present disclosure.

FIG. 29 schematically shows the principle of simultaneous detection of multiple biomarkers according to one embodiment of the present disclosure.

FIG. 30*a*. FIG. 30*b* and FIG. 30*c* show fluorescence images recorded at different concentrations of donor strands in accordance with one embodiment of the present disclosure.

FIG. 31 exemplarily shows a kit for simultaneous detection of multiple biomarkers according to one embodiment of the present disclosure.

FIG. 32 shows emission spectra depending on the distance between donors and acceptors.

FIG. 33 exemplarily shows a kit for simultaneous detection of multiple biomarkers according to one embodiment of the present disclosure.

FIG. 34*a*, FIG. 34*b* and FIG. 34*c* show emission spectra of docking strands labeled with two or more types of acceptors.

FIG. 35*a* and FIG. 35*b* exemplarily show a method for simultaneous detection of multiple biomarkers according to one embodiment of the present disclosure.

FIG. 36*a* and FIG. 36*b* exemplarily show kits for simultaneous detection of multiple biomarkers according to some embodiments of the present disclosure.

FIG. 37 exemplarily shows a method for identifying the types of biomarkers using a detection kit including a donor strand and an acceptor strand as shown in FIG. 36*b*.

FIG. 38*a* and FIG. 38*b* exemplarily show kits for simultaneous detection of multiple biomarkers according to some embodiments of the present disclosure.

FIG. 39 exemplarily shows a kit for detection of microRNAs according to one embodiment of the present disclosure.

MODE FOR CARRYING OUT THE INVENTION

The terms used herein are briefly defined as follows.

The term "biomarker" as used herein is intended to include all biomaterials that can be used to determine normal or pathological states of organisms.

The term "FRET" as used herein refers to the mechanism of energy transfer by the resonance of two adjacent fluorescent substances. Specifically, it refers to the transfer of energy from a fluorescent substance excited by light to another adjacent fluorescent substance and is intended to include general meanings of FRET that are recognized by those skilled in the art.

The term "FRET efficiency" as used herein refers to the value of energy transferred from a fluorescent substance excited by light to another adjacent fluorescent substance. The FRET efficiency varies depending on the distance between the fluorescent substances. This term is intended to include general meanings of FRET efficiency that are recognized by those skilled in the art.

The term "donor" as used herein refers to a fluorescent substance that transfers energy when excited by light. When two or more fluorescent substances are adjacent to each other, the fluorescent substance that absorbs or emits light of a relatively short wavelength acts as a donor.

The term "acceptor" as used herein refers to a fluorescent substance that receives energy transferred from an excited donor. When two or more fluorescent substances are adjacent to each other, the fluorescent substance that absorbs or emits light of a relatively long wavelength acts as an acceptor.

The term "strand" as used herein refers to a chain of a biopolymer or a chain of a polymer that simulates a biopolymer. The biopolymer may have a single- or double-stranded structure and is intended to include nucleic acids, nucleic acid analogues, polypeptides, and carbohydrates. The nucleic acids include deoxyribonucleic acid (DNA) and ribonucleic acid (RNA). The nucleic acid analogues include peptide nucleic acid (PNA), locked nucleic acids (LNA), morpholino nucleic acid (MNA), glycol nucleic acid (GNA), and threose nucleic acid (TNA).

Various embodiments will now be described in detail with reference to the accompanying drawings. However, modifications can be made to these embodiments and therefore the scope of the present application is not limited or restricted by the embodiments. It is to be appreciated that all changes, equivalents, and substitutes are encompassed within the scope of the appended claims. The terms as used herein are merely for illustrative purposes and are not to be construed as limitations. As used herein, the singular forms "a", "an", and "the" are intended to include the plural forms as well, unless the context clearly indicates otherwise. It will be further understood that the terms "comprises", "comprising", "includes", "including", "has", and/or "having" specify the presence of stated features, integers, steps, operations, elements, components, and/or combinations thereof but do not preclude the presence or addition of one or more other features, integers, steps, operations, elements, components, and/or combinations thereof.

Unless otherwise defined, all terms used herein, including technical or scientific terms, have the same meanings as those generally understood by those with ordinary knowledge in the field of art to which the present disclosure belongs. Such terms as those defined in a generally used dictionary are to be interpreted to have the meanings equal to the contextual meanings in the relevant field of art, and are not to be interpreted to have ideal or excessively formal meanings unless clearly defined in the present application.

In the description of various embodiments with reference to the accompanying drawings, repeated explanation of the same elements is omitted unless otherwise stated.

Recent developments in single-molecule fluorescence microscopy have allowed for observation of individual molecules. When applied to biomarker detection, single-molecule fluorescence microscopy has a sensitivity in the fg/ml range, which is approximately 1000 times higher than that of existing fluorescence imaging techniques (Nature 473, 484-488, 2011). According to a general fluorescence imaging technique, fluorescent substances are immobilized onto molecules to be observed such that different types of biomarkers are distinguished using fluorescence signals. Although the different types of biomarkers are distinguished based on the different colors of the fluorescent substances, only 3-4 types of the fluorescent substances can be distinguished and observed with general image sensors. Consequently, the use of single-molecule fluorescence microscopy, whose sensitivity is in the fg/ml range corresponding to approximately 1000 times that of existing techniques, enables the detection of only 3-4 types of biomarkers.

The application of DNA-PAINT technology (Nature Methods 11, 313-318, 2014) to single-molecule fluorescence microscopy allows for simultaneous analysis of a variety of biomarkers while maintaining the high sensitivity of the single-molecule fluorescence microscopy. According to this convergence technology, detection antibodies conjugated with docking strands other than fluorescent substances are allowed to bind to analyte biomarkers, fluorescent substances are labeled on imager strands that are attached to the docking strands for a while (several seconds) and detached from the docking strands, and fluorescence signals generated when the imager strands bind to the docking strands are detected. In this way, many types of biomarkers can be detected with single-color fluorescent substances while maintaining high sensitivity.

However, when DNA-PAINT technology is used, high background noise is generated because all imager strands emit fluorescence signals irrespective of whether they are bound to docking strands or not. Thus, the concentration of the imager strands is limited to several nM to several tens of nM, disadvantageously resulting in a low detection rate.

One embodiment of the present disclosure provides a method for simultaneous detection of multiple target substances by FRET-PAINT while maintaining high sensitivity of single-molecule fluorescence microscopy. FRET-PAINT is a variant of DNA-PAINT technology based on fluorescence resonance energy transfer (FRET). FRET is a phenomenon in which the energy of an initially excited donor is transferred to an acceptor. Generally, the donor material emits light of a short wavelength compared to the acceptor material. The emission wavelength spectrally overlaps the absorption wavelength of the acceptor. The energy transfer rate and efficiency depend on the degree of overlap between the emission wavelength of the donor and the absorption wavelength of the acceptor, the quantum efficiency of the donor, the relative arrangement of transition dipoles of the donor and the acceptor, and the distance between the donor and the acceptor.

For example, according to the FRET-PAINT technique, the docking strand has two DNA binding sites: one for a donor strand and the other for an acceptor strand. For single-molecule localization, FRET signal of the acceptor is used. Since the acceptor is not directly excited but by FRET, tens to hundreds of times higher imager (donor and acceptor) concentrations could be used, demonstrating tens to hundreds of times higher imaging speed of FRET-PAINT compared to DNA-PAINT.

One aspect of the present disclosure provides a method for detecting target substances. The method includes a) introducing a sample containing target substances onto a substrate, b) allowing detection probes conjugated with docking strands to specifically bind to the target substances, c) introducing one or more separate strands capable of complementary binding to the docking strands into the docking strands, either the docking strands or the separate strands, or both, are labeled with at least one donor fluorescent substance and at least one acceptor fluorescent substance, and d) measuring all or some of the emission spectra by the FRET between the donor fluorescent substance and the acceptor fluorescent substance to identify the target substances.

The individual steps of the method are described below.

First, in step a), a sample containing target substances is introduced onto a substrate. The substrate provides areas for capturing and observing the target substances. The structure of the substrate is not limited. For example, the substrate may be planar, spherical or rod-like in structure. Alternatively, the substrate may be irregularly shaped. The material for the substrate may be, for example, glass, quartz or plastic. The substrate may be slide glass or a coverslip. Preferably, the substrate is a #1 or #1.5 coverslip.

The sample is not limited to a particular kind as long as it contains target substances. The sample is isolated from an animal or human individual suspected of having a disease and can be selected from the group consisting of, but not particularly limited to, tissue, blood, serum, plasma, saliva, mucus, and urine.

Analytes of interest can be used without particular limitation as the target substances. For example, the target substances may be metals (Ca, Mg, Pb, etc.), metal ions or biomaterials. The biomaterials may be biomarkers, blood, plasma, serum, body fluids, proteins, peptides, nucleic acids, bacteria, viruses, endoplasmic reticulum, miRNAs, exosomes, and circulating tumor cells. Preferably, the target substances are biomarkers.

The present disclosure can be used to observe cells, tissues, organs, and other biological samples. Particularly, the present disclosure enables the detection of many types of biomaterials by a single examination for rapid and early disease diagnosis. Therefore, the present disclosure is very suitable for use in the detection of biomarkers.

The biomarkers are not particularly limited. For example, the biomarkers may be those that are usually used in the scientific and medical fields, including measurement or evaluation of biological treatment processes, pathogenic processes, and pharmacological processes for therapeutic applications.

The biomarkers may be polypeptides, peptides, nucleic acids, proteins or metabolites that can be detected from body fluids, for example, blood, saliva, and urine. Specifically, the biomarkers may be alpha fetoprotein (AFP), CA15-3, CA27-29, CA19-9, CA-125, calcitonin, calretinin, carcinoembryonic antigen (CEA), CD34, CD99, MIC-2, CD117, chromogranin, various types of cytokeratins (TPA, TPS, Cyfra21-1), desmin, epithelial membrane antigen (EMA), Factor VIII, CD31, FL1, glial fibrillary acidic protein (GFAP), gross cystic disease fluid protein (GCDFP-15), HMB-45, human chorionic gonadotropin (hCG), immunoglobulin, inhibin, keratin, various types of keratins, lymphocyte marker, MART-1 (Melan-A), Myo DI, muscle-specific actin (MSA), neurofilament, neuron-specific enolase (NSE), placental alkaline phosphatase (PLAP), prostate-specific antigen (PSA), PTPRC (CD45), S100 protein, smooth muscle actin (SMA), synaptophysin, thymidine kinase (TK), thyroglobulin (Tg), thyroid transcription factor-1 (TTF-1), M2-PK, vimentin, interleukin, CD24, CD40, integrin, cystatin, interferon, tumor necrosis factor (TNF), MCP, VEGF, GLP, ICA, HLA-DR, ICAM, EGFR, FGF, BRAF, GFEB, FRS, LZTS, CCN, mucin, lectin, apolipoprotein, tyrosine, neural cell adhesion molecule-like protein, fibronectin, glucose, uric acid, carbonic anhydrase or cholesterol.

The sample may be diluted with a biomarker-free solution. The concentrations of the biomarkers in the sample may greatly vary from fg/ml to mg/ml depending on the biomarker types. Preferably, the sample is diluted in various ratios such that proper numbers of the biomarker molecules are detected by an image sensor. The same sample is preferably diluted in different ratios, most preferably in weight ratios of 1:10 to 1000.

The target substances can be directly attached to the substrate. Alternatively, the target substances may be introduced onto the substrate via capture probes attached to the substrate. The substrate may be coated with a suitable polymer such that undesired substances such as antigens, antibodies, and fluorescent substances are not attached to the substrate surface. The polymer may be, for example, polyethylene glycol (PEG) or acrylamide.

The capture probes specifically bind to the target substances to immobilize the target substances onto the substrate. The capture probes may be antibodies or aptamers. For example, the capture probes may be capture antibodies capable of specific binding to biomarkers to capture the biomarkers. The capture antibodies can be attached to the substrate by introducing biotin into the surface of the capture antibodies and introducing avidin, neutravidin or streptavidin capable of binding to biotin onto the substrate.

For example, the analyte biomarkers may be directly attached to the substrate surface without the need to use capture antibodies for rapid and convenient measurement. Alternatively, the biomarker molecules may be attached to capture antibodies immobilized onto the substrate surface through the antigen-antibody reaction for higher accuracy of measurement results.

In the case where the biomarkers are directly attached to the substrate surface, for example, a coverslip is coated with a bead solution and cells corresponding to the sample are cultured and immobilized onto the substrate surface. Capture antibodies may be attached to the substrate by diluting the capture antibodies with a 0.06 M carbonate or bicarbonate buffer solution at pH 9.5 and bringing the dilution into contact with the substrate at a predetermined temperature for a predetermined time. Then, the substrate is treated with a raw or processed sample. The capture antibodies adsorbed to the substrate form complexes with the biomarkers in the sample. The complexes are washed with a buffer such as Tween 20 or a cleaning agent such as distilled water to remove non-specifically bound antibodies or contaminants.

In step b), detection probes conjugated with docking strands are allowed to specifically bind to the target substances. The detection probes may be antibodies or aptamers. For example, the docking strands may be tagged on detection antibodies capable of specific binding to the analyte biomarkers.

Specifically, the term “antibodies” herein used to refer to the capture antibodies and the detection antibodies may include monoclonal antibodies (including full-length monoclonal antibodies), polyclonal antibodies, multispecific antibodies (e.g., bispecific antibodies), and antibody fragments (e.g., variable regions and other regions of antibodies that exhibit desired bioactivities). The antibodies are intended to include both monoclonal and polyclonal antibodies, chimeric antibodies, humanized antibodies, and human antibodies. Preferably, the antibodies include Fab, F (ab) 2, Fab', F(ab') 2, Fv, diabodies, nanobodies, and scFv. More preferably, the antibodies are scFv, Fab, nanobodies or immunoglobulin molecules.

The docking strands can be attached to antibodies or aptamers as the detection probes by general methods known in the art for binding protein molecules to nucleic acid molecules, for example, based on a binding reaction between nucleic acid molecules and protein molecules using a compound having two different reactive groups, for example, succinimidyl 4-(N-maleimidomethyl)cyclohexane-1-carboxylate (SMCC) in which the NHS-ester group reacts with an amine and the maleimide group reacts with a thiol. The docking strands can be attached to the detection antibodies by reacting the thiol group-containing docking strands with SMCC and reacting the resulting products with the amine groups at the N-termini of the detection antibodies or the amine groups of lysine.

For accurate measurement, the detection antibodies are primary antibodies and the docking strands are attached to the primary antibodies. For rapid measurement, the detection antibodies are a combination of primary antibodies and secondary antibodies and the docking strands are attached to the secondary antibodies.

The primary antibodies may be immunoglobulin molecules that specifically bind to biomarkers and their type is not limited. In the Examples section that follows, anti-tubulin antibodies, and anti-Tom20 antibodies were used as the primary antibodies.

The secondary antibodies refer to antibodies that bind to the primary antibodies bound to biomarkers and their type is not limited. In the Examples section that follows, donkey anti-rabbit IgG antibodies or donkey anti-rat IgG antibodies were used as the secondary antibodies.

In step c), one or more separate strands capable of complementary binding to the docking strands are introduced into the docking strands.

Either the docking strands or the separate strands, or both, are labeled with at least one donor fluorescent substance and at least one acceptor fluorescent substance.

The separate strands can complementarily bind to the docking strands and can be classified into donor strands, acceptor strands, and FRET strands depending on the types of the fluorescent substances attached to the strands. The donor strands may be labeled with at least one fluorescent substance acting as a donor and the acceptor strands may be labeled with at least one fluorescent substance acting as an acceptor that can be excited by energy transferred from the donor fluorescent substance. The FRET strands may include both donor and acceptor fluorescent substances that form FRET pairs.

In one embodiment, the separate strands may include one or more types of donor strands labeled with one or more types of donor fluorescent substances and one or more types of acceptor strands labeled with one or more types of acceptor fluorescent substances.

FRET is a phenomenon in which when two different types of fluorescent substances are located very close to each other, the energy of one fluorescent substance (donor) is transferred to the other fluorescent substance (acceptor). Based on this phenomenon, a target substance can be effectively detected. In order for the acceptor to emit light, the acceptor should receive energy transferred from the donor. This energy transfer occurs only when the donor strand and the acceptor strand simultaneously bind to the docking strand. Thus, a fluorescence signal from the acceptor reflects the location of the target substance.

FIG. 1*b* shows the principle of detection of a target substance based on FRET-PAINT technique using the donor strand and the acceptor strand shown in FIG. 1*a*. When FRET occurs, energy is transferred from the donor to the acceptor, with the result that the donor becomes dark while the acceptor emits light and appears bright.

According to this technique, imager strands of DNA-PAINT are divided into donor strands and acceptor strands. Fluorescence signals from the donors observed when fluorescent substances labeled on the donor strands are excited by light at Mex are removed by an optical filter, and as a result, fluorescence signals from the acceptors can be observed. That is, all donor fluorescent substances emit light, which is removed by an optical filter, and acceptor fluorescent substances are not directly excited by light at hex, resulting in very low background noise. Since background noise caused by the donors is negligibly low, unlike in DNA-PAINT, the concentration of the donor strands can be increased to as high as hundreds of nM, achieving rapid measurement by several hundred times.

In one embodiment, the separate strands include one or more types of acceptor strands labeled with one or more types of acceptor fluorescent substances and the docking strands may include one or more types of donor fluorescent substances. Preferably, quantum dots as fluorescent substances are introduced into the docking strands. In this case, no photobleaching occurs, unlike when fluorescent proteins, organic fluorophores, etc. are introduced. Accordingly, there is no need to introduce donor strands in order to solve the problem of photobleaching caused by donor fluorescent substances and background noise caused by the use of donor strands is reduced, resulting in a high signal-to-noise ratio. In addition, a simple construction is achieved, which is advantageous from an economic viewpoint, and the analysis process can be simplified.

The strands, including the docking strands and the separate strands, may be nucleic acids, polypeptides or carbohydrates. Preferably, the strands are nucleic acids that the docking strands can complementarily bind to the separate strands, are easy to synthesize, are inexpensive, and provide desired sites to which fluorescent substances are easily attached. The nucleic acids can be selected from the group consisting of DNA, RNA, PNA, LNA, MNA, GNA, and TNA which are capable of complementary binding to the separate strands. The nucleic acids may be single- or double-stranded.

The docking strands are conjugated to the detection probes and the imager strands, the donor strands, and the acceptor strands can complementarily bind to the docking strands. The imager strands are used when the DNA-PAINT technique is employed. The donor strands and the acceptor strands are used when the FRET-PAINT technique is employed.

The imager strands have different sequences depending on the biomarker types. For example, in the case where two imager strands bind to two different types of biomarkers, their sequences are different in at least one base, indicating that the sequences of the imager strands bound to the different types of biomarkers are different irrespective of the number of the biomarker types.

In one embodiment, the donor strands and the acceptor strands have different sequences depending on the biomarker types. For example, the use of N donor strands and N acceptor strands having different sequences is necessary for detecting N different types of biomarkers. That is, the sequences of the donor strands are different in at least one base, the sequences of the acceptor strands binding to the different types of biomarkers are also different in at least one base, and all donor and acceptor strands have different sequences.

In one embodiment, the acceptor strands may have the same sequence as some or all of the biomarkers; and the sequences of the donor strands may be different from those of the acceptor strands and may be different from each other depending on the biomarker types. For example, when it intends to detect two different types of biomarkers, the sequences of donor strands binding to the different biomarkers may be different in at least one base and acceptor strands having the same sequence may be used for detection of the biomarkers.

In one embodiment, the donor strands may have the same sequence as some or all of the biomarkers; and the sequences of the acceptor strands may be different from those of the donor strands and may be different from each other depending on the biomarker types. For example, when it intends to detect two different types of biomarkers, the sequences of acceptor strands binding to the different biomarkers may be different in at least one base and donor strands having the same sequence may be used for detection of the biomarkers.

The docking strands may include sequences complementary to the sequences of the donor strands and the acceptor strands.

The strands may have various structures. For example, the strands may have structures known in the art. Alternatively, functional groups may be introduced into the strands such that the fluorescent substances are attached to the strands. The strands may be previously attached with the fluorescent substances. When functional groups are introduced into the strands, the desired fluorescent substances can be attached to desired sites of the strands. The same or different functional groups may be attached to each strand. The distances between the donors and the acceptors and the FRET efficiency may vary depending on the sites of the strands at which the donors and the acceptors are attached. These characteristics enable multiplexed detection of the target substances.

The fluorescent substances are excited by external energy such as UV, visible or infrared light, electrical energy or thermal energy to convert the energy into light. Examples of the fluorescent substances include organic and inorganic fluorophores. Examples of the organic fluorophores include rhodamine, Alexa Fluor dye, fluorescein, fluorescein isothiocyanate (FITC), 5-carboxy fluorescein (FAM), ATTO dye, BODIPY, CF dye, Cyanine (Cy) dye, DyLight Fluor, and Texas Red. The inorganic fluorophores may be, for example, quantum dots.

The peak wavelength of the emission spectra of the fluorescent substances labeled on the donor strands is shorter than the peak wavelength of the absorption spectra of the fluorescent substances labeled on the acceptor strands.

The intensity of the FRET signal between two fluorescent substances in a donor-acceptor relationship is correlated with the distance between the two fluorescent substances. For example, each DNA strand is a linearly extended arrangement of nucleotides, each of which is made of one of the four different types of bases, including A, T, G, and C, one sugar, and one phosphate. The bases of two strands complementarily bind to each other. A desired functional group or fluorescent substance may be attached to any one of the base, sugar, and phosphate in each nucleotide. Since the distance between the two adjacent bases in the DNA double helix is 0.34 nm, the distance of the FRET pair can be very precisely controlled. When it is desired to label a single-stranded DNA with two different fluorescent substances between which M bases are present, an amine group is tagged on a specific base and a thiol (sulfhydryl; SH) group is tagged on a base at a position that is M bases distant from the specific base. Then, the DNA is allowed to react with fluorescent substance A attached with an NHS-ester group reacting with the amine group and fluorescent substance B attached with a maleimide group reacting with the thiol group to label the FRET pair. The use of different reactive groups enables labeling with three or more fluorescent substances. For example, an aldehyde group is attached to a specific location of DNA and fluorescent substance C attached with a hydrazide group reacting with the aldehyde group is attached to the DNA.

The specific binding reactions between the target substances and the detection or capture probes may proceed by binding based on an immune reaction such as sandwich ELISA or specific aptamer binding.

In subsequent step d), fluorescence signals generated by the FRET between the donor fluorescent substance and the acceptor fluorescent substance are measured to identify the target substances. The fluorescence signals can be measured from all or some of the emission spectra by the FRET. For example, when the target substances are distinguished by the FRET efficiencies, only a portion (mainly a peak) of the spectrum of each fluorescent substance is measured. When the target substances are distinguished by the spectral shapes, all spectra can be measured.

Step d) includes detecting the fluorescence signals generated in step c). The fluorescence signals may be generated when the imager strands bind to the docking strands or the donor and acceptor strands bind simultaneously to the docking strands. Specifically, the fluorescence signals may be generated when the imager strands remain bound to the docking strands for a predetermined time or the donor fluorescent substance labeled on the donor strands is located very close to the acceptor fluorescent substance labeled on the acceptor strands by the docking strands for a predetermined time. The fluorescence signals can be detected using a highly sensitive image sensor (e.g., EMCCD, sCMOS or iCMOS).

In one embodiment, the method may further include removing the donor strands and/or the acceptor strands after identification of the target substances and repeating step d) using donor strands and/or acceptor strands different from the removed donor strands and/or acceptor strands to identify the other target substances. After complete removal of the donor strands and the acceptor strands, combinations of different strands may be used. Alternatively, either the donor strands or the acceptor strands may stably bound to the docking strand and remain unremoved. The unremoved donor strands or acceptor strands are used as common strands and the other unstably bound strands are removed.

The method is based on the use of different sequences of strands for multiplexed detection. Accordingly, N types of targets can be detected by loading donor strands (or acceptor strands or both donor and acceptor strands) complementarily binding to docking strands N times, followed by repeated washing. For example, the multiple biomarkers may be detected by repeating steps c) and d) as many times as the number of the biomarker types. The fluorescence signals generated when the donor and acceptor strands labeled with the fluorescent substances bind to the docking strands are detected. Then, the as-bound strand(s) are removed. The same procedure is repeated using different strand(s) and the resulting fluorescence signals are detected. This procedure is repeated several times, preferably as many times as the number of the biomarker types. For example, the donor strand consisting of 9 bases may have 49 (=262,144) sequences. Since the number of the sequences of the donor strands is larger than the number of all proteins in the human body, the donor and acceptor strands having different sequences are assigned to all biomarkers so that the biomarkers can be measured sequentially.

The FRET reaction between donor and acceptor fluorescent substances can be measured by various techniques.

When a fluorescence signal is generated, it looks much larger than the actual size due to the phenomenon of diffraction. Accordingly, when two target substances are located very close to each other on a substrate and emit fluorescence signals simultaneously, light-emitting regions in the form of spots overlap, making it impossible to accurately measure the fluorescence signals.

In one embodiment, the docking strands may be labeled with the acceptor fluorescent substance or bound with the acceptor strands. In this embodiment, the biomarkers can be detected by measuring the FRET efficiencies or emission spectra of the fluorescence signals generated at the moment when the donor strands bind to the docking strands. The donor strands bind to all docking strands once or more. Accordingly, FRET efficiencies or emission spectra need to be measured whenever the donor strands bind to the docking strands. Thus, a relatively long time (tens of seconds to several minutes) is needed to detect all biomarkers, but two biomarkers can be distinguished although they are very close to each other. When two fluorescent substances very close to each other emit light simultaneously, only one spot whose brightness doubles is observed with a camera, making it impossible to distinguish the FRET efficiencies of the fluorescent substances. In contrast, when two fluorescent substances emit light sequentially at a time interval, it is possible to measure the accurate location and FRET efficiency of each spot, with the result that the two biomarkers can be identified. In addition, several FRET efficiencies in one docking strand can be measured, which is advantageous for multiplexed detection. If fluorescent substances having several FRET efficiencies emit light simultaneously, the FRET efficiencies cannot be determined individually.

In one embodiment, fluorescence signals may be measured after the donors are excited in a state in which the donor and acceptor fluorescent substances are labeled on the docking strands or both the donor and acceptor strands are bound to the docking strands. Since all fluorophores emit light as soon as the donors are excited, fluorescence signals can be measured in a short time. However, when the distance between the fluorophores decreases with increasing concentration of the biomarkers, the light-emitting regions in the form of spots overlap, making it difficult to accurately measure the fluorescence signals. Further, several FRET efficiencies for one biomarker cannot be measured and a reduced number of the biomarkers may be detected. However, since the biomarkers are distinguished by the shapes of the emission spectra, there may be no problems in multiplexed detection of the biomarkers.

A further aspect of the present disclosure provides a kit for detecting target substances including a) one or more types of detection probes specifically binding to target substances and conjugated with docking strands and b) one or more separate strands complementarily binding to the docking strands. Either the docking strands or the separate strands, or both, are labeled with at least one donor fluorescent substance and at least one acceptor fluorescent substance and light is emitted by the FRET between the donor fluorescent substance and the acceptor fluorescent substance when the donor fluorescent substance is excited.

In one embodiment, the kit may further include a substrate on which the target substances can be captured. A suitable coating layer may be introduced onto the substrate or the surface of the substrate may be modified to prevent substances other than the target substances from non-specific binding to the substrate or facilitate attachment of the target substances on the substrate. The target substances can be directly attached on the substrate. Alternatively, the target substances may be introduced by capture with capture probes previously attached to the substrate.

In one embodiment, the kit may include a) one or more types of detection antibodies conjugated with docking strands and b) one or more types of donor strands labeled with fluorescent substances and acceptor strands labeled with fluorescent substances. The kit detects signals generated when the detection antibodies conjugated with the docking strands bind to biomarkers and the docking strands bind to the donor strands and the acceptor strands.

The kit may include i) a substrate, ii) capture antibodies, iii) primary detection antibodies conjugated with docking strands, or primary detection antibodies unconjugated with docking strands and secondary detection antibodies conjugated with docking strands, and iv) donor strands and acceptor strands. Preferably, the kit consists of a substrate, capture antibodies, primary detection antibodies conjugated with docking strands, donor strands, and acceptor strands.

The kit may be an in vitro diagnostic product for detecting biomarkers. For example, the kit may be a research use only (RUO) kit, an investigational use only (IUO) kit or an in vitro diagnostic (IVD) kit.

Another aspect of the present disclosure provides a method for detecting nucleic acids or nucleic acid analogues as the target substances in a sample. The method includes a) introducing a sample containing nucleic acids or nucleic acid analogues as target substances onto a substrate, b) introducing one or more separate strands capable of complementary binding to the strands of the target substances, either the strands of the target substances or the separate strands, or both, are labeled with at least one donor fluorescent substance and at least one acceptor fluorescent substance, and c) measuring fluorescence signals generated by the FRET between the donor fluorescent substance and the acceptor fluorescent substance to identify the target substances.

The use of nucleic acid or nucleic acid analogues as target substances in this aspect avoids the need for docking strands, unlike in the previous aspect. The target substances are preferably RNA, microRNA (miRNA), cell-free (cfDNA) or circulating free DNA or circulating tumor DNA (ctDNA), which can be used to determine normal or pathological states of organisms.

In one embodiment, the method may include a) attaching one or more types of nucleic acids present in a sample from a subject to the surface of a substrate, b) conjugating the nucleic acids with donor strands and acceptor strands, and c) detecting fluorescence signals generated in step b).

In one embodiment, after detection of the fluorescence signals, the as-bound donor strands and the as-bound acceptor strands are removed, different imager strands or different combinations of donor and acceptor strands are conjugated to the nucleic acids, and steps b) and c) are repeated as many times as the number of types of the target nucleic acids.

A description will be given of the individual steps of the method.

In step a), one or more types of nucleic acids present in a sample taken from a subject are attached to the surface of a substrate. The nucleic acids may function as biomarkers to be detected. The nucleic acids are preferably non-coding RNAs. Non-coding RNAs are types of RNAs that lack amino acid codes for specific proteins. Unlike mRNAs that translate gene sequences, non-coding RNAs exist in various forms and can be produced from mRNA by-products or degradation products or through separate transcription processes. Non-coding RNAs are known to play a role in the regulation of chromosomal activity or protein expression. The analyte RNAs are intended to include small RNAs such as miRNAs, snRNAs, snoRNAs, aRNAs, siRNAs, piRNAs, exRNAs, and scaRNAs, but are preferably microRNAs.

microRNAs (miRNAs) are small non-expression RNA molecules consisting of approximately 22 bases. miRNAs are involved in the regulation of gene expression after RNA silencing and transcription. miRNAs are found in numerous biofluids such as blood and urine and their levels vary by various diseases. For these reasons, miRNAs are receiving attention as biomarkers.

Nucleic acids cannot be captured by the antigen-antibody reaction. In the present disclosure, the analyte nucleic acids are attached to the substrate surface by immobilizing capture probes having sequences complementary to portions of the analyte nucleic acids onto a substrate and allowing the nucleic acids to complementarily bind to the capture probes. The sample may be diluted with a nucleic acid free solution. The concentrations of the nucleic acids in the sample may greatly vary depending on the types of the nucleic acids. Accordingly, the sample can be diluted in various ratios such that appropriate numbers of the nucleic acid molecules are detected by an image sensor.

Next, in step b), the nucleic acids are bound with donor strands and acceptor strands. The donor and acceptor strands are designed such that they can complementarily bind to single-stranded portions of the nucleic acids which are not complementarily bound to the capture probes. The capture probes, the donor strands, and the acceptor strands are individually selected from the group consisting of DNA, RNA, PNA, and LNA strands.

In step c), fluorescence signals generated in step b) are detected. The fluorescence signals are generated when the donor strands and the acceptor strands bind simultaneously to single-stranded portions of the nucleic acids which are not complementarily bound to the capture probes. More specifically, the fluorescence signals may be generated when the imager strands remain bound to single-stranded portions of the nucleic acids which are not complementarily bound to the capture probes for a predetermined time or the donor fluorescent substance labeled on the donor strands are located very close to the acceptor fluorescent substance labeled on the acceptor strands by the nucleic acids for a predetermined time. The fluorescence signals can be detected using a highly sensitive image sensor (e.g., EMCCD, sCMOS or iCMOS).

Another aspect of the present disclosure provides a kit for detecting nucleic acids or nucleic acid analogues as target substances in a sample. The kit includes one or more separate strands complementarily binding to the strands of nucleic acids or nucleic acid analogues as target substances. The separate strands include donor strands labeled with at least one donor fluorescent substance and acceptor strands labeled with at least one acceptor fluorescent substance. Light is emitted by the FRET between the donor fluorescent substance and the acceptor fluorescent substance when the donor fluorescent substance is excited.

In one embodiment, the kit includes one or more types of donor strands labeled with a fluorescent substance and one or more types of acceptor strands labeled with a fluorescent substance and detects signals generated when the imager strands or the donor and acceptor strands bind to target substances.

In one embodiment, the kit may further include a substrate on which the nucleic acids can be captured.

In one embodiment, capture probes having a sequence complementary to a portion of the analyte nucleic acids may be immobilized onto the substrate. Alternatively, the substrate may be surface modified such that the capture probes can be attached to the substrate surface.

In the Examples section that follows, FRET-PAINT was found to be advantageous over conventional DNA-PAINT.

In the Examples section that follows, a determination was made as to whether FRET-PAINT can be performed by microscopic examination. To this end, docking strands were immobilized on the surface of the quartz, donor and acceptor strands labeled with a fluorescent substance were injected, and single-molecule images were then recorded, with the result that clear fluorescence intensities were found (see Example 1-1 and FIG. 1*c*).

In the Examples section that follows, the same experiment was conducted using two FRET pairs (Cy3-Cy5 and Alexa488-Cy5). As a result, the Alexa488-Cy5 FRET pair gave the highest fluorescence signal when the gap between donor and acceptor strands was 2 nt, whereas the Cy3-Cy5 FRET pair gave the highest fluorescence signal when the gap between donor and acceptor strands was 6 nt (see Example 1-1 and FIG. 1*d*).

In the Examples section that follows, super-resolution fluorescence images were measured and the signal-to-noise ratios (SNRs) of DNA-PAINT and FRET-PAINT at varying DNA concentrations were compared. As a result, noise occurred in the single-molecule images when the DNA concentration was ≥5 nM for DNA-PAINT and when the DNA concentration was ≥100 nM for FRET-PAINT, demonstrating that the same SNR can be obtained at higher imager concentrations for FRET-PAINT compared to for DNA-PAINT (see Example 1-1 and FIGS. 1*e* to 1*k*).

In the Examples section that follows, cells were immunostained with anti-tubulin antibody conjugated with docking strands, microtubules were observed using DNA-PAINT, and microtubules in the same area were imaged using FRET-PAINT. The imaging speeds of DNA-PAINT and FRET-PAINT were quantified and compared, with the result that images were recorded at a rate of 10 Hz for a total imaging time of 30 minutes for DNA-PAINT and images were recorded at a rate of 10 Hz for a total imaging time of 60 seconds for FRET-PAINT, demonstrating the imaging speed of FRET-PAINT was found to be higher than that of DNA-PAINT (see Example 1-2 and FIGS. 2*a* to 2*e*).

In the Examples section that follows, cells were immunostained with anti-tubulin antibody and anti-Tom20 antibody conjugated with docking strands, treated with donor and acceptor strands sequentially or simultaneously, and images were recorded, with the result that the sequential treatment with the donor and acceptor strands was found to be more effective in multiplexed imaging (see Example 1-3 and FIGS. 3*a* to 3*h*).

In the Examples section that follows, the numbers of molecules found in images were measured at varying biomarker concentrations. As a result, the individual molecules were well distinguished in the range of 10 pg/mg to 400

μg/ml, enabling the measurement of the biomarker concentrations. In contrast, the molecules started to overlap at concentrations above 1000 μg/ml, making it impossible to measure accurate concentrations. After the sample was diluted in an appropriate ratio such that the concentration reached approximately 100 μg/ml, the number of the molecules was measured and divided by the dilution ratio to calculate the biomarker concentration, which exactly coincides with the original one. An accurate measurement was possible in the concentration range of currently widely used biomarkers (several pg/ml to several tens of ng/ml) (see Example 1-4 and FIGS. 4*a* to 4*c*).

As described above, the use of a single-molecule fluorescence microscope and a FRET-PAINT system enables the detection of various biomarkers from a very small amount of biofluid with a 1000-fold higher sensitivity than conventional methods, thus being useful for the early diagnosis of various diseases, including cancer, while solving the problems of conventional diagnostic methods using biomarkers.

For efficient detection of target substances by the methods and kits of the present disclosure, FRET effects between donors and acceptors need to be maximized. To this end, it is preferable to select appropriate donors and acceptors such that the spectra of the donors and the acceptors overlap effectively to induce optimal energy transfer.

FIG. 5 shows the overlapping spectra of a donor and an acceptor.

In one embodiment, the donor and the acceptor may be selected such that the peak absorption wavelength of the donor is shorter than that of the acceptor and the peak emission wavelength of the donor is shorter than that of the acceptor. As a result, energy can be transferred from the donor to the acceptor and only the donor can be selectively excited by excitation light of a particular wavelength because the peak absorption wavelength of the donor is shorter than that of the acceptor. A fluorescence signal from the donor can be removed with a suitable tool such as a dichroic mirror, prism or diffraction grating and a fluorescence signal from the acceptor can be selectively detected because the peak emission wavelength of the donor is shorter than that of the acceptor.

The FRET efficiency (EFRET) between the donor and the acceptor is calculated by Equation 1:

(Equation 1)

$$E_{FRET} = \frac{1}{1 + \left(\frac{R}{R_0}\right)^6}$$

where R is the donor-acceptor distance and $R_0$ (Förster radius) is the donor-acceptor distance at which the FRET efficiency is 0.5 and can be defined by Equation 2:

$$R_0 = \left(8.8 \times 10^{23} \times k^2 \times n^{-4} \times \Phi_D \times J_{DA}\right)^{\frac{1}{6}} \quad \text{(Equation 3)}$$

where κ is the constant representing the influence of dipole orientation, n is the constant representing the refractive index of a medium, $\Phi_D$ is the quantum yield of the donor fluorescent substance and varies depending on the type of the donor fluorescent substance, and $J_{DA}$ is the spectral overlap integral and can be defined by Equation 3:

$$J_{DA} = \int_0^{\infty} \left(\epsilon_A(\lambda) \times F_D(\lambda) \times \lambda^4\right) d\lambda \quad \text{(Equation 3)}$$

where $\varepsilon_A$ is the extinction coefficient of the acceptor fluorescent substance and $F_D$ is the fluorescence emission intensity of the donor fluorescent molecule. $J_{DA}$ varies depending on the spectral overlap between the emission spectrum of the donor fluorescent substance and the absorption spectrum of the acceptor fluorescent substance and, together with ΦD, is thus an important factor determining R0.

For example, the donor and the acceptor may be selected such that the extinction coefficient of the donor at the wavelength of excitation light is at least 3 times, preferably at least 5 times, more preferably at least 10 times higher than that of the acceptor. In this case, most of the acceptors may be excited when energy is transferred from the donors by FRET rather than by excitation light. As the ratio of the extinction coefficient of the donor to the extinction coefficient of the acceptor increases, the signal-to-noise ratio increases because the acceptor is excited by FRET rather than by excitation light. Hence, a higher ratio of the extinction coefficient of the donor to the extinction coefficient of the acceptor is more preferable.

For easy detection of target substances, the FRET efficiency between the donor and the acceptor is preferably at least 0.05 such that the fluorescence signal is discernable from the background noise.

To this end, when the acceptor signal is observed as in the previous method for detecting target substances, it is preferable to select the donor and acceptor fluorescent substances such that the Förster radii (or Förster distances) of the donor and the acceptor are, for example, at least 0.208 nm. As another example, when FRET efficiencies are measured for multiplexed detection of target substances, it is preferable to select the donor and acceptor fluorescent substances such that the Förster radii (or Förster distances) of the donor and the acceptor are, for example, at least 0.83 nm, as will be described below. In the case where the donor-acceptor distance is adjusted using nucleic acid, the shortest distance between the two fluorescent substances is 1 base pair (bp), i.e. 0.34 nm. Accordingly, when the Förster radius is at least 0.208 nm, the FRET efficiency may be at least 0.05 at a distance of 0.34 nm. If the Forster radius is less than 0.208 nm, the FRET efficiency approaches 0 at a distance of 1 bp, making it difficult to observe the acceptor signal. The larger the Forster radius, the higher the FRET efficiency at the same distance, making the acceptor brighter. Accordingly, a larger Förster radius is more preferable.

As another example, when the FRET efficiency is measured for multiplexed detection, a Förster radius of less than 0.83 nm leads to a significant reduction in distance-dependent FRET efficiency. Even when the donor-acceptor distance reaches only 3 bp, the FRET efficiency decreases to less than 0.05, making it difficult to observe the acceptor signal and measure the FRET efficiency. Accordingly, a Forster radius of 0.83 nm or more is preferable for the detection of 3 or more different target substances. A larger Förster radius enables differential detection of FRET efficiencies in the larger distance range.

To induce an optimal energy transfer, it is necessary to determine an appropriate donor-acceptor distance taking into consideration the donor-acceptor interaction.

FIG. 6 shows a donor strand and an acceptor strand bound with a docking strand. Referring to FIG. 6, the actual gap between donor and acceptor fluorescent substances may, for example, correspond to the distance between the bases of strands labeled with the fluorescent substances and may vary depending on the locations of the strands on which the donor and acceptor fluorescent substances are labeled or the gaps between the donor and acceptor strands bound to the docking strand.

In one embodiment, when the donor strands and the acceptor strands bind simultaneously to the docking strands, the gaps (single strands) between the donor strands and the acceptor strands are smaller than the persistence length of the docking strands.

For example, the base-base distance of a double-stranded DNA is 0.34 nm and the persistence length is 50 nm whereas the base-base distance of a single strand is 0.5 nm or more and the persistence length is only a few nm. The term "persistence length" as used herein means the distance at which a polymer chain such as DNA maintains its linearity and may vary depending on various factors such as the structure and charge of the polymer chain and the salt concentration of a buffer. If the persistence length of the single docking strand is larger than the gap, the docking strand may be bent at somewhere of the gap. In this case, the donor-acceptor distance may be much shorter than the intended distance, and as a result, desired fluorescence signals cannot be obtained, which may cause problems. Therefore, the gap is preferably smaller than the persistence length of the docking strand such that the docking strand maintains its linearity.

In one embodiment, when the fluorescent substances are attached on the strands, flexible linkers may be interposed between the strands and the fluorescent substances. Since the linkers allow the fluorophores to freely rotate, the brightness can be maintained constant independent of the direction in which an observer looks. Each of the linkers may include one or more flexible or rotatable repeating units such as —$CH_2$— and —$CH_2CH_2O$—. The linkers may be from 0.1 nm to a maximum of 10 nm in length. When the length of the linkers is large, the observed location of the fluorophores greatly varies. If the linkers are excessively long, it may be difficult to distinguish the target substances. Thus, it is preferable that the length of the linkers is limited to 10 nm or less.

The donor and acceptor fluorescent substances may be hydrophilic fluorescent substances such as Alexa and CF and hydrophobic fluorescent substances such as Cy and quantum dots. However, in the case where the donor and acceptor strands are close enough to interact with each other, it is preferable to use only hydrophilic fluorescent substances or combinations of hydrophilic fluorescent substances and hydrophobic fluorescent substances. The hydrophobic interaction between two hydrophobic fluorescent substances very close to each other may destabilize the fluorescence signal (Cy3-Cy5 in (d) of FIG. 1).

In one embodiment, a stabilizer such as cyclooctatetraene (COT), nitrobenzyl alcohol (NBA) or trolox may be attached to or near the fluorescent substances or may be present in a buffer to stabilize the fluorescence signals.

In one embodiment, an oxygen scavenger (for example, glucose+glucose oxidase+catalase or PCA+PCD) may be present in a buffer to prevent the fluorescent substances from being photobleached by oxygen.

Noise of the fluorescence signals needs to be minimized to improve the detection accuracy of target substances. To meet this need, the emission wavelength of the donors can be appropriately removed using an optical filter to minimize the fluorescence signals from the donors.

In one embodiment, the wavelength of the optical filter may be controlled such that the signal-to-noise ratio (SNR) of the fluorescence signals is 2 or more. For example, the cut-on wavelength of a long-pass filter, the cut-off wavelength of a short-pass filter or the onset wavelength of a band-pass or band-rejection filter may be longer than or equal to the wavelength at which the emission spectrum of the acceptor is 0.01 and may be shorter than or equal to the wavelength at which the emission spectrum of the donor is 0.01.

FIG. 7 shows the emission spectra of the donor fluorescent substance (solid line) and the acceptor fluorescent substance (dashed line). Amin represents the wavelength at which the emission spectrum of the acceptor is 0.01 and Amax represents the wavelength at which the emission spectrum of the donor is 0.01.

The donor signal can be removed and the acceptor signal can be detected using a long-pass dichroic mirror or dichroic filter through which wavelengths above a predetermined wavelength pass, a short-pass dichroic mirror or dichroic filter through which wavelengths below a predetermined wavelength pass, or a band-pass dichroic mirror or dichroic filter through/from which a predetermined wavelength band is transmitted/reflected.

For a long-pass dichroic filter (hereinafter referred to simply as a "filter") through which wavelengths longer than the cut-on wavelength pass, when the cut-on wavelength of the filter is shorter than $\lambda_{min}$, an acceptor signal passing through an optical filter remains the same while a donor signal increases, resulting in a low signal-to-noise ratio. Accordingly, the cut-on wavelength is preferably longer than or equal to $\lambda_{min}$. Meanwhile, when the cut-on wavelength is longer than or equal to $\lambda_{max}$, a donor signal passing through a dichroic mirror remains the same while an acceptor signal decreases, resulting in a low signal-to-noise ratio. Accordingly, the cut-on wavelength is preferably shorter than or equal to $\lambda_{max}$.

Herein, the signal-to-noise ratio can be defined as follows. FIG. 8*a* shows an acceptor fluorescence signal taken with a camera. A cross-section is taken along the white dashed line to compare the intensity of the signal with the intensity of noise. The cross-section is shown in FIG. 8*b*. This graph is fitted by a Gaussian function. The amplitude of the Gaussian function is defined as a "signal". The values of the other pixels without acceptor fluorescence signals are drawn as a histogram with a normal distribution. The full width at half maximum (FWHM) of the normal distribution is defined as "noise". The ratio of the signal to the noise is defined as the signal-to-noise ratio (SNR).

On the other hand, increases in the concentration of the donor strands and the acceptor strands lead to the occurrence of noise. Thus, it is preferable to reduce noise and accurately determine the acceptor signal. The concentrations of the donor and acceptor strands at which target signals are best detected can be selected taking into consideration the SNR.

In one embodiment, when a predetermined combination of the donor-acceptor fluorescent substances and an optical filter are used, the concentration of the donor strands may be adjusted to 10 nM or higher such that the time necessary for binding the donor strands to the docking strands is an average of 50-100 seconds and 10 μM or lower such that the signal-to-noise ratio is 2 or more.

Binding of the donor strands to the docking strands is a prerequisite for the generation of a signal from the acceptors. The average time necessary for binding the donor strands to the docking strands is inversely proportional to the concentration of the donor strands around the docking strands, as given by Equation 4:

Average time necessary for binding donor strands to docking strands=(500-1000 s×nM)/[Donor strand concentration (nM)] (Equation 4)

The average time is 500-1000 seconds when the concentration is 1 nM, 50-100 seconds when the concentration is 10 nM, and the average time is 5-10 seconds when the concentration is 100 nM. For accurate detection of target substances, the donor strands should bind to the corresponding docking strands at least 5 times. The concentration of the donor strands is preferably 10 nM or higher to complete the entire measurement within 10 minutes, which is preferable in terms of economic efficiency.

When the concentration of the donor strands increases, the intensity of the acceptor signal remains the same whereas the intensity of noise increases, resulting in a reduction in signal-to-noise ratio. The signal-to-noise ratio is 2 or higher when the concentration of the donor strands is 10 μM or less, preferably 5 μM or less. A concentration of 1 μM or less is sufficient for the acceptor strands, unlike for the donor strands, because the acceptor strands are maintained for a long time after binding to the docking strands.

On the other hand, the retention times of the donor and acceptor strands bound to the docking strand can be adjusted depending on the lengths of the donor and acceptor strands. Long retention of the acceptor strands stably bound to the docking strands allows for rapid imaging after the introduction of the donor strands, contributing to a reduction in detection time. Biomarkers can be easily detected with the same imaging time even when the donor strands are used at a low concentration.

In one embodiment, when the strands are DNA or RNA strands, the number of nucleotides complementary to the docking strands is preferably from 6 to 12 for the donor strands and is preferably at least 8 for the acceptor strands. In the Examples section that follows, 7-9 nt long donor strands complementarily binding to docking strands were usually used. However, the length of the donor strands may be reduced when the concentration of cations in a buffer is high and may be increased when the concentration of cations in a buffer is low. When the actual length of the donor strands complementary to the docking strands is 7 nt, the incorporation of mismatch sequences non-complementary to the docking strands leads to an increase in the entire length of the donor strands as much as desired. Therefore, it is preferable to express the donor strands by the number of complementary nucleotides rather than by the entire length.

In one embodiment, when the strands may be PNA, LNA or GNA strands rather than DNA or RNA strands, the number of nucleotides complementary to the docking strands is preferably from 3 to 9 for the donor strands and is preferably at least 5 for the acceptor strands. XNA strands may have a reduced number of nucleotides complementary to the docking strands due to their higher binding affinity to the docking strands than that of DNA or RNA strands.

The length of the docking strands is preferably above the minimum level for the intended complementary binding of the donor strands and the acceptor strands. The incorporation of mismatch sequences or gaps (single-stranded DNA fragments) can increase the length of the docking strands as much as desired, as described above, which accounts for the reason why the docking strands are expressed by their minimum length.

The acceptor strands may have an elongated shape such that they remain bound to the docking strands for a long time or do not unbind from the docking strands. The acceptor fluorescent substance may also be directly attached to the docking strands. Unlike the donors that are excited only by excitation light to emit light, the acceptors emit light only when the donor strands and the acceptor strands bind simultaneously to the docking strands, resulting in a reduced risk of photobleaching.

The acceptor strands may be already bound to the docking strands before the donor strands bind to the docking strands. In this case, the acceptor strands may be relatively long and the donor strands may be short in length to increase the probability that the acceptors emit light by FRET.

When the time for the acceptor strands to remain bound to the docking strands is defined as "a" and the time it takes for the acceptor strands to bind to the docking strands is defined as "b", the probability that the acceptor strands remain bound to the docking strands is represented by "a/(a+b)". a increases with the increasing length of the acceptor strands and with the increasing concentration of a salt, while b decreases with increasing concentration of the acceptor strands. The probability of 1 indicates that the acceptors generate signals whenever the donor strands bind to the docking strands. The probability of 0.5 indicates that the acceptors generate signals with a probability of 0.5 when the donor strands bind to the docking strands. That is, the same acceptor signals can be obtained when the number of the donor strands binding to the docking strands doubles. In conclusion, the higher probability (i.e. the higher a or the lower b) leads to the shorter detection time.

There is a risk of photobleaching of acceptors in existing cell imaging approaches but there is a low possibility of photobleaching in biomarker detection. In a preferred embodiment, the length of the acceptor strands increases or the acceptor fluorescent substance is directly labeled on the docking strands to increase a. When the concentration of the acceptor strands increases, b may be reduced, which is undesirable in terms of the signal-to-noise ratio.

DNA strands are negatively charged, tend to repel each other. Thus, it is preferable that positive charges are introduced into a buffer to neutralize negatively charged DNA strands. When DNA strands complementarily bind to each other, two or three hydrogen bonds (attractive forces) are formed per base. Accordingly, the longer the sequence, the more stable the binding. When the concentration of $Na^+$ is 500 mM and the length of the acceptor strands is 10 nt, the binding is maintained for an average of 40 seconds. The longer acceptor strands maintain the binding for a longer time.

For example, since PNA strands are not negatively charged, unlike DNA strands, PNA-PNA binding and PNA-DNA binding are much more stable than DNA-DNA binding. Accordingly, PNA or LNA strands can be used as the acceptor strands and DNA strands can be used as the docking and donor strands.

On the other hand, excessively high concentrations of target substances in a sample during detection may cause signal overlap, making it difficult to accurately quantify the target substances.

Blood concentrations of most target substances are known but may vary significantly depending on the subject's state. The concentrations may vary from $10^{-15}$ g/ml to $10^{-3}$ g/ml by a factor of about $10^{12}$ depending on the types of the target substances.

Thus, the sample needs to be diluted such that proper numbers of the target substances are displayed in a detection image, for example, by the following procedure. First, a well plate or Lab-Tek provided with well 1, well 2, well 3, . . . , is prepared. Capture antibodies and detection antibodies against target substances whose concentrations are expected to be low are plated in well 1 and well 2. Capture antibodies and detection antibodies against target substances whose concentrations are expected to be high are plated in well 2 and well 3.

Blood is diluted to a standard concentration and placed in well 1. The standard dilution is further diluted and placed in well 2. The resulting solution is further diluted and placed in well 3. Target substances are immobilized onto a substrate. Target substances whose concentrations are expected to be low are detected in well 1. Measurement is continued until proper numbers of the target substances are observed. If the numbers of the target substances are too small to be measured, well 1 is divided into several areas and the numbers of the target substances in the divided areas are combined. Meanwhile, if the numbers of the target substances are too large to be analyzed, an attempt to detect the target substances is made in well 2.

Target substances whose concentrations are expected to be high are detected in well 2. Measurement is continued until proper numbers of the target substances are observed. If the numbers of the target substances are too small to be measured, well 2 is divided into several areas and the numbers of the target substances in the divided areas are combined. Meanwhile, if the numbers of the target substances are too large to be analyzed, an attempt to detect the target substances can be made in well 3. Intermolecular overlap is problematic when excessively large numbers of the target substances are found. This problem can be solved by reducing the concentration of the donor strands, lowering the concentration of a salt in a buffer or incorporating alternative donor strands having a larger number of mismatches or a shorter length, which indicates a smaller number of complementary bonds with the docking strands, than the original donor strands.

As discussed above, the use of the methods and kits according to the present disclosure enables the detection of various biomarkers from a very small amount of biofluid with a 1000-fold higher sensitivity than conventional methods and kits. Therefore, the methods and kits of the present disclosure are useful for the early diagnosis of various diseases, including cancer.

In addition to the above-described method for observing acceptor fluorescence signals, the present disclosure provides methods for multiplexed detection of multiple target substances by measuring FRET efficiencies using strands into which various FRET pairs are introduced depending on the types of target substances.

Another aspect of the present disclosure provides a kit for detecting target substances using detection probes conjugated with tagged strands labeled with fluorescent substances. The kit includes one or more types of detection probes specifically binding to target substances and conjugated with tagged strands. The tagged strands include one or more types of donor fluorescent substances and one or more types of acceptor fluorescent substances. Light is emitted by the FRET between the donor fluorescent substances and the acceptor fluorescent substances when the donor fluorescent substances are excited.

In one embodiment, the tagged strands may have two or more FRET pairs.

In one embodiment, the kit may include a substrate, two or more types of tagged strands labeled with fluorescent substances, and two or more types of detection antibodies conjugated with the tagged strands and simultaneously identifies two or more types of biomarkers using FRET efficiencies by the fluorescent substances. The fluorescent substance may act as a donor or acceptor on a particular base, the 3'- or 5'-end or the backbone of the tagged strand. Two or more biomarkers can be simultaneously detected using different FRET efficiencies measured depending on the distances between the donors and the acceptors labeled on the tagged strands.

The detection antibodies are detection probes for detecting biomarkers through the antigen-antibody reaction. The number of types of the detection antibodies is preferably the same as the number of types of target biomarkers. For measurement of the FRET efficiencies upon detection, the detection antibodies conjugated with the tagged strands labeled with the fluorescent substances are preferably used. In one embodiment of the present disclosure, the tagged strands are typically DNA strands but are not necessarily limited thereto. Preferably, the tagged strands are nucleic acids or analogues thereof or biopolymers. The nucleic acids can be selected from the group consisting of DNA, RNA, PNA, LNA, MNA, GNA, and TNA. The biopolymers can be selected from the group consisting of polypeptides and carbohydrates.

The term "FRET efficiency" as used herein refers to the value of energy transferred from a fluorescent substance excited by light to another adjacent fluorescent substance. The FRET efficiency varies depending on the distance between the fluorescent substances. Specifically, the FRET efficiency is calculated by Equation 5:

FRET efficiency=(Intensity of light from acceptor)/(Sum of intensity of light from donor and intensity of light from acceptor) (Equation 5)

The intensity of light from the donor or acceptor may be affected by the donor-acceptor distance, but the FRET efficiency can be controlled by labeling the donor or acceptor on a particular base, the 3'- or 5'-end or the backbone and varying the donor-acceptor distance.

Here, the FRET efficiency can be obtained by correcting the difference in the detection efficiency of an image sensor resulting from the difference in the wavelength of light from the acceptor excited by light for excitation of the donor, a portion of light from the donor and the acceptor that is not completely separated by an optical component (e.g., a dichroic mirror) or light emitted from the donor and the acceptor.

Target substances can be detected using FRET efficiencies by the following procedure. When one base is present between a donor and an acceptor, the gap between the donor and the acceptor is defined as a "1". Two or more types of tagged strands are constructed in which donors and acceptors are separated from each other by gaps of 1, 2, 3, . . . n. The FRET efficiencies are measured for the different gaps to construct a database. The same type of tagged strands are conjugated to the same type of detection antibodies and different types of tagged strands are conjugated to different types of detection antibodies. Thereafter, when the reaction with a sample containing the biomarkers is allowed to proceed, the biomarkers bind with specific detection antibodies. At this time, the intensities of light from the donor and the acceptor are measured to calculate the FRET efficiency. By comparing the calculated FRET efficiency with the value stored in the database, the types of the detection antibodies can be determined and the types of the biomarkers can finally be identified.

For example, assuming that the gaps at which the FRET efficiencies can be distinguished are integers from 4 to 20 based on the previous description, 17 types of tagged strands can be constructed using one type of donor and one type of acceptor. If two donor-acceptor pairs are present, 289 types of tagged strands can be constructed under the same conditions. If three donor-acceptor pairs are present, 4,913 types of tagged strands can be constructed under the same conditions. Therefore, the number of types of the fluorescent substances necessary for detecting various types of biomarkers can be minimized.

In one embodiment, the tagged strands may be labeled with two or more different fluorescent substances. FIG. 9 schematically shows a kit for simultaneous detection of multiple biomarkers according to one embodiment of the present disclosure. As shown in FIG. 9, biomarkers are immobilized onto a substrate and detection antibodies conjugated with tagged strands (detection antibody tags) are bound to the biomarkers. The kit shown in FIG. 9 includes N types of detection antibodies specifically binding to N types of biomarkers and N types of tagged strands conjugated to the detection antibodies.

The reason for this construction is that when the same FRET efficiency is measured from the different tagged strands conjugated to the different detection antibodies bound to the different biomarkers, the types of the detected biomarkers cannot be identified. Thus, it is preferable that different tagged strands as many as the number of the target biomarkers are used to acquire distinguishable FRET efficiencies.

Specifically, different numbers of bases may be present between donors and acceptors labeled on the two or more types of tagged strands. More specifically, different FRET efficiencies may be obtained depending on the locations of donors and acceptors labeled on the tagged strands. The tagged strands may be labeled with a plurality of donors or acceptors. In this case, the two or more donors may be fluorescent substances different from the acceptors and may be of different types. Alternatively, the two or more acceptors may be fluorescent substances different from the donors and may be of different types. For example, the tagged strands may be labeled with one acceptor and a plurality of donors, as shown in FIG. 10. Here, the donors are preferably fluorescent substances different from the acceptor and are preferably of different types. For example, assuming that the gaps at which the FRET efficiencies can be distinguished are integers from 4 to 20 based on the previous description, theoretically 17 types of tagged strands can be constructed with one FRET efficiency. That is, theoretically 83,521 (17×17×17×17) types of tagged strands labeled with four donors and one acceptor can be constructed with a total of 4 FRET efficiencies between donor 1-donor 2, donor 2-donor 3, donor 3-donor 4, and donor 4-acceptor.

FIG. 11 shows a process for measuring FRET efficiencies from fluorescent substances labeled on the tagged strands shown in FIG. 10 and schematically shows the principle of imaging of fluorescent substances using a single-molecule microscope.

First, tagged strands labeled with fluorescent substances are immobilized onto a substrate. Then, the brightness of each fluorescent substance is observed with the single-molecule fluorescence microscope shown in FIG. 11. Based on the diffraction of light, molecules located close to each other within about 300 nm are not distinguished and can be observed in one spot. Thus, fluorescent substances labeled on one tagged strand and arranged at a distance of 300 nm or less appear in one spot. In contrast, since different fluorescent substances emit light beams of different wavelengths, the emitted light beams can be separated depending on their wavelength using an optical component (e.g., a dichroic mirror) by/through which light in the particular wavelength band is reflected/transmitted, to measure the brightness of light from a particular fluorescent substance.

The left image of FIG. 11 schematically shows a process for outputting light from Cy2, Cy3, Cy5, and Cy7 as four fluorescent substances in one image with a camera. The right image of FIG. 11 schematically shows an imaging process with different cameras depending on the type of fluorescent substances. The above-described processes can be used to calculate the FRET efficiencies between donors and acceptors but other processes may also be used without particular limitation. Specifically, a process for imaging the intensities of light from donors and acceptors through a donor camera and an acceptor camera, respectively, is preferable in terms of analysis time.

FIG. 12 shows the results of imaging by the above-described method using tagged strands labeled with Cy3 and Cy5 as donors and Cy7 as an acceptor. Referring to FIG. 12, when the brightness values were measured by the method shown in the left image of FIG. 11, the imaging results were displayed in the order of Cy3, Cy5, and Cy7 from the leftmost to the rightmost on one monitor. When a red laser was irradiated onto the tagged strands, Cy5 was first excited and energy was transferred to Cy7 by FRET and light was emitted from Cy7. As a result, none was observed in the Cy3 region and bright spots were observed only in the Cy5 and Cy7 regions. Here, the FRET efficiency between Cy5 and Cy7 was measured from the brightness ratio of the spots to determine the distance therebetween. In addition, upon irradiation with a green laser, Cy3 was excited and energy was transferred to Cy5 and Cy7 by FRET and light was emitted from Cy3, Cy5, and Cy7. In this case, the distance between Cy3 and Cy5 was determined based on the measured FRET efficiency between Cy5 and Cy7.

In one embodiment, each of the tagged strands may be labeled with two donor-acceptor FRET pairs, as shown in FIGS. 13 and 14.

In this embodiment, the FRET pairs are preferably spaced a distance from each other to minimize the influence of each FRET pair on the FRET efficiency of the adjacent FRET pair. Specifically, the labeled FRET pairs are more preferably spaced at least 5 nm from each other.

Each of the tagged strands may include two or more donor-acceptor FRET pairs in which the donors and the acceptors are spaced apart from each other by different gaps. The gaps are preferably different such that the measured FRET efficiencies are sufficiently distinguishable when an error range and noise possibly caused during measurement are taken into consideration.

As another example, the same type of donors is used in the two or more FRET pairs. In this case, the same or different types of acceptors may be labeled but the types of the acceptors are preferably different from the type of the donors.

As another example, the same type of acceptors is used in the two or more FRET pairs. In this case, the same or different types of donors may be labeled but the types of the donors are preferably different from the type of the acceptors.

Specifically, when each of the tagged strands is labeled with two FRET pairs, donors and acceptors of the FRET pairs can be used in the following four combinations:

i) The donors may be the same fluorescent substance and the acceptors may be the same fluorescent substance;

ii) The donors may be different fluorescent substances and the acceptors may be the same fluorescent substance;
iii) The donors may be the same fluorescent substance and the acceptors may be different fluorescent substances; and
iv) The donors may be different fluorescent substances and the acceptors may be different fluorescent substances.

The combination i) is exemplified in FIG. 13. Referring to FIG. 13, donor 1 and donor 2 are labeled with a fluorescent substance A and acceptor 1 and acceptor 2 are labeled with a fluorescent substance B. If the two donors labeled with the same fluorescent substance and the two acceptors labeled with the same fluorescent substance are adjacent to each other, they affect the FRET efficiencies of the donor-acceptor FRET pairs. Accordingly, when one tagged strand is labeled with the same two or more donors and the same two or more acceptors, as shown in FIG. 13, the FRET pairs are preferably spaced at least 5 nm from each other.

The combinations ii) to iv) are exemplified in FIGS. 14*a* to 14*c*, respectively.

FIG. 14*a* shows the combination ii). As shown in FIG. 14*a*, donor 1 is labeled with a fluorescent substance A, donor 2 is labeled with a fluorescent substance B, and acceptor 1 and acceptor 2 are labeled with the same fluorescent substance C. That is, the two FRET pairs labeled on one tagged strand are labeled with the same type of acceptors.

FIG. 14*b* shows the combination iii). As shown in FIG. 14*b*, donor 1 and donor 2 are labeled with the same fluorescent substance A, acceptor 1 is labeled with a fluorescent substance B, and acceptor 2 is labeled with a fluorescent substance C. FIG. 14*c* shows the combination iv). As shown in FIG. 14*c*, donor 1 is labeled with a fluorescent substance A, donor 2 is labeled with a fluorescent substance B, acceptor 1 is labeled with a fluorescent substance C, and acceptor 2 is labeled with a fluorescent substance D. That is, one tagged strand is labeled with different types of fluorescent substances.

As shown in FIGS. 14*a* to 14*c*, the first donor 1-acceptor 1 FRET pair and the second donor 2-acceptor 2 FRET pair are spaced a distance from each other. This is to minimize the influence of the adjacent FRET pairs on each other, as described in FIG. 13. The gaps between the donors and acceptors in the first and second FRET pairs may be identical to or different from each other. In the case where the same type of donors and the same type of acceptors are used in first and second FRET pairs, i) a tagged strand labeled with the first and second FRET pairs whose FRET efficiencies are a and b cannot be distinguished from ii) a tagged strand labeled with the first and second FRET pairs whose FRET efficiencies are a and b. Thus, only one of the tagged strands i) and ii) can be used.

In one embodiment, each of the tagged strands may include two or more FRET pairs. The structure of the tagged strand may be the same as that described above. That is, the tagged strand may be similar to that shown in FIG. 13 or may have the same structure shown in FIG. 14*a*, 14*b* or 14*c*.

For measurement of the FRET efficiencies using the kit, the donors are first excited. A predetermined time after excitation, the fluorescent substances do not emit light any further, which is called "photobleaching". Once photobleached, the intensity of light is changed. Also in this case, the intensities of light before and after photobleaching are measured and compared to determine the FRET efficiency of each donor-acceptor pair.

The measurement of the FRET efficiencies by comparing the brightness values of light before and after photobleaching is based on the following basic principle. When photobleached, the donor does not emit light any further or does not transfer energy to the acceptor. The acceptor cannot receive energy from the donor, resulting in reductions in the intensity of light from the donor and the acceptor. In contrast, when the acceptor is photobleached, the donor does not transfer energy to the acceptor and uses all energy for light emission, resulting in an increase in the brightness of light from the donor and a reduction in the brightness of light from the acceptor. This principle will be described in more detail with reference to Example 2-3.

In one embodiment, the kit may further include capture antibodies.

FIG. 16 schematically shows a kit including capture antibodies according to one embodiment of the present disclosure. The capture antibodies may be previously attached to a substrate or may be attached to a substrate during detection. The capture antibodies may be conjugated with tagged strands.

The tagged strands conjugated to the capture antibodies (hereinafter referred to as "capture antibody tags") may have a backbone identical or similar to the tagged strands conjugated to the detection antibodies (hereinafter referred to as "detection antibody tags"). Specifically, the tagged strands may be nucleic acids such as DNA, RNA, PNA, LNA, MNA, GNA or TNA strands or their analogues or biopolymers such as polypeptides or carbohydrates. The tagged strands may have the structure shown in FIG. 17 but are not particularly limited thereto.

In one embodiment, the kit may further include bridge strands.

The bridge strands preferably have a backbone identical or similar to the detection antibody tags and the capture antibody tags. More preferably, the bridge strands are single-stranded nucleic acids having specific sequences. In one embodiment, the bridge strands may complementarily bind to the detection antibody tags and the capture antibody tags.

When the bridge strands are single-stranded nucleic acids, some of the sequences of the bridge strands are complementary to some of the sequences of the capture antibody tags and the other sequences of the bridge strands are complementary to some of the sequences of the detection antibody tags. That is, portions of the bridge strands complementarily bind the detection antibody tags and the capture antibody tags to form two different double-stranded nucleic acids. This structure is shown in FIG. 18.

Some of the FRET pairs necessary to distinguish biomarkers are formed only when the detection antibody tags complementarily bind to the bridge strands. The other FRET pairs are formed only when the capture antibody tags complementarily bind to the bridge strands. The observation of all FRET pairs during biomarker detection indicates that the bridge strands complementarily are bound to the detection antibody tags and the capture antibody tags. It also indicates that the biomarkers are bound with the capture antibodies and the detection antibodies. In contrast, the observation of only some of the plurality of FRET pairs indicates non-specific binding of the detection antibodies to a substrate rather than to biomarkers. This non-specific binding generates a false-positive signal and causes measurement errors. That is, the use of the bridge strands complementarily binding to the detection antibody tags and the capture antibody tags enables removal of the false positive signal, achieving improved accuracy of analysis results.

In one embodiment, a donor or acceptor may be labeled on a particular base, the 3'- or 5'-end or the backbone of each bridge strand. Preferably, the FRET efficiency is measured by labeling a fluorescent substance acting as a donor or acceptor on a particular base of the bridge strand.

FRET efficiencies can be measured after binding of the capture antibody tags, the detection antibody tags, and the bridge strands and labeling with donors or acceptors as follows.

1) The detection antibody tags complementarily bind to the bridge strands to form one or more FRET pairs.

a) Only donors are labeled on the detection antibody tags and acceptors are labeled on the bridge strands.

b) Only acceptors are labeled on the detection antibody tags and donors are labeled on the bridge strands.

c) Either donors or acceptors or both are labeled on the detection antibody tags and either donors or acceptors or both are labeled on donors are labeled on the bridge strands.

2) The capture antibody tags complementarily bind to the bridge strands to form one or more FRET pairs.

a) Only donors are labeled on the capture antibody tags and acceptors are labeled on the bridge strands.

b) Only acceptors are labeled on the capture antibody tags and donors are labeled on the bridge strands.

c) Either donors or acceptors or both are labeled on the capture antibody tags and either donors or acceptors or both are labeled on donors are labeled on the bridge strands.

The above-described principle may also be applied to 1) and 2). For FRET pairs labeled with the same type of donors and the same type of acceptors, i) first and second FRET pairs whose FRET efficiencies are a and b cannot be distinguished from ii) first and second FRET pairs whose FRET efficiencies are b and a. Thus, the capture antibody tags, the detection antibody tags, and the bridge strands are preferably constructed such that only either of i) and ii) can be used. Preferably, donors and acceptors are labeled on the capture antibody tags, the detection antibody tags, and the bridge strands at intervals such that the measured FRET efficiencies are distinguishable.

For 1) and 2), donors and acceptors are preferably labeled with different fluorescent substances. When a plurality of donors or a plurality of acceptor are used, the same or different types of donors may be labeled on the capture antibody tags, the detection antibody tags or the bridge strands and the same or different types of acceptors may be labeled on the capture antibody tags, the detection antibody tags or the bridge strands.

For example, when biomarker 1 is detected using the kit, capture antibody 1, detection antibody 1, and bridge strand 1 are used and capture antibody tag 1 and detection antibody tag 1 bind to bridge strand 1. In this case, when donor 1 is labeled on one of the bases of capture antibody tag 1, acceptor 1 is labeled on one of the bases at sites of bridge strand 1 binding with capture antibody tag 1 such that a desired FRET efficiency is obtained. Simultaneously, detection antibody tag 1 and sites of bridge strand 1 binding with detection antibody tag 1 may be labeled with donor 1 and acceptor 1 or donor 2 and acceptor 2 as different fluorescent substances such that a desired FRET efficiency is obtained. Alternatively, donor 1 and acceptor 2 or donor 2 and acceptor 1 may be labeled. Here, donor 1 and acceptor 1 should be different fluorescent substances and donor 2 and acceptor 2 should also be different fluorescent substances.

Another aspect of the present disclosure provides a method for detecting target substances using detection probes conjugated with tagged strands labeled with fluorescent substances. The method includes a) introducing a sample containing target substances onto a substrate, b) allowing detection probes conjugated with tagged strands to specifically bind to the target substances, c) labeling the tagged strands with one or more types of donor fluorescent substances and one or more types of acceptor fluorescent substances, and d) measuring fluorescence signals generated by the FRET between the donor fluorescent substance and the acceptor fluorescent substance to identify the target substances.

In one embodiment, the tagged strands may have two FRET pairs

The fluorescence signals generated by FRET can be measured by determining the FRET efficiencies. The FRET efficiencies may be determined by measuring the brightness values of light before and after photobleaching of the donors or acceptors.

The gaps between the FRET pairs are controlled so as not to affect the FRET efficiencies of the FRET pairs. The gaps between the FRET pairs are preferably at least 5 nm.

In one embodiment, a method for simultaneous detection of multiple biomarkers is provided. The method includes attaching two or more types of biomarkers to a substrate, allowing two or more types of detection antibodies conjugated with tagged strands (detection antibody tags) labeled with fluorescent substances to bind to the two or more types of biomarkers, and measuring fluorescence signals generated by the binding to determine the FRET efficiency. According to this method, the FRET efficiency of the fluorescent substances can be used to simultaneously identify the types of the biomarkers and to determine the concentrations of the biomarkers in a sample from the numbers of the biomarkers per unit area.

The fluorescent substance may act as a donor or acceptor on a particular base, the 3'- or 5'-end or the backbone of the tagged strand. Preferably, the fluorescent substance acting as a donor or acceptor is labeled on a particular base of the tagged strand to measure the FRET efficiency.

The method can be carried out using the kit for simultaneous detection of multiple biomarkers by the following procedure.

Prior to carrying out the method, a database for FRET efficiencies may be constructed. The database construction is described below. For example, distinguishable FRET efficiency reference values are previously measured to construct a database and compared with FRET efficiencies measured after reaction to identify the types of biomarkers.

The database for FRET efficiencies can be constructed by the following procedure.

First, different fluorescent substances A and B are used as donors and acceptors, respectively, and are labeled on specific bases of DNA backbones to construct different DNA strands as many types as necessary. For example, when 50 types are necessary for a database, 50 types of DNA strands labeled with A and B at different distances are prepared. A material is applied to a substrate and a material having a binding affinity for the applied material is attached to and immobilized on one end of each DNA strand. Alternatively, commercially available DNA strands labeled with fluorescent substances as donors and acceptors may be used without the need to directly construct the DNA strands. In the determination of the fluorescent substances as the donors and the acceptors, it is preferable that the peak emission wavelength of the donor fluorescent substance is preferably shorter than that of the acceptor fluorescent substance.

After two or more types of DNA strands are prepared, the DNA strand labeled with A and B at a distance of 1 is immobilized onto a substrate and the FRET efficiency is measured. Then, the same procedure is repeated for the labeled DNA strands, starting from the DNA strand labeled with A and B at a distance of 2, to acquire FRET efficiency reference values, which are constructed into a database.

Thereafter, the FRET efficiencies measured during biomarker detection are compared with the FRET efficiency reference values. From this comparison, the distances between the donors and acceptors of tagged strands used for detection can be determined, and as a result, the types of the detected biomarkers can be directly identified.

However, there is a possibility that noise may cause errors in the measurement of FRET efficiencies. Due to this possibility, all FRET efficiencies at different distances are not distinguishable. For example, when the FRET efficiency at a distance of 1 is 0.95 (mean)=0.05 (deviation) and the FRET efficiency at a distance of 2 is 0.94±0.05, the distances 1 and 2 cannot be distinguished by the FRET efficiencies. Thus, it is preferable to use only distances at which FRET efficiencies are clearly distinguished among the values stored in the database for practical biomarker detection.

After the FRET efficiency reference values are obtained, a sample containing target biomarkers is introduced onto a substrate and the biomarkers are attached on a substrate.

In one embodiment, the method may further include attaching capture antibodies to the substrate. The capture antibodies may be conjugated with tagged strands (capture antibody tags).

For example, capture antibodies may be adsorbed to the substrate by diluting the capture antibodies with a 0.06 M carbonate or bicarbonate buffer solution at pH 9.5 and bringing the dilution into contact with the substrate at a predetermined temperature for a predetermined time. Alternatively, capture antibodies may be adsorbed to the substrate by coating the substrate surface with biotinylated polyethylene glycol (PEG) or bovine serum albumin (BSA), binding the coated substrate with streptavidin, and binding the streptavidin-bound substrate with biotinylated capture antibodies. Then, the substrate is treated with a raw or processed sample. The capture antibodies adsorbed to the substrate form complexes with the biomarkers in the sample. In addition, the complexes are preferably washed with a cleaning buffer such as Tween 20 or TritonX-100 to remove non-specifically bound antibodies or contaminants.

In one embodiment, the method may further include allowing the capture antibody tags to bind to bridge strands and allowing the detection antibody tags to bind to the bridge strands.

The bridge strands may include sequences complementary to the sequences of the tagged strands and the capture antibody tags. The bridge strands are single-stranded nucleic acids. In this case, some of the sequences of the bridge strands are complementary to the sequences of the tagged strands and the other sequences of the bridge strands are complementary to the sequences of the capture antibody tags. The complementary binding is not particularly limited to these ranges.

All descriptions related to the detection antibody tags can be applied to the capture antibody tags and can equally or similarly be applied to the kits including capture antibodies and the detection methods.

The use of the methods and kits enables simultaneous detection of two or more biomarkers using FRET efficiencies and identification of biomarkers at low concentrations from a small amount of sample. Specifically, the methods of the present disclosure are effective in simultaneously detecting a maximum of about 1000 biomarkers, including biomarkers present in an extremely small amount at the level of 1 fg/ml, and require a very short time for detection and analysis.

A more detailed description will be given regarding the detection of two or more types of biomarkers using the methods of the present disclosure with reference to the Examples section that follows.

Another aspect of the present disclosure provides a kit and method for simultaneous detection and identification of N types of biomarkers based on the FRET efficiencies of fluorescent substances.

The kit may include donor strands and acceptor strands labeled with two or more types of acceptor fluorescent substances that form FRET pairs. The two acceptor fluorescent substances act as a donor and an acceptor and the acceptor strands are thus called "FRET strands".

Specifically, the kit and detection method use the FRET efficiencies of two or more types of fluorescent substances labeled on docking strands or FRET strands and donors labeled on donor strands to simultaneously detect N types of biomarkers.

The kit includes a substrate, n types of docking strands conjugated to N types of detection antibodies, and donor strands complementarily binding to the N types of docking strands. The docking strands or the donor strands include fluorescent substances. The FRET efficiencies of the fluorescent substances are measured to simultaneously identify the N types of biomarkers.

In one embodiment, the kit may further include FRET strands labeled with fluorescent substances. The FRET strands may complementarily bind to the N types of docking strands.

The fluorescent substance can act as a donor or acceptor on a particular base, the 3'- or 5'-end or the backbone of the docking strand, the donor strand or the FRET strand.

In one embodiment, the kit may further include capture antibodies.

One embodiment of the present disclosure provides a method for simultaneous detection of multiple biomarkers including attaching N types of biomarkers to a substrate, allowing N types of detection antibodies conjugated with N types of docking strands to bind the N types of biomarkers, allowing donor strands to bind to the N types of docking strands, and measuring the FRET efficiencies of fluorescent substances labeled on the docking strands or the donor strands. After the N types of biomarkers are identified using the FRET efficiencies, the concentrations of the biomarkers are measured from the numbers of the biomarkers per unit area.

In one embodiment, the method may further include allowing FRET strands labeled with fluorescent substances to bind to the N types of docking strands. The FRET strands may be complementary to the N types of docking strands.

In one embodiment, the method may further include attaching capture antibodies to the substrate.

For example, target substances can be detected using FRET efficiencies by the following procedure. When one base is present between a donor and an acceptor, the gap between the donor and the acceptor is defined as a "1". Two or more FRET pairs are formed in which donors and acceptors are separated from each other by gaps of 1, 2, 3, . . . n. The FRET efficiencies are measured for the different gaps to construct a database. The same type of docking strands are conjugated to the same type of detection antibodies and different types of docking strands are conjugated to different types of detection antibodies. N types of FRET pairs may also be directly labeled on the docking strands.

Thereafter, when the reaction with a sample containing biomarkers is allowed to proceed, the specific biomarkers bind to the specific detection antibodies. At this time, the intensities of light from the donor and the acceptor are measured to calculate the FRET efficiency. For example, when the donor strand labeled with a fluorescent substance acting as donor 1 binds to the docking strand, the FRET efficiency of a FRET pair consisting of donor 2 absorbing light from excited donor 1 and an acceptor can be measured.

In addition, the FRET pairs are labeled on the FRET strands but not on the docking strands. In this case. The FRET efficiencies can be measured at the moment when the donor strands and the FRET strands bind to the docking strands. By comparing the measured values with the values stored in the database, the types of the detection antibodies used for detection can be determined and the types of the biomarkers can finally be identified.

FIGS. 19 to 21 schematically show kits for simultaneous detection of multiple biomarkers according to various embodiments of the present disclosure.

First, as exemplified in FIG. 19, the kit has a structure including detection antibodies, N types of docking strands conjugated to the detection antibodies, and donor strands complementarily binding to the docking strands. Donor 1 as a fluorescent substance is labeled on the donor strand and a FRET pair consisting of donor 2 and an acceptor fluorescent substance is labeled on the docking strand. The FRET efficiency can be measured at the moment when the donor strand binds to the docking strand.

In one embodiment, the kit may further include FRET strands. In this embodiment, the donor and FRET strands labeled with the fluorescent substances remaining non-photobleached repeatedly bind to and unbind from the docking strands and the FRET efficiencies can be measured during the repeated binding and unbinding.

As exemplified in FIG. 20, the kit has a structure including detection antibodies, N types of docking strands conjugated to the detection antibodies, donor strands complementarily binding to the docking strands, and FRET strands complementarily binding to specific ones of the docking strands. Donor 1 as a fluorescent substance is labeled on the donor strand and a FRET pair consisting of donor 2 and an acceptor fluorescent substance is labeled on the FRET strand. The FRET efficiency can be measured at the moment when both the donor strand and the FRET strand bind to the docking strand.

As exemplified in FIG. 21, the kit has a structure including detection antibodies, N types of docking strands conjugated to the detection antibodies, donor strands complementarily binding to the docking strands, and FRET strands complementarily binding to specific ones of the docking strands. Donor 1 as a fluorescent substance is labeled on the donor strand and a FRET pair consisting of donor 2, donor 3, and an acceptor fluorescent substance is labeled on the FRET strand. The labeling of the FRET strand with two or more fluorescent substances enables the detection of multiple biomarkers using the smallest possible number of types of fluorescent substances.

FIG. 22 schematically shows a kit for simultaneous detection of N types of biomarkers according to one embodiment of the present disclosure.

As shown in FIG. 22, the kit has a structure including detection antibodies, N types of docking strands conjugated to the detection antibodies, and donor strands complementarily binding to the docking strands. Donor 1 as a fluorescent substance is labeled on the donor strand and a FRET pair consisting of donor 2 and an acceptor fluorescent substance is labeled on the docking strand. Donor 2 and the acceptor labeled on the docking strand conjugated to detection antibody 1 are located distantly from each other for their low FRET efficiency. Donor 2 and the acceptor labeled on the docking strand conjugated to detection antibody N are located close to each other for their high FRET efficiency.

The reason for this construction is that the same FRET efficiency measured from the docking strands conjugated to the N types of detection antibodies bound to the N types of biomarkers makes it impossible to specify the types of the detected biomarkers.

Consequently, it is preferable to use N different types of docking strands and N different types of FRET pairs corresponding to the number of target biomarkers in order to acquire distinguishable FRET efficiencies. The donor strands binding to the N types of docking strands are preferably of the same type.

Specifically, when two or more types of fluorescent substances are directly labeled on the docking strands, different numbers of bases may be present between the two or more types of labeled fluorescent substances. More specifically, the N types of docking strands may be labeled with FRET pairs having different FRET efficiencies. When two or more types of fluorescent substances are labeled on FRET strands, different numbers of bases may be present between the two or more types of labeled fluorescent substances. More specifically, the N types of FRET strands may be labeled with FRET pairs having different FRET efficiencies. Here, the two or more types of fluorescent substances labeled on the docking strands or the FRET strands may act as donors or acceptors.

FIG. 23 schematically shows a kit for simultaneous detection of N types of biomarkers according to a further embodiment of the present disclosure. As exemplified in FIG. 23, the kit has a structure including detection antibodies, N types of docking strands conjugated to the detection antibodies, donor strands complementarily binding to the docking strands, and FRET strands complementarily binding to specific ones of the docking strands. Donor 1 as a fluorescent substance is labeled on the donor strand. Donor 2 and an acceptor labeled on FRET strand 1 complementarily bound to the docking strand are located distantly from each other for their low FRET efficiency. Donor 2 and the acceptor labeled on FRET strand N complementarily bound to the docking strand conjugated to detection antibody N are located close to each other for their high FRET efficiency. The structure and the principle are the same as those shown in FIG. 22 except that the FRET pairs are labeled on the FRET strands rather than the docking strands.

FIG. 24 schematically shows a kit for simultaneous detection of multiple biomarkers according to a further embodiment of the present disclosure. As exemplified in FIG. 24, the kit has a structure including detection antibodies, N types of docking strands conjugated to the detection antibodies, donor strands complementarily binding to the docking strands, and FRET strands complementarily binding to specific ones of the docking strands. As shown in FIG. 24, two FRET strands 1-1 and 1-2 bind to one docking strand. Donor 1 as a fluorescent substance is labeled on the donor strands, and a FRET pair consisting of donor 2 and an acceptor is labeled on each of FRET strands 1-1 and 1-2 complementarily bound to the docking strand conjugated to the detection antibody. The FRET pairs are preferably labeled so as to have different FRET efficiencies.

The FRET strands having the same FRET efficiency may have the same sequence. Accordingly, one type of FRET strand may complementarily bind to many types of docking strands. For example, in the case where three types of FRET strands are designed to have FRET efficiencies of 0.25, 0.5, and 0.75, biomarker 1 is designed to have FRET efficiencies of 0.25 and 0.5, biomarker 2 is designed to have FRET efficiencies of 0.25 and 0.75, and biomarker 3 is designed to have FRET efficiencies of 0.5 and 0.75, the FRET strands having a FRET efficiency of 0.25 complementarily bind to the docking strands conjugated to biomarker 1 and biomarker 2, the FRET strands having a FRET efficiency of 0.5 complementarily bind to the docking strands conjugated to biomarker 1 and biomarker 3, and the FRET strands having a FRET efficiency of 0.75 complementarily bind to the docking strands conjugated to biomarker 2 and biomarker 3. Here, the number of types of the FRET strands complementarily binding to the N types of docking strands may be not larger than N.

FIG. 25 schematically shows a kit for simultaneous detection of multiple biomarkers according to another embodiment of the present disclosure. As exemplified in FIG. 25, the kit has a structure including detection antibodies, N types of docking strands conjugated to the detection antibodies, donor strands complementarily binding to the docking strands, and FRET strands complementarily binding to specific ones of the docking strands. Donor 1 as a fluorescent substance is labeled on the donor strand and a FRET pair consisting of donor 2 and an acceptor is labeled on FRET strand 1 complementarily bound to the docking strand conjugated to the detection antibody. Here, each of the docking strands is constructed to have two or more binding sites to which the donor strand and the FRET strand complementarily bind. This structure enables at least 2-fold more rapid analysis than the structure of FIG. 23 because the FRET efficiency can be measured when the donor strand and the FRET strand simultaneously bind to at least one binding site.

The same effect can be attained even when FRET pairs are labeled on the docking strands rather than on the FRET strands.

The docking strands or the FRET strands may be labeled with a plurality of donors or acceptors. Here, the two or more donors may be different types of fluorescent substances from the acceptors and may be fluorescent substances of different types. Alternatively, the two or more acceptors may be different types of fluorescent substances from the donors and may be fluorescent substances of different types.

As an example, a plurality of docking strands may be attached to one detection antibody. The docking strands are of the same type. The same type of donor strands and the same type of FRET strands bind to each docking strand. This structure is schematically shown in FIG. 26.

FIG. 26 shows a kit including detection antibodies, N types of docking strands conjugated to the detection antibodies, donor strands complementarily binding to the docking strands, and FRET strands complementarily binding to specific ones of the docking strands. Specifically, two or more docking strands may be conjugated to one detection antibody. Donor 1 as a fluorescent substance is labeled on the donor strand and a FRET pair consisting of donor 2 and an acceptor is labeled on FRET strand 1 complementarily bound to the docking strand conjugated to detection antibody 1. This structure enables at least 2-fold more rapid analysis than the structure of FIG. 23 because the FRET efficiency can be measured when the donor strand and the FRET strand simultaneously bind to one of the two or more docking strands. That is, the effect attained when the kit shown in FIG. 26 is similar to that attained when the kit shown in FIG. 25. The same effect can be attained even when FRET pairs are labeled on the docking strands rather than on the FRET strands.

As a further example, the structure shown in FIG. 25 may be combined with the structure shown in FIG. 26 to provide a kit for simultaneous detection of multiple biomarkers.

FIG. 27 shows a kit for simultaneous detection of multiple biomarkers according to another embodiment of the present disclosure. The kit is suitable for the detection of microRNAs. The kit detects nucleic acids such as DNAs and RNAs, including microRNAs. N types of target nucleic acids are immobilized onto a substrate after a material having a binding affinity for a material coated on the substrate is attached to one end of each target nucleic acid or a nucleic acid complementary to a portion of each target nucleic acid is previously coated on a substrate. Since the sequences of the N types of target nucleic acids are already known, the nucleic acids can be identified using N types of donor strands and FRET strands complementary to the target nucleic acids.

FIG. 28 shows absorption and emission spectra of donor 1 (Alexa Fluor 488), donor 2 (Cy5), and an acceptor (Cy7) in accordance with one embodiment of the present disclosure. (a) of FIG. 28 shows the absorption spectra of the fluorescent substances. For example, the black vertical dashed line in (a) of FIG. 28 indicates a wavelength (488 nm) used to excite donor 1. Here, donor 1 is excited but donor 2 and the acceptor are not excited. In this case, since donor 2 and the acceptor can emit light only when energy is received from donor 1 by FRET, the FRET efficiencies of the FRET pairs can be measured only when the donor strands labeled with donor 1 bind to the docking strands. When FRET strands are used, the FRET efficiencies of the FRET pairs can be measured only when the donor strands and the FRET strands simultaneously bind to the docking strands.

(b) of FIG. 28 shows the emission spectra of the fluorescent substances. For example, the brightness of light from donor 2 is measured by combining the intensities of light in the wavelength band defined between the left and right black vertical dashed lines using a dichroic mirror and the brightness of light from the acceptor is measured by combining the intensities of light in the longer wavelength band than the right dashed line. The FRET efficiency of the FRET pair can be calculated from the brightness of light from donor 2 and the brightness of light from the acceptor. Here, it is preferable to measure only the intensities of light from donor 2 and the acceptor after the FRET efficiency between donor 1 and donor 2 is allowed to reach 1 and the signal from donor 1 is removed by an optical filter.

In addition, the FRET efficiency between donor 1 and donor 2 can be controlled by varying the distance between donor 1 labeled on the donor strand and donor 2 labeled on the FRET strand, and the FRET efficiency can be calculated by measuring the intensities of light from donor 1 and donor 2. In this manner, multiple biomarkers can be detected.

FIG. 29 schematically shows the principle of simultaneous detection of multiple biomarkers according to one embodiment of the present disclosure.

N types of biomarkers are attached to wells under which a substrate is placed, N types of detection antibodies conjugated with N types of docking strands are allowed to bind to the N types of biomarkers, and the wells are filled with a buffer containing donor strands. The donor strands complementarily bind to the docking strands in the wells. The intensities of light from the FRET pairs are measured to determine the FRET efficiencies and to identify the multiple biomarkers. The FRET efficiencies can be calculated by measuring the intensities of light at different wavelengths using a dichroic mirror or the relative spectral intensities of fluorescent substances using a prism or grating.

FIG. 29 shows a procedure for measuring the intensities of light from donor 2 and an acceptor using a dichroic mirror.

In (a) of FIG. 29, two types of biomarkers 1 and 2 are immobilized on a substrate. Detection antibody 1 conjugated with docking strand 1 is bound to biomarker 1 and detection antibody 2 conjugated with docking strand 2 is bound to biomarker 2. (b) of FIG. 29 shows a state in which a donor strand binds to docking strand 2, and as a result, a FRET pair emits light. The brightness values of light from donor 2 and the acceptor are measured to calculate the FRET efficiency for biomarker 2. (c) of FIG. 29 shows a state in which the donor strand unbinds from docking strand 2, and as a result, the FRET pair does not emit light. (d) of FIG. 29 shows a state in which the donor strand binds to docking strand 1, and as a result, the FRET pair emits light. The brightness values of light from donor 2 and the acceptor are measured to calculate the FRET efficiency for biomarker 1. (e) of FIG. 29 shows a state in which the donor strand unbinds from docking strand 1, and as a result, the FRET pair does not emit light. (f) of FIG. 29 shows a state in which the donor strand again binds to docking strand 1, and as a result, the FRET pair emits light. Also in this case, the brightness values of light from donor 2 and the acceptor are measured to calculate the FRET efficiency for biomarker 1. The procedure is continued until each of the FRET efficiencies for all biomarkers in the observation region is measured one or more times. Thereafter, the types of the biomarkers are identified using the FRET efficiencies and the concentrations of the biomarkers are determined from the numbers of the biomarkers per unit area.

The time it takes for the donor strands to bind to and unbind from the docking strands can be controlled by varying the types (DNA, RNA, PNA, etc.) of the donor strands, the lengths of the donor strands binding to the docking strands, and the ion concentration of the buffer. The time can be prolonged such that the donor strands bind to most of the docking strands, contributing to a reduction in measurement time. Meanwhile, when the time is reduced, the donor strands do not bind to most of the docking strands. If the donor strand temporarily binds to one of the docking strands such that the FRET pair emits light, most of the neighboring docking strands do not emit light. Accordingly, the FRET efficiency can be measured without being interfered by other FRET pairs, and as a result, the location of the FRET pair can be measured with a high precision of less than 10 nm. In addition, a number of biomarkers can be measured simultaneously in one image, ensuring a wide dynamic range. The same applies to FRET strands. The time it takes for the donor strands to unbind is preferably reduced to as short as a few seconds and the time it takes for the FRET strands to unbind is preferably extended to as long as several seconds.

The analysis rate can be increased by increasing the concentration of the donor strands or FRET strands to which the binding rate of the donor strands or FRET strands to the docking strands is proportional.

FIG. 30 shows fluorescence images recorded at different concentrations of donor strands in accordance with one embodiment of the present disclosure. As shown in (b) of FIG. 28, the spectrum of donor 1 partially overlaps with that of donor 2. The overlapping area affects the measurement of the brightness of light from donor 2. The brightness of light from donor 2 was measured using an imaging camera and is shown in FIG. 30. (a), (b), and (c) of FIG. 30 are images recorded when the donor strands are present at concentrations of 100 nM, 500 nM, and 1000 nM in buffers, respectively. As shown in FIG. 30, the background noise in the image of donor 2 increased with increasing concentration of the donor strands, deteriorating the accuracy of the measurement of brightness of light from donor 2. That is, the analysis rate increased but the accuracy of the measurement of FRET efficiencies decreased with increasing concentration of the donor strands. To meet requirements in terms of rate and accuracy, it is preferable to adjust the concentration of the donor strands in a buffer to 1 nM to 1 μM.

As another example, a plurality of FRET strands may bind to one docking strand. In this case, the number of donor strands binding to the docking strand may be the same as that of the FRET strands. When acceptors labeled on the plurality of FRET strands are of the same type, the same or different types of donors may be labeled. Here, the types of the donors are preferably different from the types of the acceptors.

Specifically, when a plurality of FRET strands bind to one docking strand, donors and acceptors labeled on the FRET strands may be labeled on the FRET strands in the following four combinations:

i) The donors labeled on the plurality of FRET strands may be the same fluorescent substance and the acceptors labeled on the plurality of FRET strands may be the same fluorescent substance;

ii) The donors labeled on the plurality of FRET strands may be different fluorescent substances and the acceptors labeled on the plurality of FRET strands may be the same fluorescent substances;

iii) The donors labeled on the plurality of FRET strands may be the same fluorescent substance and the acceptors labeled on the plurality of FRET strands may be different fluorescent substances; and iv) The donors labeled on the plurality of FRET strands may be different fluorescent substances and the acceptors labeled on the plurality of FRET strands may be different fluorescent substances.

The fluorescent substance may act as a donor or acceptor on a particular base, the 3'- or 5'-end or the backbone of the strand. Preferably, the fluorescent substance acting as a donor or acceptor is labeled on a particular base of the docking strand, the donor strand or the FRET strand to measure the FRET efficiency.

The sample used in the present disclosure can be selected from the group consisting of blood, serum, plasma, saliva, tissue fluid, and urine, but is not particularly limited as long as it contains target biomarkers depending on the type or characteristics of diagnosis.

According to FRET-PAINT for detecting two or more types of biomarkers by observing an acceptor signal, one type of donor strand is introduced, a docking strand complementary to the donor strand is found and washed, and this process is repeated N times. The entire measurement time is around N minutes (around 1 minute per type, Nis from hundreds to thousands). The donor strands at a concentration of hundreds of nM are used N times, which is disadvantageous in terms of economic efficiency.

In contrast, according to the method of the present disclosure, since target substances are distinguished using the FRET efficiencies of acceptor strands rather than the sequences of acceptor strands. the same type of donor strands can be used, avoiding the need to introduce and wash new donor strands. The entire measurement time can be reduced to about 1 minute and the donor strands at a concentration of hundreds of nM are consumed only once.

Since 10 FRET efficiencies are distinguishable with one acceptor strand, the number of the acceptor strands can be increased depending on the number of targets. However, when the number of targets distinguishable with one acceptor strand is 10, the number of targets distinguishable with two acceptor strands is not 100 but 55. In this manner, the number of targets distinguishable with three acceptor strands is not 220 but 1,000 and that with four acceptor strands is not 715 but 10,000. The reason for this is that target 1 adapted for FRET efficiencies of 0.1 and 0.2 and target 2 adapted for FRET efficiencies of 0.1 and 0.3 are distinguishable from each other but target 1 adapted for FRET efficiencies of 0.1 and 0.2 and target 2 adapted for FRET efficiencies of 0.2 and 0.1 are not distinguishable from each other.

The above problem can be solved by using N types of common donor strands. For example, in the case where common donor strands are used, target 1 adapted for FRET efficiencies of 0.1 and 0.2 cannot be distinguished from target 2 adapted for FRET efficiencies of 0.2 and 0.1. In contrast, when a primary donor strand is introduced, 0.1 and 0.2 are measured for target 1 and target 2, respectively. When a secondary donor strand is introduced, 0.2 and 0.1 are measured for target 1 and target 2, respectively. Therefore, target 1 and target 2 can be distinguished from each other. That is, when N types of common donor strands are used, donor strands are introduced only N times, and washing is repeated after measurement, 101 target substances, for example, 100 (N=2), 1,000 (N=3), and 10,000 (N=4) target substances, can be distinguished.

As described above, FRET efficiencies can be used to simultaneously detect two or more types of biomarkers and to distinguish the types of biomarkers present at low concentrations in a small amount of a sample. The strands labeled with fluorescent substances tend to temporarily bind to one another. Therefore, even when fluorescent substances acting as donors or acceptors are photobleached, donor strands or FRET strands labeled with fluorescent substances remaining non-photobleached bind to docking strands and the FRET efficiencies can be measured during repeated binding and unbinding, enabling simultaneous detection of N types of biomarkers irrespective of whether photobleaching occurs or not.

The fluorescent substance labeled on the FRET strand emits light only at the moment when the donor strand and the FRET strand bind simultaneously to the docking strand. Meanwhile, when no FRET strand is used, the fluorescent substance labeled on the docking strand emits light only at the moment when the donor strand binds to the docking strand. Therefore, the temporarily light-emitting fluorescent substance can be measured without being interfered by neighboring fluorescent substances, and as a result, the location of the fluorescent substance can be measured with a high precision of less than 10 nm. In addition, a number of biomarkers can be measured simultaneously in one image, ensuring a wide dynamic range.

A more detailed description will be given regarding the detection of N types of biomarkers using the methods of the present disclosure with reference to the Examples section that follows.

Another aspect of the present disclosure provides a kit and method for simultaneous detection and identification of N types of biomarkers based on the measurement of emission spectra by the FRET between different types of fluorescent substances.

According to the present disclosure, the same combination of acceptor fluorescent substances is labeled on different acceptor strands but the FRET efficiencies of the acceptor strands can be determined to distinguish targets because the distances between the acceptor strands are different.

In contrast, different combinations of acceptor fluorescent substances are labeled on different acceptor strands and the FRET efficiencies of the acceptor strands can be determined to distinguish targets. For example, in the case where target 1 is labeled with acceptor 1 and acceptor 2 and target 2 is labeled with acceptor 1 and acceptor 5, the spectrum of target 1 is distinguished from that of target 2. Accordingly, since different acceptors may simultaneously emit light, all donors and acceptors can be labeled on docking strands. Since all acceptors emit fluorescence signals at the moment when the donors are excited, the entire measurement time can be reduced to only a few seconds and the need to use the donor strands can be avoided, which is economically desirable.

In one embodiment, the kit includes a substrate, N types of docking strands labeled with two or more types of fluorescent substances, and N types of detection antibodies conjugated with the docking strands.

In a further embodiment, the kit includes a substrate, N types of docking strands labeled with one or more types of fluorescent substances, N types of detection antibodies conjugated with the docking strands, and donor strands labeled with one or more types of fluorescent substances.

In another embodiment, the kit includes a substrate, N types of docking strands, N types of detection antibodies conjugated with the docking strands, donor strands labeled with one or more types of fluorescent substances, and acceptor strands labeled with one or more types of fluorescent substances.

In each of the embodiments, the fluorescent substance may act as a donor or acceptor on a particular base, the 3'- or 5'-end or the backbone of the docking strand, the donor strand or the acceptor strand.

The kits according to the foregoing embodiments can measure the emission spectra by the FRET between different types of fluorescent substances to simultaneously identify N types of biomarkers.

The docking strands are capable of complementary binding with the donor strands or the acceptor strands.

In one embodiment, each of the kits may further include capture antibodies.

A method for simultaneous detection of multiple biomarkers according to one embodiment of the present disclosure includes attaching N types of biomarkers to a substrate, allowing N types of detection antibodies conjugated with N types of docking strands to bind the N types of biomarkers, and measuring the emission spectra of the docking strands. Here, the emission spectra are measured by the FRET between different fluorescent substances to simultaneously identify the N types of biomarkers, and then the concentrations of the biomarkers in a sample are measured from the numbers of the biomarkers per unit area.

A method for simultaneous detection of multiple biomarkers according to one embodiment of the present disclosure includes attaching N types of biomarkers to a substrate, allowing N types of detection antibodies conjugated with N types of docking strands to bind the N types of biomarkers, allowing donor strands to bind to the N types of docking strands, and measuring the emission spectra. Here, the emission spectra are measured by the FRET between different fluorescent substances to simultaneously identify the N types of biomarkers, and then the concentrations of the biomarkers in a sample are measured from the numbers of the biomarkers per unit area.

In one embodiment, the method may further include allowing the acceptor strands labeled with fluorescent substances to bind to the docking strands.

In one embodiment, the method may further include attaching capture antibodies to the substrate.

According to the kits and methods of the present disclosure, the emission spectra are measured based on the FRET induced by resonance of two or more types of fluorescent substances labeled on the docking strands or the donor or acceptor strands to simultaneously detect multiple biomarkers.

The detection antibodies are used for detection based on the antigen-antibody reaction. The number of types of the detection antibodies is preferably the same as the number of types of target biomarkers. Either the donors or the acceptors labeled on the N types of docking strands are of the same type, which is preferred for simple construction of the detection kit. Specifically, when the donors labeled on the N types of docking strands are of the same type, the emission spectra of the docking strands can be measured using only one light source without a further light source and an optical filter to identify N types of biomarkers. More specifically, FRET occurs when the emission spectrum of a fluorescent substance as the donor overlaps the absorption spectrum of a fluorescent substance acting as the acceptor in a predetermined wavelength range.

For example, when the docking strands labeled with the same type of donors are conjugated to detection antibodies 1 to N and acceptors 1 to N are labeled on the docking strands, as shown in FIG. 31, the same type of donors excite only one light source for initial irradiation. Since the emission spectrum varies depending on the type of the fluorescent substance acting as the acceptor, the type of the acceptor can be identified by determining the measured spectrum of light. The labeling of docking strand N conjugated to detection antibody N with acceptor N enables the identification of the detection antibody labeled with the acceptor and the type of the biomarker having a binding affinity for the detection antibody.

As shown in FIG. 32, docking strands conjugated to detection antibodies 1 to N may be labeled with the same type of donors and the same type of acceptors. The distance between the donors and the acceptors varies, as shown in (a), (b), and (c) of FIG. 32. The use of the donors and the acceptors enables simultaneous detection of multiple biomarkers based on spectral differences by the FRET efficiencies, as shown in the right spectra of FIG. 32.

Alternatively, the same type of acceptors and two or more types of donors may also be labeled on docking strands conjugated to detection antibodies, as shown in FIG. 33. Since the spectra (dotted lines) of two or more types of fluorescent substances acting as the donors overlap (see the right spectra of FIG. 33), the two or more types of fluorescent substances can be excited by one light source. In addition, the emission spectra (solid lines) can be clearly distinguished. In conclusion, the use of two or more types of donors enables the detection of a larger number of types of biomarkers than the use of the same type of donors (see FIG. 31 or 32).

As a further example, the same type of donors and two or more types of acceptors may be labeled on docking strands conjugated to detection antibodies, as shown in FIGS. 34*a* to 34*c*.

The labeled two or more types of acceptors may be adjacent to each other to form acceptor-acceptor FRET pairs, as shown in FIG. 34*a*, or may be adjacent to donors to form donor-acceptor FRET pairs, as shown in FIG. 34*b*. The types of biomarkers can be identified by varying the distance between the labeled acceptors in the acceptor-acceptor FRET pairs. FIG. 34*c* shows the results of multiplexed detection by labeling of the acceptor-acceptor FRET pairs with the same type of donors and five types of acceptors as shown in FIG. 34*a*. Specifically, FIG. 34*c* shows the spectra of light emitted from the docking strands labeled with the FRET pairs (acceptor 1, acceptor 2), (acceptor 1, acceptor 3), (acceptor 1, acceptor 4), (acceptor 1, acceptor 5), (acceptor 2, acceptor 3), (acceptor 2, acceptor 4), (acceptor 2, acceptor 5), (acceptor 3, acceptor 4), (acceptor 3, acceptor 5), and (acceptor 4, acceptor 5) in this order from the bottom. That is, the types of the docking strands can be clearly distinguished based on the measured spectra, and as a result, the types of the acceptor-acceptor FRET pairs used in the docking strands can be determined to identify the types of the detected biomarkers.

The kits according to the foregoing embodiments of the present disclosure can be used alone or in combination thereof for multiplexed detection and identification of ~1,000 types of biomarkers.

Two or more combinations of the same type of two or more fluorescent substances on one docking strand can enhance the intensity of a signal by a factor of at least 2.

FIGS. 35*a* and 35*b* show methods for simultaneous detection of multiple biomarkers according to exemplary embodiments of the present disclosure. According to these methods, N types of target biomarkers can be identified by measuring different emission spectra of N types of docking strands conjugated to N types of detection antibodies specifically binding to the target biomarkers.

First, biomarkers are immobilized on a substrate and are allowed to bind with detection antibodies. N types of capture antibodies may be previously attached to the substrate. In this case, it is preferable that the N types of capture antibodies specifically bind to the corresponding biomarkers. However, this is merely illustrative and the biomarkers may be directly attached to the substrate for rapid, economical, and convenient measurement. If needed, the biomarkers can also be detected through the antigen-antibody reaction with the capture antibodies attached to the substrate for higher accuracy of measurement results.

The target biomarkers may be directly attached to the substrate surface. Alternatively, the substrate may be surface modified such that the capture antibodies are attached to the substrate surface to capture biomarkers. The substrate is preferably coated with a material capable of specific binding to the capture antibodies. Specifically, it is preferable that the substrate is coated with a material specific for the capture antibodies and non-specific for the detection antibodies or strands.

The capture antibodies may be attached to the substrate by diluting the capture antibodies with a 0.06 M carbonate or bicarbonate buffer solution at pH 9.5 and bringing the dilution into contact with the substrate at a predetermined temperature for a predetermined time. The capture antibodies may be adsorbed to the substrate by coating the substrate surface with biotinylated polyethylene glycol (PEG) or bovine serum albumin (BSA), binding the coated substrate with streptavidin, and binding the streptavidin-bound substrate with biotinylated capture antibodies. Then, the substrate is treated with a raw or processed sample. The capture antibodies adsorbed to the substrate form complexes with the biomarkers in the sample. In addition, the complexes are preferably washed with a cleaning buffer such as Tween 20 or TritonX-100 to remove non-specifically bound antibodies or contaminants.

As described above, N types of biomarkers are immobilized on the substrate through the capture antibodies or the material applied to the substrate, and the detection antibodies are allowed to bind to the biomarkers. Thereafter, the emission spectra of docking strands are measured and compared with previously measured emission spectra stored in a database to identify the corresponding biomarkers. The concentrations of the biomarkers can be measured by comparing the numbers of the biomarkers per unit area in an image with the previously measured numbers of the biomarkers per unit area at different concentrations. When donors are excited by irradiation with light from a light source, the emission spectrum of each molecule is observed in an image, as shown in FIG. 35*a*, and compared with previously measured emission spectra (A, B, C, etc.) stored in a database to identify which biomarker corresponds to each molecule observed in the image (e.g., biomarker 1 when the spectral shape is A, biomarker 2 when the spectral shape is B, and biomarker 3 when the spectral shape is C). Thereafter, the concentration of each biomarker in the sample can be measured by measuring the number of the biomarker per unit area in an image and comparing it with the previously measured numbers of the biomarker per unit area at different concentrations. For example, when the previously measured number of biomarker 1 per unit area (ng/ml) at a predetermined concentration is 10 and the actually measured number of biomarker 1 per unit area is 5, the concentration of biomarker 1 in the sample is 0.5 ng/ml.

FIG. 35*b* shows an exemplary method for measuring emission spectra. For example, when various types of fluorescent substances are observed using a general microscope, circular point spread functions (PSFs) are observed irrespective of emission spectra, as shown in the left image. However, the use of an optical component (such as a prism or grating) causing a wavelength-dependent optical path difference on an optical path can change the circular point spread function of each fluorescent substance to an elliptical one. The emission spectrum can be measured by comparing the center of the original circle with the center of the ellipse and analyzing the profile along the major axis of the ellipse. The measured emission spectrum is compared with previously measured emission spectra stored in a database to determine the constituent fluorescent substance of the corresponding molecule (see "Ultrahigh-throughput single-molecule spectroscopy and spectrally resolved super-resolution microscopy", Zhengyang Zhang, Samuel J Kenny, Margaret Hauser, Wan Li & Ke Xu, Nature Methods volume 12 (2015), pages 935-938).

In one embodiment, the docking strands conjugated to the detection antibodies may complementarily bind to donor strands or acceptor strands.

In this embodiment, the donor strands are labeled with donors and the acceptor strands are labeled with one or more types of acceptors or acceptor-acceptor FRET pairs. When the docking strands are directly labeled with two or more types of acceptors, as shown in FIG. 36*a*, the donor strands can complementarily bind to sites adjacent to the labeled areas. FRET occurs at the moment of binding, and as a result, the acceptors can emit light. When the docking strands are not labeled with fluorescent substances, as shown in FIG. 36*b*, the donor strands and the acceptor strands repeatedly bind to and unbind from the docking strands. Thus, the acceptors emit light only at the moment when the donor strands and the acceptor strands bind simultaneously to the docking strands, and their emission spectra can be measured. For this reason, given that a predetermined reaction time is allowed even when some fluorescent substances are photobleached, the emission spectra can be measured at the moment when the donor strands and the acceptor strand labeled with non-photobleached fluorescent substances bind simultaneously to the docking strands. In addition, the emission spectra can be measured and recorded at the moment when the donor strands and the acceptor strands bind simultaneously to the docking strands. This can provide a solution to the problem that many images corresponding to the types of the biomarkers are output simultaneously in one image, making it difficult to identify the biomarkers.

FIG. 37 shows an exemplary method for identifying the types of biomarkers using the detection kit including donor strands and acceptor strands shown in FIG. 36*b*.

First, when it intends to detect N types of biomarkers, N types of docking strands and donor and acceptor strands complementarily binding to the docking strands are designed and the emission spectra of the strands are previously measured to construct a database. Detection antibodies 1 to N are allowed to bind to biomarkers 1 to N, respectively, and docking strands 1 to N are conjugated to detection antibodies 1 to N, respectively.

After completion of the database recording, the biomarkers are immobilized on a substrate. The biomarkers are identified using the docking strands suitable for the types of the target biomarkers as follows. The detection antibodies are allowed to bind to the corresponding biomarkers, and the previously constructed donor strands and acceptor strands area allowed to repeatedly bind to and unbind from the docking strands for a predetermined time. When the donor and acceptor strands bind simultaneously to one docking strand, signals are displayed in an image, as shown in FIG. 37. The spectrum of the corresponding signal is analyzed and compared with the previously measured spectra recorded in the database to identify the types of biomarkers. The locations where the signals are detected on every image are cumulatively displayed and signals repeatedly produced by one biomarker molecule form populations in the form of Gaussian functions around a specific location. The number of the biomarkers per unit area is calculated by regarding one population as one biomarker molecule and the concentrations of the biomarkers in the sample can be measured by comparison with the previously measured numbers of the biomarkers per unit area at different concentrations.

For one or a combination of two or more of the structures shown in FIGS. 31 to 34, approximately 1,000 types of biomarkers can be identified by labeling donors on the donor strands and labeling acceptors on the docking or acceptor strands. For example, a plurality of donor strands and a plurality of acceptor strands complementarily bind to one docking strand, as shown in FIG. 38*a*. This combination enables the detection of biomarkers of the same type as those detected by the structure of FIG. 36*b*. Since two or more sites complementarily binding to the donor and acceptor strands are present in the docking strands, the emission spectra can be measured as long as the donor and acceptor strands bind simultaneously to any one of the sites. Therefore, the repeated binding and unbinding of the donor and acceptor strands can increase the probability of binding to the docking strands, achieving at least 2-fold more rapid detection.

In this case, different donors may be labeled on the plurality of donor strands. Each of the plurality of donor strands may be labeled with donors such that adjacent acceptors or acceptor-acceptor FRET pairs are at different distances for different FRET efficiencies. The acceptors or the acceptor-acceptor FRET pairs may be composed of different fluorescent substances. The plurality of acceptors or acceptor-acceptor FRET pairs may be labeled such that they are at different distances from the donors for different FRET efficiencies. The acceptor-acceptor FRET pairs may be labeled such that the acceptors are at different distances for different FRET efficiencies.

As an approach to obtain an effect similar to that shown in FIG. 38*a*, docking strands having the same structure may be conjugated to one detection antibody for more rapid detection of biomarkers, as shown in FIG. 38*b*.

As a combination of the structures shown in FIGS. 38*a* and 38*b*, two or more types of docking strands to which a plurality of donor strands and a plurality of acceptor strands can complementarily bind may be conjugated to one detection antibody. This combination can further increase the detection rate of biomarkers.

A kit for simultaneous detection of multiple biomarkers according to one embodiment of the present disclosure can be used to detect microRNAs, as shown in FIG. 39.

FIG. 39 shows an exemplary kit for detecting nucleic acids such as DNAs and RNAs, including microRNAs. N types of target nucleic acids are immobilized onto a substrate after a material having a binding affinity for a material coated on the substrate is attached to one end of each target nucleic acid or a nucleic acid complementary to a portion of each target nucleic acid is previously coated on a substrate. Since the sequences of the N types of target nucleic acids are already known, the nucleic acids can be identified using N types of donor strands and acceptor strands complementary to the target nucleic acids.

Nucleic acids such as DNA, RNA, PNA, LNA, MNA, GNA or TNA or analogues thereof can be used as docking strands, donor strands or acceptor strands. In addition, the use of donor strands and acceptor strands may be omitted, as shown in FIGS. 31 to 34. In this case, the docking strands may be polypeptides or carbohydrates.

The intensity of light from donors or acceptors may be affected by the distances between the donors and the acceptors, but docking strands with different FRET efficiencies can be constructed by labeling each of the donors and the acceptors on a desired particular base, the 3'- or 5'-end or the backbone to control the donor-acceptor distances or the acceptor-acceptor distances.

For example, fluorescent substances having different FRET efficiencies are labeled on N types of docking strands, and the emission spectra of the docking strands are previously measured to construct a database and compared with emission spectra generated upon reaction for biomarker detection, with the result that the types of the biomarkers can be detected. The fluorescent substances having different FRET efficiencies may consist of (donor 1, acceptor 1), (donor 1, acceptor 2), . . . , (donor 1, acceptor N), . . . , (donor 1, acceptor 1), (donor 2, acceptor 1), . . . , (donor N, acceptor 1). The fluorescent substances having different FRET efficiencies may consist of two or more different types of acceptors such as (acceptor 1, acceptor 2), (acceptor 1, acceptor 3), (acceptor 2, acceptor 3), . . . on docking strands labeled with the same donors.

The combinations of the fluorescent substances having different FRET efficiencies are merely illustrative and are not particularly limited as long as the FRET efficiencies are different enough to be distinguished upon detection.

According to one embodiment of the present disclosure, each of the methods may further include measuring the emission spectra of the N types of docking strands to construct a database. Before the reaction for detection, docking strands are designed to have one or more of the above-described structures and their emission spectra are measured to construct a database and compared with values measured upon reaction to determine the types of detection antibodies used for detection and the types of the biomarkers can finally be identified.

For the detection of N types of biomarkers, emission spectra may be measured simultaneously or sequentially. For example, when it intends to detect three types of biomarkers, donor strands complementarily bind to docking strands 1, 2, and 3 conjugated to detection antibodies 1, 2, and 3 simultaneously or sequentially. When acceptors are directly labeled on the docking strands, emission spectra can be measured only at the moment when the donor strands bind temporarily to the docking strands. When acceptor strands 1, 2, and 3 are further used, they repeatedly bind to and unbind from acceptor strands 1, 2, and 3 simultaneously or sequentially. During repeated binding and unbinding, the emission spectra can be measured only at the moment when the donor strands simultaneously bind to any one of the docking strands. In other words, the emission spectra of docking strand 1 can be measured only at the moment when the donor strands and acceptor strand 1 simultaneously bind to docking strand 1. In contrast, in the case where the donor strands bind to only docking strand 2 or 3 at the moment when acceptor strand 1 binds to docking strand 1, the emission spectra of docking strand 1 cannot be measured. That is, the emission spectra can be measured simultaneously or sequentially for the detection of N types of biomarkers and the measured values are compared with the values stored in the database to simultaneously identify the N types of biomarkers.

According to the present disclosure, N types of biomarkers can be detected simultaneously based on the FRET and the types of biomarkers at low concentrations present in a small amount of a sample can be distinguished, as described above. Specifically, according to the present disclosure, the emission spectra of strands labeled with fluorescent substances can be measured based on energy resonance to identify the types of biomarkers. In addition, a plurality of biomarkers can be identified with one light source by equally labeling fluorescent substances acting as donors, avoiding the need for an additional light source and an optical filter. This contributes to simplicity of construction and prevents emission spectra necessary for measurement from being lost by an additional optical filter.

Furthermore, strands labeled with donors and acceptors tend to temporarily bind to one another. Therefore, even when fluorescent substances acting as donors or acceptors are photobleached, emission spectra can be measured at the moment when donor strands or acceptor strands labeled with fluorescent substances remaining non-photobleached bind to docking strands during repeated binding and unbinding, enabling simultaneous detection of N types of biomarkers irrespective of whether photobleaching occurs or not. Moreover, the temporarily light-emitting fluorescent substance can be measured without being interfered by neighboring fluorescent substances, and as a result, the location of the fluorescent substance can be measured with a high precision of less than 10 nm, ensuring a wide dynamic range.

A more detailed description will be given regarding the detection of N types of biomarkers using the methods of the present disclosure with reference to the Examples section that follows.

EXAMPLES

1. Multiplexed Detection of Biomarkers Using Donor Strands Having Different Sequences

Experimental Methods

1) Reagents and Materials

Modified DNA oligonucleotides were purchased from Integrated DNA Technologies. AF488 (Alexa Fluor 488 NHS Ester, catalog number: A20000) was purchased from Thermo Fisher Scientific. Cy3 (Cy3 NHS Ester, catalog number: PA13101) and Cy5 (Cy5 NHS Ester, catalog number: PA15101) were purchased from GE Healthcare Life Sciences. COS-7 cells were purchased from Korean Cell Line Bank. The anti-tubulin antibody (catalog number: ab6160) was purchased from Abcam. Anti-Tom20 antibody (sc-11415) was purchased from Santa Cruz Biotechnology, Inc. Donkey anti-rabbit IgG antibody (catalog number: 711-005-152) and donkey anti-rat IgG antibody (catalog number: 712-005-153) were purchased from Jackson ImmunoResearch Laboratories, Inc. Carboxyl latex beads (catalog number: C37281) were purchased from Thermo Fisher Scientific and paraformaldehyde (catalog number: 1.04005.1000) was purchased from Merck. Glutaraldehyde (catalog number: G5882), Triton X-100 (catalog number: T9284), and Bovine Serum Albumin (BSA, catalog number: A4919) were purchased from Sigma-Aldrich. The docking strands were conjugated to the secondary antibodies using Antibody-Oligonucleotide All-in-One Conjugation Kit (catalog number: A-9202-001) purchased from Solulink.

2) DNA Labeling with Fluorophores

Amine-modified DNA oligonucleotides were labeled with fluorophores which have NHS ester chemical group. 5 μl of 1 mM DNA was mixed with 25 μl of 100 mM sodium tetraborate buffer (pH 8.5). And then 5 μl of 20 mM fluorophore in DMSO was added. The mixture was incubated at 4° C. overnight. 265 μl of distilled water, 900 μl of ethanol, and 30 μl of 3 M sodium acetate (pH 5.2) were added and mixed thoroughly. The mixture was incubated at −20° C. for an hour and then centrifuged for a couple of hours. After ethanol was evaporated completely, the DNA pellet was resuspended in 50 μl of distilled water and the fluorescent labeling efficiency was measured.

3) Cell Culture and Fixation

For drift correction of DNA-PAINT imaging, glass coverslips were coated with carboxyl latex beads.

The coverslip was coated with bead solution 1:10 diluted in distilled water, heated for 10 minutes on a 100° C. hot plate, washed with distilled water, and dried with $N_2$ gas. COS-7 cells were grown on bead-coated coverslips and then fixed for 10 minutes. 2% glutaraldehyde was used for microtubule imaging and 3% paraformaldehyde and 0.1% glutaraldehyde mixture in PBS buffer was used for microtubule and mitochondria imaging. Fixed samples were stored at 4° C. in PBS buffer until needed.

4) Immunostaining

After cell culture on coverslips and fixation, microtubules were treated with 1:100 diluted anti-tubulin antibodies in a blocking solution (5% BSA and 0.25% Triton X-100 in PBS buffer), incubated at 4° C. overnight, and immunostained. After thorough wash-out of free anti-tubulin antibodies with PBS buffer, cells were incubated with 100 nM secondary antibodies conjugated with docking strands (Docking_P1) for 1 hour. Mitochondria were treated with 1:100 diluted anti-Tom20 antibodies, incubated at 4° C. overnight, and immunostained. After thorough wash-out of free anti-Tom20 antibodies with PBS buffer, cells were incubated with 100 nM secondary antibodies conjugated with docking strands (Docking_P2) for 1 hour.

5) Single-Molecule Imaging

For single-molecule imaging, a prism-type total internal reflection fluorescence (TIRF) microscopy and highly inclined and laminated optical sheet (HILO) microscopy were used. The microscope was built by modifying a commercial inverted microscope (IX71, Olympus), and equipped with a 100× 1.4 NA oil-immersion objective lens (UPlanSApo, Olympus).

Docking strands were immobilized on the polymer-coated quartz slide surface by using streptavidin-biotin interaction, and donor and acceptor strands were added into the imaging channel. Alexa488, Cy3, and Cy5 were excited by a blue laser (473 nm, 100 mW, MBL-III-473-100 mW, CNI), a green laser (532 nm, 50 mW, Compass 215M-50, Coherent), and a red laser (642 nm, 60 mW, Excelsior-642-60, Spectra-Physics), respectively. Cy3 signal was filtered using a dichroic mirror (640dcxr, Chroma), and Cy5 signal was filtered using a dichroic mirror (740dcxr, Chroma). Single-molecule images were recorded at a frame rate of 10 Hz with electron multiplying charge-coupled device (EMCCD) camera (iXon Ultra DU-897UCS0-#BV, Andor).

6) FRET Pair Characterization

To characterize detected photons detected per frame in FIGS. **1*d*, 13997 (8096), 11021 (5100), 11208 (3451), and 17051 (3980) single-molecule spots were collected for 2 nt, 4 nt, 6 nt, and 11 nt Cy3-Cy5 (Alexa488-Cy5) FRET pairs, respectively. To characterize SNR in FIGS. 1*j*-1*k***, 795, 2322, and 742 single-molecule spots were collected for Cy3, Cy3-Cy5 pair, and Alexa 488-Cy5 pair, respectively.

7) Drift Correction

For super-resolution imaging with DNA-PAINT, a home-made autofocusing and drift correction system based on image correlation method was used. Before filming, one in-focus bright-field image and two out-of-focus images were taken. These three reference images were used to keep track of x, y, and z axes drift. The drift in z-direction was corrected in real-time using a piezo stage (PZ-2000, Applied Scientific Instrumentation) whereas the drift in the xy-plane was corrected during image analysis.

Example 1-1: Characterization of FRET-PAINT

Surface-immobilized DNA strands and a TIRF microscope were used to test the feasibility of FRET-PAINT microscopy.

FIGS. **1*a* to 1*k*** show the principle and characterization of FRET-PAINT.

Specifically, FIG. **1*a* shows docking strands (black), donor strands (dark grey), and acceptor strands (bright grey) used to characterize FRET-PAINT, FIG. 1*b* is a schematic diagram of FRET-PAINT, FIG. 1*c* shows representative Cy5 fluorescence intensity time traces (1000 nM Donor_P1 Alexa488 and 100 nM Acceptor_P11_Cy5), and FIG. 1*d*** shows the brightness of acceptors as a function of the donor-acceptor distance for Cy3-Cy5 and Alexa488-Cy5 pairs.

FIG. **1*e* shows DNA-PAINT images of surface-immobilized docking strand (Docking_P0) at indicated concentrations of Acceptor_P11_Cy3, FIG. 1*f* shows FRET-PAINT images of Docking_P0 at indicated concentrations of Donor_P1_Cy3 with Acceptor_P6_Cy5 fixed at 10 nM, FIG. 1*g* shows FRET-PAINT images of Docking_P0 at indicated concentrations of Acceptor_P6_Cy5 with Donor_P1_Cy3 fixed at 10 nM, FIG. 1*h* shows FRET- PAINT images of Docking_P0 at the indicated concentration of Donor_P1 Alexa488 with Acceptor_P2_Cy5 fixed at 10 nM, and FIG. 1***i* shows FRET-PAINT images of Docking_P0 at the indicated concentration of Acceptor_P2_Cy5 with Donor_P1_Alexa488 fixed at 10 nM (Scale bar: 1 μm).

FIG. 1*j* compares SNRs of DNA-PAINT at varying Cy3 imager strand concentration and FRET-PAINT at varying Cy3 donor strand, and Cy5 acceptor strand concentrations and FIG. 1*k* compares SNRs of DNA-PAINT at varying Cy3 imager strand concentration and FRET-PAINT at varying Alexa488 donor strand, and Cy5 acceptor strand concentrations.

As shown in FIG. 1*a*, FRET-PAINT used three DNA strands (docking, donor, and acceptor strands). The docking strand (Docking_P0) labeled with a biotin at the 5'-end has two docking sites, each of which base-pairs with the donor or acceptor strand. To increase the FRET probability, a shorter length for the donor strand than for the acceptor strand was chosen whereas relatively a longer acceptor strand was used. The donor strand was labeled at the 3'-end with Alexa488 (Donor_P1_Alexa488) whereas the acceptor strand was labeled with Cy5 (Acceptor_P11_Cy5) at the 3'-end.

The sequences of the strands are as follows:

Docking_P0=5'-Biotin-TTGATCTACATATTCTT-CATTA-3' (SEQ ID NO: 1)

Donor_P1_Cy3=5'-TAATGAAGA-Cy3-3' (SEQ ID NO: 2)

Donor_P1_Alexa488=5'-TAATGAAGA-Alexa488-3' (SEQ ID NO: 2)

Acceptor_P2_Cy5=5'-Cy5-TATGTAGATC-3' (SEQ ID NO: 3)

Acceptor_P6_Cy5=5'-TATG-Cy5-TAGATC-3' (SEQ ID NO: 3) Acceptor_P11_Cy5=5'-TATGTAGATC-Cy5-3' (SEQ ID NO: 3)

Then, the docking strand was immobilized on the surface of a polymer-coated quartz surface using streptavidin-biotin interaction and took single-molecule images of Cy5 after injecting the donor (1000 nM) and acceptor (100 nM) strands by exciting Alexa488 using a blue laser (FIG. 1*b*).

As a result, clear Cy5 fluorescence intensity time terraces were obtained at high donor and acceptor concentrations, as shown in FIG. 1*c*.

The same scheme was carried out to find the optimum labeling position of FRET probes that gives maximum FRET signal for two FRET pairs (Cy3-Cy5 and Alexa488-Cy5). To this end, donor strands labeled with Cy3 (Donor_P1_Cy3) or Alex488 (Donor_P1_Alexa488) at the 3'-end, and acceptor strands labeled with Cy5 at varying positions (Acceptor_P2_Cy5, P4_Cy5, P6_Cy5, and P11_Cy5).

As a result, the Cy3-Cy5 FRET pair gave the highest Cy5 signal when the gap between donor and acceptor strands was 6 nt, whereas Alexa488-Cy5 FRET pair gave the highest Cy5 signal when the gap between donor and acceptor strands was 2 nt, as shown in FIG. 1*d*.

Then, super-resolution fluorescence images were recorded using HILO (Highly Inclined and Laminated Optical sheet) microscopy. Signal-to-noise ratios (SNRs) of DNA-PAINT and FRET-PAINT at varying DNA concentrations were compared.

The results are shown in FIGS. 1*e* to 1*i*. For DNA-PAINT, noise occurred in the single-molecule images when DNA concentration was above 5 nM (FIG. 1*e*). For Cy3-Cy5 pair FRET-PAINT, noise occurred when the DNA concentration was above 100 nM (FIGS. 1*f* and 1g). For Alexa488-Cy5 pair FRET-PAINT, noise occurred when the DNA concentration was above 150 nM (FIGS. 1*h* and 1*i*).

These images show that the same SNR can be obtained at higher imager concentrations in FRET-PAINT compared to DNA-PAINT. For instance, 5 nM imager concentration was used for DNA-PAINT to obtain 3.3 SNR, as shown in FIGS. 1*j* and 1*k*. For the same SNR, 180 nM donor and 120 nM acceptor concentrations were used for the Cy3-Cy5 pair FRET-PAINT and 250 nM donor and 90 nM acceptor concentrations were used for the Alexa488-C5 pair FRET-PAINT.

Example 1-2: Superresolution Imaging with DNA-PAINT and FRET-PAINT

The following experimental procedure was performed to compare the superresolution imaging speeds of DNA-PAINT and FRET-PAINT.

First, microtubules of COS-7 cells were immunostained with the anti-tubulin antibody which is labeled with Docking_P1.

Then, for DNA-PAINT, microtubules were imaged after injecting 1 nM Cy5-labeled imager strand (Acceptor_P2'_Cy5). For FRET-PAINT, microtubules of the same area were imaged after injecting 30 nM donor (Donor_P1_Alexa488) and 20 nM acceptor (Acceptor_P2_Cy5) strands. Single-molecule images were recorded at a frame rate of 10 Hz, which is fast enough to reliably detect binding of donor and acceptor strands.

To quantitatively compare the imaging speed of DNA-PAINT and FRET-PAINT, the number of spots of FIGS. 2*a* and 2*b* was measured. The same analysis was performed for nine additional imaging areas and the averaged speeds were compared. The convolved resolutions computed as $((\text{localization precision})^2+(\text{Nyquist resolution})^2)^{1/2}$ (6) were quantified to compare the imaging speeds of DNA-PAINT and FRET-PAINT. The localization precisions of DNA-PAINT and FRET-PAINT were 6.9 nm and 11.1 nm, respectively.

The results are shown in FIGS. 2*a* to 2*e*. FIGS. 2*a* to 2*e* compare the imaging speeds of DNA-PAINT and FRET-PAINT.

Specifically, FIG. 2*a* shows DNA-PAINT images reconstructed at specified acquisition time, FIG. 2*b* shows FRET-PAINT images of the same area as in FIG. 2*a* reconstructed at specified acquisition time, FIG. 2*c* shows the accumulated number of localized spots as a function of time for DNA-PAINT images of FIG. 2*a*, and FRET-PAINT images of FIG. 2*b*, FIG. 2*d* compares the number of localized single-molecule spots per second of FRET-PAINT and DNA-PAINT, and FIG. 2*e* compares spatial resolutions of DNA-PAINT and FRET-PAINT as a function of imaging time. The error bars represent standard deviation.

Since 18000 frames in total were recorded at a frame rate of 10 Hz for DNA-PAINT, the total imaging time was 30 min (FIG. 2*a*). On the other hand, since 600 frames in total were recorded at a frame rate of 10 Hz for FRET-PAINT, the total imaging time was 60 s (FIG. 2*b*). The imaging speed of FRET-PAINT increased 29-fold compared to DNA-PAINT (FIG. 2*c*). The average values measured for the different areas revealed a 32-fold increase in the imaging speed on average (FIG. 2*d*). The imaging speeds of DNA-PAINT and FRET-PAINT were compared based on their convolved resolutions, and as a result, a 36-fold increase was obtained in the imaging speed of FRET-PAINT (FIG. 2*e*).

Example 1-3: FRET-PAINT Multiplexed Imaging

The multiplexing capability of FRET-PAINT microscopy was assessed by the following experimental procedure.

Microtubules and mitochondria of COS-7 cells were immunostained using the anti-tubulin antibody and anti-Tom20 antibody, respectively. The anti-tubulin antibody and anti-Tom20 antibody were orthogonally conjugated with Docking_P1 and Docking_P2, respectively. In the present invention, two approaches were used for multiplexed imaging.

The results are shown in FIGS. 3*a* to 3*h*.

FIGS. 3*a* to 3*h* show multiplexed capability of FRET-PAINT. Specifically, FIG. 3*a* schematically shows multiplexed imaging that uses a donor and acceptor strand exchange scheme, FIGS. 3*b* to 3*d* show FRET-PAINT images of microtubule (3*b*) and mitochondria (3*c*) obtained using the scheme (3*a*), and (3*d*) an overlaid image of FIGS. 3*b* and 3*c*, FIG. 3*e* schematically shows multiplexed imaging without buffer exchange, and FIGS. 3*f* to 3*h* show FRET-PAINT images of microtubule (3*f*) and mitochondria (3*g*) obtained using the scheme (3*e*) and an overlaid image (3*h*) of FIGS. 3*f* and 3*g* (MT, microtubule; MC, mitochondria; DS, donor strand; AS, acceptor strand. Scale bars: 5 μm).

In the one approach shown in FIG. 3*a* (by sequential treatment with donor and acceptor strands), microtubules were first imaged by injecting 20 nM Donor_P1_AlexAF488 and 10 nM Acceptor_P2_Cy5 (FIG. 3*b*) and mitochondria were then imaged by injecting 10 nM Donor_P2_AF488 and 10 nM Acceptor_P2_Cy5 (FIG. 3*c*). In the second approach shown in FIG. 3*e* (by simultaneous treatment with donor and acceptor strands), after injection of all DNA probes (10 nM Donor_P1_Cy3 for microtubules, 20 nM Donor_P2_Alexa488 for mitochondria, and 10 nM Acceptor_P2'_Cy5 for both microtubules and mitochondria) at the same time, microtubules were first imaged with Cy3 excitation (FIG. 3*f*) and mitochondria were then imaged with Alexa488 excitation (FIG. 3*g*).

Even though there was no difference in imaging time between the two approaches, a disadvantage of the second approach (by simultaneous treatment with donor and acceptor strands) is a cross-talk between microtubule and mitochondria images. Thus, it was demonstrated that the sequential treatment with donor and acceptor strands is a better way to do multiplexing imaging.

Example 1-4: Measurement of Biomarkers in a Broad Concentration Range

The ability to measure biomarkers in a broad concentration range was assessed by the following experimental procedure.

FIGS. 4*a* to 4*c* show the quantification of biomarkers at various concentrations.

Specifically, FIG. 4*a* shows biomarkers at concentrations of 10, 40, 100, 400, 1000, and 10000 μg/ml immobilized in different wells and measured using donor and acceptor strands, FIG. 4*b* shows biomarkers at concentrations of 1000 μg/ml and 10000 μg/ml after 1/10 and 1/100 dilution before use, respectively, and FIG. 4*c* graphically shows the numbers of spots measured at the concentrations indicated in FIGS. 4*a* and 4*b*. In FIG. 4*c*, the 1000 μg/ml data were obtained by counting the number of spots after 1/10 dilution and multiplying the number by 10 and the 10000 μg/ml data were obtained by counting the number of spots after 1/100 dilution and multiplying the number by 100.

Biomarkers at concentrations of 10, 40, 100, 400, 1000, and 10000 μg/ml were immobilized in different wells and the numbers of spots (individual biomarker molecules) in images were measured using donor and acceptor strands (FIG. 4*a*). The number of spots in images increased in proportion to the concentration. The spots started to overlap at concentrations of ≥1000 μg/ml, making it impossible to accurately count their number.

Biomarkers at concentrations of 1000 and 10000 μg/ml were 1/10 and 1/100 diluted and immobilized in different wells and the numbers of spots in images were measured using donor and acceptor strands (FIG. 4*b*).

The numbers of spots counted at the indicated concentrations are plotted (FIG. 4*c*). The 1000 μg/ml data were obtained by counting the number of spots after 1/10 dilution and multiplying the number by 10 and the 10000 μg/ml data were obtained by counting the number of spots after 1/100 dilution and multiplying the number by 100.

When the data were fitted to linear functions, the correlation coefficient was calculated to be 0.99997. From this, it was concluded that accurate measurement results can be obtained even after biomarkers at high concentrations are diluted.

2. Multiplexed Detection of Biomarkers Using Two or More Types of Tagged Strands Labeled with Donor or Acceptor Fluorescent Substance Example 2-1: Construction of Database for FRET Efficiencies To construct a database for FRET efficiencies as explained previously, Cy3 as a donor and Cy5 as an acceptor were labeled on DNA strands to construct tagged strands. One end of the DNA was biotinylated, the donor and the acceptor were attached on a particular base and labeled such that the donor-acceptor distance was 1-50. A total of 50 types of tagged strands were prepared.

The reason for the biotinylation is to immobilize the DNA on the substrate using streptavidin-biotin interaction. To perform a similar role, the DNA could also be immobilized on the substrate using interactions among digoxigenin and its antibody or tags such as SNAP-tag, CLIP-tag, FLAG-tag, and His-tag, and respective ligands.

After the substrate was coated with streptavidin, DNA strands in which the donor-acceptor distance was 1 were immobilized and the FRET efficiency at the distance of 1 was measured to establish a reference value. The FRET efficiency may be a value obtained by compensating for the difference in the detection efficiency of an image sensor depending on differences in the wavelength of 1) light emitted from the acceptor excited when the donor is excited by light, 2) portions of light emitted from the donor and the acceptor that are not perfectly separated by a dichroic mirror, and 3) light emitted from the donor and the acceptor.

The same applied to the other distances of 2-50 to obtain their reference values. Errors caused by noise generated during measurement were calculated and only distances were used at which FRET efficiencies were actually clearly distinguishable. The following examples are based on the assumption that 10 of the FRET efficiency reference values are clearly distinguishable at the distances of 1-50.

Example 2-2: Tagged Strand Construction

Tagged strands were constructed as many as the number of types of actual target biomarkers. The DNA strands used in Example 2-1 could be used without modification, but a functional group capable of binding to detection antibodies was attached to the DNA strands instead of biotin labeled at one end of the DNA before use. The functional group was bound according to the known method for labeling a fluorescent substance on DNA.

Under the assumption that 10 FRET efficiencies are clearly distinguishable with one donor-acceptor pair in Example 2-1, 10 types of biomarkers can be sufficiently detected with only one donor-acceptor pair.

More than 10 types of target biomarkers can be detected using two or more donor-acceptor pairs. For example, when two donor-acceptor pairs are used, a maximum of 55 FRET efficiencies will be clearly distinguishable. When three donor-acceptor pairs are used, a maximum of 205 FRET efficiencies will be clearly distinguishable. If a maximum of 10 FRET efficiencies are distinguishable with one donor-acceptor pair, the number of FRET efficiencies distinguishable with two donor-acceptor pairs is 100, as calculated theoretically. However, FRET pair 1 whose FRET efficiencies are a and b cannot be distinguished from FRET pair 2 whose FRET efficiencies are b and a. Accordingly, when a tagged strand is labeled with either of FRET pair 1 or 2, a total of 55 FRET efficiencies can be substantially distinguished. When the types of the donors, the acceptors or all fluorescent substances in both FRET pairs 1 and 2 are different, 100 FRET efficiencies are distinguishable with the two pairs. 1000 FRET efficiencies are distinguishable with three pairs.

Example 2-3: Variation in FRET Efficiency Before and After Photobleaching

In this example, DNA strands labeled with donor 1-acceptor 1 and donor 2-acceptor 2 spaced a distance from each other were used. The brightness values of light from the donors and the acceptors and the FRET efficiencies of the donor-acceptor pairs were measured before photobleaching (Table 1). Each FRET efficiency may be a value obtained by compensating for the difference in the detection efficiency of an image sensor depending on differences in the wavelength of 1) light emitted from the acceptor excited when the donor is excited by light, 2) portions of light emitted from the donor and the acceptor that are not perfectly separated by a dichroic mirror, and 3) light emitted from the donor and the acceptor.

The FRET efficiency of FRET pair 1 is 0.5 and the FRET efficiency of FRET pair 2 is 0.7, but the actually observed FRET efficiency is 0.6, which is the average of the FRET efficiencies two FRET pairs. The FRET efficiencies of the two FRET pairs cannot be determined from the observed value.

TABLE 1

| Donor 1-acceptor 1 | | Donor 2-acceptor 2 | |
|---|---|---|---|
| Donor 1 | Acceptor 1 | Donor 2 | Acceptor 2 |
| 50 | 50 | 30 | 70 |
| FRET efficiency 0.5 | | FRET efficiency 0.7 | |

The four donors and acceptors shown in Table 1 may be photobleached. For the corrected FRET efficiencies, the sum of the brightness values of light from the donor and the acceptor in each FRET pair is constant before and after photobleaching. In this example, the sum is 100. The FRET efficiencies are measured as follows.

1) when Donor 1 is Photobleached

Since both donor 1 and acceptor 1 do not emit light, the sum of the brightness values of light from the donors is changed from 80 to 30 and the sum of the brightness values of light from the acceptors is changed from 120 to 70, with the result that the variations in brightness before and after photobleaching are 50 for the donors and 50 for the acceptors. That is, the FRET efficiency measured from the difference in brightness before and after photobleaching is 0.5 and the FRET efficiency measured from the brightness observed after photobleaching is 0.7. Accordingly, the FRET efficiencies of the corresponding tagged strand are 0.5 and 0.7.

2) when Donor 2 is Photobleached

Since both donor 2 and acceptor 2 do not emit light, the sum of the brightness values of light from the donors is changed from 80 to 50 and the sum of the brightness values of light from the acceptors is changed from 120 to 50, with the result that the variations in brightness before and after photobleaching are 30 for the donors and 70 for the acceptors. That is, the FRET efficiency measured from the difference in brightness before and after photobleaching is 0.7 and the FRET efficiency measured from the brightness observed after photobleaching is 0.5. Accordingly, the FRET efficiencies of the corresponding tagged strand are 0.5 and 0.7.

3) when Acceptor 1 is Photobleached

Since donor 1 emits light instead of acceptor 1, the sum of the brightness values of light from the donors is changed from 80 to 130 and the sum of the brightness values of light from the acceptors is changed from 120 to 70, with the result that the variations in brightness before and after photobleaching are 50 for the donors and 50 for the acceptors. The sum of the brightness values of light from the donors and the acceptors of the FRET pairs is maintained constant (100) before and after photobleaching, with the result that the FRET efficiency is 0.5 from the variation in the brightness of the acceptors (50). The FRET efficiency measured from the sum of the brightness values of light from the donors after photobleaching (130) except the brightness of light from donor 1 (100) is 0.7. Accordingly, the FRET efficiencies of the corresponding tagged strand are 0.5 and 0.7.

4) when Acceptor 2 is Photobleached

Since donor 2 emits light instead of acceptor 2, the sum of the brightness values of light from the donors is changed from 80 to 150 and the sum of the brightness values of light from the acceptors is changed from 120 to 50, with the result that the variations in brightness before and after photobleaching are 70 for the donors and 70 for the acceptors. The sum of the brightness values of light from the donors and the acceptors of the FRET pairs is maintained constant (100) before and after photobleaching, with the result that the FRET efficiency is 0.7 from the variation in the brightness of the acceptors (70). The FRET efficiency measured from the sum of the brightness values of light from the donors after photobleaching (150) except the brightness of light from donor 2 (100) is 0.5. Accordingly, the FRET efficiencies of the corresponding tagged strand are 0.5 and 0.7.

The brightness is measured until one fluorescent substance is photobleached and this procedure is repeated for the other fluorescent substances, revealing that the FRET efficiencies of the corresponding tagged strand are 0.5 and 0.7.

Example 2-4: Measurement of FRET Efficiencies and Identification of Types of Biomarkers A kit for detecting biomarkers 1 and 2 was fabricated by the following procedure. Tagged strand 1 was conjugated to detection antibody 1 bound to biomarker 1 and tagged strand 2 was conjugated to detection antibody 2 bound to biomarker 2. Each of the tagged strands 1 and 2 was labeled with two donor-acceptor FRET pairs. The FRET efficiency reference values of detection antibody 1 were 0.1 for FRET pair 1 and 0.5 for FRET pair 2. The FRET efficiency reference values of detection antibody 2 were 0.2 for FRET pair 1 and 0.4 for FRET pair 2.

Thereafter, the difference in brightness before and after photobleaching was measured to analyze the FRET efficiencies, as in Example 2-3. Molecules A and B were observed with an imaging camera for brightness observation. The FRET efficiencies of molecule A were measured to be 0.1 and 0.5, indicating that molecule A is biomarker 1. Based on the same principle, the FRET efficiencies of molecule B were measured to be 0.2 and 0.4, indicating that molecule B is biomarker 2 (FIG. 15).

The concentrations of biomarkers in a sample greatly vary from fg/ml to mg/ml depending on the biomarker types. When a biomarker at an excessively high concentration is immobilized onto a substrate, an excessively large number of spots are observed in one image and overlap with one another. This overlap makes it impossible to measure the FRET efficiencies of the individual molecules. Therefore, the sample can be diluted in various ratios such that proper numbers of the biomarker molecules are detected in one image.

When it intends to detect biomarkers in similar concentration ranges, the biomarkers are diluted in the same ratio for analysis. For example, if biomarkers, usually at concentrations of ~1 ng/ml, are diluted in a 1:100 ratio and proper numbers of the biomarker molecules are detected in one image, biomarkers, usually at concentrations of ~100 ng/ml, are diluted in a 1:10000 ratio for analysis.

3. Multiplexed Detection of Biomarkers Using N Types of Docking Strands and N Types of FRET Strands

Example 3-1: Construction of Database for FRET Efficiencies

Different fluorescent substances A, B, and C were used as donor 1, donor 2, and an acceptor, respectively. Donor 1 was labeled on donor strands and donor 2 and the acceptor were labeled on FRET strands.

The distance between two fluorescent substances A and B was set such that the FRET efficiency of donors 1 and 2 was a maximum. Fluorescent substances B and C labeled on the FRET strands constituted a FRET pair. The FRET strands were labeled with different FRET pairs as many types as necessary.

For example, when 50 types were necessary for a database, 50 types of FRET strands labeled with fluorescent substances B and C at different distances were prepared. When commercially available fluorescent substances are used as donor 1, donor 2, and the acceptor, commercially available FRET strands labeled with donor 1, donor 2, and the acceptor can be used without performing the above procedure.

In the determination of the fluorescent substances as donor 1, donor 2, and the acceptor, it is preferable that the peak emission wavelength of donor 1 is the shortest and that of the acceptor is the longest.

After the two or more types of FRET strands were prepared, the FRET strands and the donor strands, in which the donor 2-acceptor distance was 1, were allowed to bind to docking strands and the FRET efficiency at the corresponding distance was measured. Thereafter, the same procedure was repeated from the FRET strands in which the distance between the donor 2-acceptor FRET pairs was 2, to obtain FRET efficiency reference values, which were constructed into a database.

Thereafter, the FRET efficiency values measured during biomarker detection were compared with the FRET efficiency reference values. From this comparison, the donor 2-acceptor distances of the FRET pairs were determined to identify the types of the detected biomarkers.

However, since errors may be caused by noise generated during FRET efficiency measurement, the FRET efficiencies at all distances are not distinguishable. For example, when the FRET efficiency is 0.95 (mean)+0.05 (error) at a distance of 1 and 0.94±0.05 at a distance of 2, the distances (1 and 2) cannot be distinguished by the FRET efficiencies. Thus, it is preferable to use distances at which the FRET efficiencies are clearly distinguished among the values stored in the database during the actual detection of biomarkers. The following examples are based on the assumption that 10 of the FRET efficiency reference values are clearly distinguishable at the distances of 1-50.

Example 3-2: Construction of N Types of Docking Strands and N Types of FRET Strands Docking strands were constructed as many as the number of types of actual target biomarkers.

Under the assumption that 10 FRET efficiencies are clearly distinguishable with one donor 2-acceptor FRET pair in Example 3-1, 10 types of biomarkers can be sufficiently detected with only one donor 2-acceptor FRET pair. Thus, one FRET strand was allowed to bind to each docking strand.

More than 10 types of target biomarkers can be detected using two or more donor 2-acceptor pairs. Thus, two or more FRET strands were allowed to bind to each docking strand. For example, when two FRET pairs are used, a maximum of 55 FRET efficiencies will be clearly distinguishable. When three FRET pairs are used, a maximum of 205 FRET efficiencies will be clearly distinguishable. If a maximum of 10 FRET efficiencies are distinguishable with one FRET pair, the number of FRET efficiencies distinguishable with two FRET pairs is 100, as calculated theoretically. However, FRET pair 1 whose FRET efficiencies are a and b cannot be distinguished from FRET pair 2 whose FRET efficiencies are b and a. Accordingly, when a docking strand is labeled with either of FRET pair 1 or 2, a total of 55 FRET efficiencies can be substantially distinguished. When the types of the donors 2, the acceptors or all fluorescent substances in both FRET pairs 1 and 2 are different, 100 FRET efficiencies are distinguishable with the two pairs. 1000 FRET efficiencies are distinguishable with three pairs.

Example 3-3: FRET Efficiency Measurement and Biomarker Identification

A kit for detecting biomarkers 1 and 2 was fabricated by the following procedure.

Docking strand 1 was conjugated to detection antibody 1 bound to biomarker 1 and docking strand 2 was conjugated to detection antibody 2 bound to biomarker 2. Each of the docking strands 1 and 2 was allowed to bind with two types of FRET strands. Specifically, a FRET strand whose FRET efficiencies were 0.2 and 0.4 was allowed to bind to docking strand 1 and another FRET strand whose FRET efficiencies were 0.6 and 0.8 was allowed to bind to docking strand 2.

Biomarkers 1 and 2 were immobilized on a substrate and allowed to bind with detection antibodies 1 and 2, respectively. A buffer containing donor strands and four types of FRET strands having FRET efficiencies of 0.2, 0.4, 0.6, and 0.8 was placed in wells, and the FRET efficiencies of the FRET strands bound to the docking strands were measured. As described regarding FIG. 29, the locations of molecules 1 and 2 were observed as intermittent fluorescence signals with an imaging camera for observing the brightness values of donor 2 and the acceptor. The brightness values of donor 2 and the acceptor were measured to analyze the FRET efficiencies. As a result, the FRET efficiencies were measured to be 0.2 and 0.4 at the location of the molecule 1, indicating that the molecule 1 was biomarker 1. Based on the same principle, the FRET efficiencies were measured to be 0.2 and 0.4 at the location of molecule 2, indicating that molecule 2 is biomarker 2.

The concentrations of biomarkers in a sample greatly vary from fg/ml to mg/ml depending on the biomarker types. When a biomarker at an excessively high concentration is immobilized onto a substrate, an excessively large number of spots are observed in one image and overlap with one another. This overlap makes it impossible to measure the FRET efficiencies of the individual molecules. Therefore, the sample can be diluted in various ratios such that proper numbers of the biomarker molecules are detected in one image.

When it intends to detect biomarkers in similar concentration ranges, the biomarkers are diluted in the same ratio for analysis. For example, if biomarkers, usually at concentrations of ~1 ng/ml, are diluted in a 1:100 ratio and proper numbers of the biomarker molecules are detected in one image, biomarkers, usually at concentrations of ~100 ng/ml, are diluted in a 1:10000 ratio for analysis.

4. Multiplexed Detection of Biomarkers Using N Types of Docking Strands, Donor Strands, and Acceptor Strands

Example 4-1: Construction of Database for the Emission Spectra

A types (where A is an integer of 1 or more) of donor strands labeled with A types of donors excitable by one light source were constructed. B types (where B is an integer of 1 or more) of acceptor strands labeled with B types of acceptors that form FRET pairs with the A types of donors were constructed. A total of A×B types of docking strands capable of complementary binding with the A types of donor strands and the B types of acceptor strands were constructed.

The emission spectra of the donors and the acceptors were measured using donor strand 1, acceptor strand 1, and docking strand 1 complementary thereto. The same applied to the emission spectra of the other donor strands and the acceptor strands.

Taking errors caused by noise in the measured A×B emission spectra into consideration, only clearly distinguishable ones of the emission spectra were used to construct a database and only combinations of the donor strands and the acceptor strands providing the corresponding emission spectra were used for biomarker detection.

The method described above is to explain the structure shown in FIG. 36*b* in a combination of the methods shown in FIGS. 31 and 33. When the number of the emission spectra stored in the database is smaller than the number of target biomarkers, the structure of FIG. 32 constructed such that the FRET efficiencies between the donors and the acceptors are different is further applied, two or more types of acceptors are labeled on one acceptor strand, as shown in FIG. 36*b*, or two or more different types of acceptor strands are allowed to bind to one docking strand, with the result that a larger number of emission spectra than the number of target biomarkers are stored in the database.

Example 4-2: Construction of N Types of Docking Strands, Donor Strands, and Acceptor Strands N types of docking strands were constructed to detect N types of biomarkers. The N types of docking strands had sequences complementary to the sequences of donor strands and acceptor strands that provide their emission spectra to a database.

Example 4-3: Measurement of Emission Spectra and Identification of Biomarkers A kit for detecting two types of biomarkers was fabricated by the following procedure.

Docking strand 1 was conjugated to detection antibody 1 bound to biomarker 1 and docking strand 2 was conjugated to detection antibody 2 bound to biomarker 2. Donor strand 1 and acceptor strand 1 were allowed to bind to docking strand 1 and donor strand 2 and acceptor strand 2 were allowed to bind to docking strand 2.

Biomarkers 1 and 2 were immobilized on a substrate and allowed to bind with detection antibodies 1 and 2, respectively. A buffer containing donor strand 1, acceptor strand 1, donor strand 2, and acceptor strand 2 was placed in wells, and the spectra of light emitted when the donor strands and the acceptor strands were simultaneously bound to the docking strands were observed. As shown in FIG. 37, intermittent fluorescence signals were observed at the locations of molecules 1 and 2 in images taken with an imaging camera. The emission spectra at the corresponding locations were compared with those stored in a database to identify the types of the biomarkers.

The concentrations of biomarkers in a sample greatly vary from fg/ml to mg/ml depending on the biomarker types. When a biomarker at an excessively high concentration is immobilized onto a substrate, an excessively large number of spots are observed in one image and overlap with one another. This overlap makes it impossible to measure the FRET efficiencies of the individual molecules. Therefore, the sample can be diluted in various ratios such that proper numbers of the biomarker molecules are detected in one image.

When it intends to detect biomarkers in similar concentration ranges, the biomarkers are diluted in the same ratio for analysis. For example, if biomarkers, usually at concentrations of ~1 ng/ml, are diluted in a 1:100 ratio and proper numbers of the biomarker molecules are detected in one image, biomarkers, usually at concentrations of ~100 ng/ml, are diluted in a 1:10000 ratio for analysis.

Although the exemplary embodiments have been described with reference to the limited drawings, those skilled in the art will understand that various technical alterations and modifications based on the above description can be made to the embodiments. For example, appropriate results can be achieved even when the described technique may be performed in a different order from the described method and/or even when the described components are coupled or combined in a different form from the described method or are replaced or substituted by other components or equivalents. Therefore, other embodiments, other examples, and equivalents of claims are encompassed within the scope of the appended claims.

The invention claimed is:

1. A method for detecting target substances, comprising:

a) introducing a sample containing target substances onto a substrate;

b) allowing detection probes conjugated with docking strands to specifically bind to the target substances;

c) introducing separate strands capable of complementary binding to the docking strand, wherein the separate strands comprise one or more of donor strand labeled with a first donor fluorescent substance and one or more of acceptor strand labeled with a second donor fluorescent substance and an acceptor fluorescent substance that forms a FRET pair with the second donor fluorescent substance; and d) measuring fluorescence signals generated by the FRET between the second donor fluorescent substance and the acceptor fluorescent substance to identify the target substances.

2. The method according to claim 1, wherein the peak absorption wavelength of the second donor fluorescent substance is shorter than that of the acceptor fluorescent substance and the peak emission wavelength of the second donor fluorescent substance is shorter than that of the acceptor fluorescent substance.

3. The method according to claim 1, wherein the extinction coefficient of the second donor fluorescent substance at a wavelength of light exciting the second donor fluorescent substance is at least 3 times higher than that of the acceptor fluorescent substance.

4. The method according to claim 1, wherein the Förster radius between the second donor fluorescent substance and the acceptor fluorescent substance is at least 0.208 nm.

5. The method according to claim 1, wherein the second donor fluorescent substance and the acceptor fluorescent substance are attached to the acceptor strand via linkers.

6. The method according to claim 5, wherein the linkers are 10 nm or less in length.

7. The method according to claim 1, wherein the signal-to-noise ratio of the fluorescence signals is at least 2.

8. The method according to claim 1, wherein the target substances are of two or more types and one or more of the donor strands or the acceptor strands have different sequences depending on the types of the target substances or are labeled with fluorescent substances of different types or at different sites.

9. The method according to claim 8, further comprising removing the donor strands and/or the acceptor strands after identification of the target substances and repeating step d) using donor strands and/or acceptor strands different from the removed donor strands and/or acceptor strands to identify the other target substances.

10. The method according to claim 1, wherein when the donor strands and the acceptor strands bind simultaneously or sequentially to the docking strands, any gaps—between the donor strands and the acceptor strands are smaller than the persistence length of the docking strands.

11. The method according to claim 1, further comprising controlling the concentration of the donor strands or the acceptor strands such that the time it takes for the donor strands or the acceptor strands to bind to the docking strands is 10 minutes or less while maintaining the signal-to-noise ratio of the fluorescence signals at 2 or more.

12. The method according to claim 11, wherein the concentration of the donor strands or the acceptor strands is from 10 nM to 10 μM.

13. The method according to claim 1, wherein when the docking strands or the acceptor strands are nucleic acids, the number of the bases of the acceptor strands complementary to the docking strands is at least 8.

14. The method according to claim 13, wherein the number of the bases of the donor strands complementary to the docking strands is from 6 to 12.

15. The method according to claim 1, wherein when the docking strands or the acceptor strands are nucleic acid analogues, the number of the bases of the acceptor strands complementary to the docking strands is at least 5.

16. The method according to claim 15, wherein the number of the bases of the donor strands complementary to the docking strands is from 3 to 9.

17. The method according to claim 1, wherein the following equation:

FRET efficiency=(Intensity of light from acceptor)/(Sum of intensity of light from donor and intensity of light from acceptor)

is used to measure FRET efficiency of the fluorescence signals.

18. The method according to claim 1, wherein two or more target substances are simultaneously identified by determining the difference between the FRET efficiencies distinguished depending on the distances between the second donor fluorescent substance and the acceptor fluorescent substance.

19. The method according to claim 1, wherein two or more target substances are simultaneously identified by determining the difference between the emission spectra by the FRET for different types of the second donor fluorescent substance or the acceptor fluorescent substance.

20. The method according to claim 1, further comprising determining the concentrations of the target substances in the sample from the numbers of the target substances per unit area of a region where the fluorescence signals are imaged.

* * * * *

SEQUENCE LISTING

```
<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Synthesized

<400> SEQUENCE: 1

ttgatctaca tattcttcat ta                                22


<210> SEQ ID NO 2
<211> LENGTH: 9
<212> TYPE: DNA
<213> ORGANISM: Artificial Sequence
<220> FEATURE:
<223> OTHER INFORMATION: Synthesized

<400> SEQUENCE: 2

taatgaaga                                                9


<210> SEQ ID NO 3
<211> LENGTH: 10
<212> TYPE: DNA
<213> ORGANISM: Artificial Sequence
<220> FEATURE:
<223> OTHER INFORMATION: Synthesized

<400> SEQUENCE: 3

tatgtagatc                                              10
```